US010736910B2

(12) United States Patent
Deretic et al.

(10) Patent No.: US 10,736,910 B2
(45) Date of Patent: Aug. 11, 2020

(54) TREATMENT OF AUTOPHAGY-BASED DISORDERS AND RELATED PHARMACEUTICAL COMPOSITIONS, DIAGNOSTIC AND SCREENING ASSAYS AND KITS

(71) Applicant: STC.UNM, Albuquerque, NM (US)

(72) Inventors: Vojo P. Deretic, Placitas, NM (US); Eliseo F. Castillo, Albuquerque, NM (US)

(73) Assignee: STC.UNM, Albuquerque, NM (US)

(*) Notice: Subject to any disclaimer, the term of this patent is extended or adjusted under 35 U.S.C. 154(b) by 0 days.

(21) Appl. No.: 16/130,015

(22) Filed: Sep. 13, 2018

(65) Prior Publication Data
US 2019/0008882 A1    Jan. 10, 2019

Related U.S. Application Data

(62) Division of application No. 14/434,931, filed as application No. PCT/US2013/064946 on Oct. 15, 2013, now abandoned.
(Continued)

(51) Int. Cl.
| | | |
|---|---|---|
| *A61K 31/704* | (2006.01) | |
| *A61K 45/06* | (2006.01) | |
| *A61K 31/436* | (2006.01) | |
| *A61K 31/00* | (2006.01) | |
| *A61K 31/506* | (2006.01) | |
| *A61K 31/713* | (2006.01) | |

(Continued)

(52) U.S. Cl.
CPC ............ *A61K 31/704* (2013.01); *A61K 31/00* (2013.01); *A61K 31/277* (2013.01); *A61K 31/38* (2013.01); *A61K 31/381* (2013.01); *A61K 31/4184* (2013.01); *A61K 31/436* (2013.01); *A61K 31/4365* (2013.01); *A61K 31/4453* (2013.01); *A61K 31/4535* (2013.01); *A61K 31/472* (2013.01); *A61K 31/473* (2013.01); *A61K 31/475* (2013.01); *A61K 31/495* (2013.01); *A61K 31/506* (2013.01); *A61K 31/5415* (2013.01); *A61K 31/57* (2013.01); *A61K 31/65* (2013.01); *A61K 31/713* (2013.01); *A61K 38/177* (2013.01); *A61K 38/1793* (2013.01); *A61K 45/06* (2013.01); *C07K 16/245* (2013.01); *C07K 16/28* (2013.01); *G01N 33/5055* (2013.01); *G01N 33/5695* (2013.01); *G01N 33/6842* (2013.01); *G01N 33/6893* (2013.01); *A61K 9/0073* (2013.01); *A61K 38/00* (2013.01); *A61P 11/10* (2018.01); *A61P 11/12* (2018.01); *A61P 31/04* (2018.01); *A61P 31/06* (2018.01); *C07K 2317/76* (2013.01); *G01N 2333/4703* (2013.01); *G01N 2333/4719* (2013.01); *G01N 2333/4724* (2013.01); *G01N 2333/54* (2013.01); *G01N 2333/545* (2013.01); *G01N 2333/90212* (2013.01); *G01N 2500/02* (2013.01); *G01N 2500/20* (2013.01)

(58) Field of Classification Search
CPC ...... A61K 31/00; A61K 31/277; A61K 31/38; A61K 31/381; A61K 31/4184; A61K 31/436; A61K 31/4365; A61K 31/4453; A61K 31/4535; A61K 31/472; A61K 31/473; A61K 31/475; A61K 31/495; A61K 31/506; A61K 31/5415; A61K 31/57; A61K 31/65; A61K 31/704; A61K 31/713; A61K 38/00; A61K 38/177; A61K 38/1793; A61K 45/06; A61K 9/0073; C07K 16/245; C07K 16/28; C07K 2317/76; A61P 31/00; A61P 31/04; A61P 31/06; A61P 11/00; A61P 11/10; A61P 11/12
See application file for complete search history.

(56) References Cited

U.S. PATENT DOCUMENTS

| | | |
|---|---|---|
| 8,377,636 B2 | 2/2013 | Haley |
| 8,679,769 B2 | 3/2014 | Nagore |

(Continued)

FOREIGN PATENT DOCUMENTS

| | | |
|---|---|---|
| WO | 2007106425 A2 | 9/2007 |
| WO | 2010045270 A2 | 4/2010 |

(Continued)

OTHER PUBLICATIONS

Makoto Imaoka, "Preclinical and Clinical Investigation About Combination Effects of Expectorants in Chemotherapy of Infectious Respiratory Diseases", 1986, Chemotherapy, 34(3), pp. 262-270 (doi.org/1011250/chemotherapy1953.34.262) (Year: 1986).*
(Continued)

*Primary Examiner* — My-Chau T. Tran
(74) *Attorney, Agent, or Firm* — Henry D. Coleman; R. Neil Sudol

(57) ABSTRACT

In one embodiment, the invention provides a method of treating a subject suffering from a *Mycobacterium* infection by administering to the subject a therapeutically-effective amount of a degradative autophagy agonist or a secretory autophagy antagonist. In another embodiment, the invention provides a method of treating a subject suffering from one or more diseases selected from the group consisting of a *Mycobacterium* infection, an inflammatory disorder, an immune disorder, a cancer and a neurodegenerative disorder by administering to the subject a therapeutically-effective amount of a TBK-1 antagonist (e.g. BX795 or amlexanox). Related pharmaceutical compositions, diagnostic and screening assays and kits are also provided.

10 Claims, 27 Drawing Sheets

Related U.S. Application Data

(60) Provisional application No. 61/713,919, filed on Oct. 15, 2012, provisional application No. 61/713,843, filed on Oct. 15, 2012.

(51) Int. Cl.

| | |
|---|---|
| *G01N 33/50* | (2006.01) |
| *G01N 33/569* | (2006.01) |
| *G01N 33/68* | (2006.01) |
| *A61K 31/277* | (2006.01) |
| *A61K 31/38* | (2006.01) |
| *A61K 31/381* | (2006.01) |
| *A61K 31/4184* | (2006.01) |
| *A61K 31/4365* | (2006.01) |
| *A61K 31/4453* | (2006.01) |
| *A61K 31/4535* | (2006.01) |
| *A61K 31/472* | (2006.01) |
| *A61K 31/473* | (2006.01) |
| *A61K 31/475* | (2006.01) |
| *A61K 31/495* | (2006.01) |
| *A61K 31/5415* | (2006.01) |
| *A61K 31/57* | (2006.01) |
| *A61K 31/65* | (2006.01) |
| *A61K 38/17* | (2006.01) |
| *C07K 16/24* | (2006.01) |
| *C07K 16/28* | (2006.01) |
| *A61K 38/00* | (2006.01) |
| *A61K 9/00* | (2006.01) |
| *A61P 31/06* | (2006.01) |
| *A61P 11/12* | (2006.01) |
| *A61P 31/04* | (2006.01) |
| *A61P 11/10* | (2006.01) |

(56) References Cited

U.S. PATENT DOCUMENTS

| | | |
|---|---|---|
| 9,101,573 B2 | 8/2015 | Bassaganya-Riera |
| 9,572,820 B2 | 2/2017 | Deretic |
| 2008/0161324 A1* | 7/2008 | Johansen ............ A61K 31/135 514/255.03 |
| 2008/0293070 A1 | 11/2008 | Sekaly |
| 2009/0221430 A1 | 9/2009 | Wu |
| 2010/0009970 A1* | 1/2010 | Johansen ............ A61K 31/136 514/218 |
| 2010/0197621 A1 | 8/2010 | Henry et al. |
| 2014/0135296 A1 | 5/2014 | Deretic |
| 2019/0060289 A1* | 2/2019 | Deretic ............... G01N 33/6893 |

FOREIGN PATENT DOCUMENTS

| | | |
|---|---|---|
| WO | 2010139985 A1 | 12/2010 |
| WO | 2012032360 A2 | 3/2012 |
| WO | 2012154944 A2 | 11/2012 |

OTHER PUBLICATIONS

Davies et al., "Deposition and clearance of monodisperse aerosols in the calf lung: effects of particle size and a mucolytic agent (bromhexine)", 1987, Canad. J. Veter. Res., 51(3), pp. 306-311. (Year: 1987).*

Grange et al., "Activity of bromhexine and ambroxol, semi-synthetic derivatives of vasicine from the Indian shrub *Adhatoda vasica*, against *Mycobacterium tuberculosis* in vitro", 1996, Journal of Ethnophannacology, 50(1), pp. 49-53. (Year: 1996).*

Ren et al., "Influence of Formulation and Preparation Process on Ambroxol Hydrochloride Dry Powder Inhalation Characteristics and Aerosolization Properties", 2008, Drug Development and Industrial Pharmacy, 34(9), pp. 984-991. (Year: 2008).*

Feng et al.; Proteomics for the early detection and treatment of hepatocellular carcinoma. Oncogene 2006; vol. 257 nr. 27, pp. 3810-3817.

Deretic, Vojo; Autophagy in Infection; Current Opinion in Cell Biology 2010; vol. 22, nr. 2, pp. 252-262.

Cheallaigh et al.; Autophagy in the immune response to tuberculosis: clinical perspectives. Clinical and Experimental Immunology; vol. 164, nr. 4, pp. 291-300.

Radosavljevic et al.; The roles of Galectin-3 in autoimmunity and tumor progression. Immunol. Res. 2012; vol. 52, nr. 1, pp. 100-110.

Tucci et al.; Pathogen-derived biomarkers to active tuberculosis diagnosis. Frontiers in Microbiology 2014; vol. 5, nr. 549, pp. 1-6.

Jacobs et al.; Identification of novel host biomarkers in plasma as candidates for the immunodiagnosis of tuberculosis disease and monitoring of tuberculosis treatment response. Oncotarget 2016; vol. 7, nr. 36, pp. 57581-57592.

Mortensen et al.; Fragments of Citrullinated and MMPdegraded Vimentin and MMP-degraded Type III Collagen are Novel Serological Biomarkers to Differentiate Crohn's Disease from Ulcerative. Journal of Crohn's and Colitis 2015; vol. 9, nr. 10, pp. 863-872.

National Center for Biotechnology Information. PubMed Compound Database, CID=35802, https://pubchem.ncbinim.nih.gov/compound/35802 (created Mar. 26, 2005; accessed Jun. 25, 2018). (Year: 2005).

Zhao et al.; Evaluation of P38 MAPK Pathway as a Molecular Signature in ulcerative Colitis. J. Proteome Res. 2011; vol. 10, nr. 5, pp. 2216-2225.

Henderson et al.; A role for vimentin in Crohn disease. Autophagy 2012; vol. 8, nr. 11, pp. 1695-1696.

Plevy et al.; Combined Serological, Genetic, and Inflammatory Markers Differentiate Non-IBD,Crohn's Disease, and Ulcerative Colitis Patients. Inflamm Bowel Dis 2013; vol. 19, nr. 6, pp. 1139-1148.

Mizushima N, et al. (2011) The role of atg proteins in autophagosome formation. Annual review of cell and developmental biology 27:107-132.

Mizushima N, et al.(2008) Autophagy fights disease through cellular self-digestion. Nature 451(7182):1069-1075.

Levine B, et al. (2011) Autophagy in immunity and inflammation. Nature 469(7330):323-335.

Narita M, et al. (2011) Spatial coupling of mTOR and autophagy augments secretory phenotypes. Science 332 (6032):966-970.

Manjithaya R, Anjard C, Loomis WF, & Subramani S (2010) Unconventional secretion of Pichia pastoris Acb1 is dependent on GRASP protein, peroxisomal functions, and autophagosome formation. J Cell Biol 188 (4):537-546.

Dupont N, et al. (2011) Autophagy-based unconventional secretory pathway for extracellular delivery of IL-1beta. The EMBO journal 30(23):4701-4711.

Deretic V, Jiang S, & Dupont N (2012) Autophagy intersections with conventional and unconventional secretion in tissue development, remodeling and inflammation. Trends in Cell Biology In pres.

He C & Levine B.(2010) The Beclin 1 interactome. Current opinion in cell biology 22(2)140-149.

Tattoli I, et al. (2012) Amino acid starvation induced by invasive bacterial pathogens triggers an innate host defense program. Cell Host & Microbe 11(6):563-575.

Criollo A, et al. (2011) Inhibition of autophagy by TAB2 and TAB3. The EMBO journal 30(24):4908-4920.

Lee HK, Lund JM, Ramanathan B, Mizushima N, & Iwasaki A (2007) Autophagy-dependent viral recognition by plasmacytoid dendritic cells. Science 315(5817):1398-1401.

Saitoh T & Akira S (2010) Regulation of innate immuneresponses by autophagy-related proteins. J Cell Biol 189 (6):925-935.

Thurston TL, Wandel MP, Von Muhlinen N, Foeglein A, & Randow F (2012) Galectin 8 targets damaged vesicles for autophagy to defend cells against bacterial invasion. Nature 482(7385):414-418.

Deretic V (2012) Autophagy—an emerging immunological paradigm. J Immunol In press.

Jounai N, et al. (2011) NLRP4 negatively regulates autophagic processes through an association with beclin1. J Immunol 186(3):1646-1655.

(56) References Cited

OTHER PUBLICATIONS

Tal MC, et al. (2009) Absence of autophagy results in reactive oxygen species-dependent amplification of RLR signaling. Proc Natl Acad Sci U S A 106(8):2770-2775.
Xu Y, et al. (2007) Toll-like receptor 4 is a sensor for autophagy associated with innate immunity. Immunity 27 (1):135-144.
Delgado MA, Elmaoued RA, Davis AS, Kyei G, & Deretic V (2008) Toll-like receptors control autophagy. Embo J 27(7):1110-1121.
Travassos LH, et al. (2010) Nod1 and Nod2 direct autophagy by recruiting ATG16L1 to the plasma membrane at the site of bacterial entry. Nature immunology 11(1):55-62.
Lee HK, et al. (2010) In vivo requirement for Atg5 in antigen presentation by dendritic cells. Immunity 32(2):227-239.
Jia W, Pua HH, Li QJ, & He YW (2011) Autophagy regulates endoplasmic reticulum homeostasis and calcium mobilization in T lymphocytes. J Immunol 186(3):1564-1574.
Harris J, et al. (2007) T helper 2 cytokines inhibit autophagic control of intracellular *Mycobacterium tuberculosis*. Immunity 27(3):505-517.
Zhou R, Yazdi AS, Menu P, & Tschopp J (2011) A role for mitochondria in NLRP3 inflammasome activation.
Nakahira K, et al. (2011) Autophagy proteins regulate innate immune responses by inhibiting the release of mitochondrial DNA mediated by the NALP3 inflammasome. Nature immunology 12(3):222-230.
Shi CS, et al. (2012) Activation of autophagy by inflammatory signals limits IL-1 beta production by targeting ubiquitinated inflammasomes for destruction. Nature immunology 13(3):255-263.
Gutierrez MG, et al. (2004) Autophagy is a defense mechanism inhibiting BCG and *Mycobacterium tuberculosis* survival in infected macrophages. Cell 119(6):753-766.
Alonso S, Pethe K, Russell DG, & Purdy GE (2007) Lysosomal killing of *Mycobacterium* mediated by ubiquitin-derived peptides is enhanced by autophagy. Proc Natl Acad Sci U S A 104(14):6031-6036.
Yuk JM, et al. (2009) Vitamin D3 induces autophagy in human monocytes/macrophages via catheliddin. Cell host & microbe 6(3):231-243.
Kim JJ, et al. (2012) Host cell autophagy activated by antibiotics is required for their effective antimycobacterial drugaction. Cell host & microbe 11(5):457-468.
Nakagawa I, et al. (2004) Autophagy defends cells against invading group A *Streptococcus*. Science 306 (5698):1037-1040.
Deretic V (2012) Autophagy as an innate immunity paradigm: expanding the scope and repertoire of pattern recognition receptors. Current opinion in immunology 24(1):21-31.
Ponpuak M, et al. (2010) Delivery of cytosolic components by autophagic adaptor protein p62 endows autophagosomes with unique antimicrobial properties. Immunity 32(3):329-341.
Vergne I, Chua J, Singh SB, & Deretic V (2004) Cell biology of *Mycobacterium tuberculosis* phagosome. Annu Rev Cell Dev Biol 20:367-394.
Zhao Z, et al. (2008) Autophagosome-independent essential function for the autophagy protein Atg5 in cellular immunity to intracellular pathogens. Cell Host Microbe 4(5):458-469.
Flynn JL & Chan J (2001) Immunology of tuberculosis. Annu Rev lmmunol 19:93-129.
Korn T, Bettelli E, Oukka M, & Kuchroo VK (2009) IL-17 and Th17 Cells. Annual review of immunology 27:485-517.
Chung Y, et al. (2009) Critical regulation of early Th17 cell differentiation by interleukin-1 signaling. Immunity 30 , (4):576-587.
Yang H, et al. (2011) Three protein cocktails mediate delayed-type hypersensitivity responses indistinguishable from that elicited by purified protein derivative in the guinea pig model of *Mycobacterium tuberculosis* infection. Infect Immun 79(2):716-723.
Mayer-Barber KD, et al. (2011) Innate and Adaptive Interferorts Suppress IL-1alpha and IL-1beta Production by Distinct Pulmonary Myeloid Subsets during *Mycobacterium tuberculosis* Infection. Immunity 35(6):1023-1034.

Jain A, et al. (2010) p62/SQSTM1 is a target gene for transcription factor NRF2 and creates a positive feedback loop by inducing antioxidant response element-driven gene transcription. J Biol Chem 285(29):22576-22591.
Moscat J & Diaz-Meco MT (2009) p62 at the crossroads of autophagy, apoptosis, and cancer. Cell 137 (6):1001-1004.
Mathew R, et al. (2009) Autophagy suppresses tumorigenesis through elimination of p62. Cell 137(6)1062-1075.
Xia Y, et al. (1999) RelB modulation of IkappaBalpha stability as a mechanism of transcription suppression of interleukin-1alpha (IL-1alpha), IL-1 beta, and tumor necrosis factor alpha in fibroblasts. Molecular and cellular biology 19(11):7688-7696.
Fettelschoss A, et al. (2011) Inflammasome activation and IL-1beta target IL-1alpha for secretion as opposed to surface expression. Proceedings of the National Academy of Sciences of the United States of America 108 (44):18055-18060.
Keller M, Ruegg A, Werner S, & Beer HD (2008) Active caspase.1 is a regulator of unconventional protein secretion. Cell 132(5):818-831.
Gross O, et al. (2012) Inflammasome activators induce interleukin-1alpha secretion via distinct pathways with differential requirement for the protease function of caspase-1. Immunity 36(3):388-400.
Li Y, Arnold JM, Pampillo M, Babwah AV, & Peng T (2009) Taurine prevents cardiomyocyte death by inhibiting NADPH oxidase-mediated calpain activation. Free radical biology & medicine 46(1):51-61.
Sharma AK & Rohrer B (2007) Sustained elevation of intracellular cGMP causes oxidative stress triggering calpain-mediated apoptosis in photoreceptor degeneration. Current eye research 32(3):259-269.
Sorimachi H, Hata S, & Ono Y (2011) Impact of genetic insights into calpain biology. J Biochem 150(1):23-37.
Kim BH, et al. (2011) A family of IFN-gamrna-inducible 65-kD GTPases protects against bacterial infection. Science 332(6030):717-721.
Hartman ML & Kornfeld H (2011) Interactions between Naive and Infected Macrophages Reduce *Mycobacterium tuberculosis* Viability. PLoS One 6(11):e27972.
Thurston TL, Ryzhakov G, Bloor S, Von Muhlinen N, & Randow F (2009) The TBK1 adaptor and autophagy receptor NDP52 restricts the proliferation of ubiquitin-coated bacteria. Nat Immunol 10(11):1215-1221.
Dupont N, et al. (2009) Shigella phagocytic vacuolar membrane remnants participate in the cellular response to pathogen invasion and are regulated by autophagy. Cell Host Microbe 6(2):137-149.
Yoshikawa Y, et al. (2009) Listerie monocytogenes ActA-mediated escape from autophagic recognition. Nat Cell Biol 11(10):1233-1240.
Wild P, et al. (2011) Phosphorylation of the autophagy receptor optineurin restricts *Salmonella* growth. Science 333 (6039):228-233.
Orvedahl A, et al. (2010) Autophagy Protects against Sindbis Virus Infection of the Central Nervous System. Cell Host Microbe 7(2):115-127.
Cadwell K, et al. (2010) Virus-plus-susceptibility gene interaction determines Crohn's disease gene Atg16L1 phenotypes in intestine. Cell 141(7)1135-1145.
Saitoh T, et al. (2008) Loss of the autophagy protein Atg16L1 enhances endotoxin-induced IL-1beta production. Nature 456(7219):264-268.
Torrado E & Cooper AM (2010) IL-17 and Th17 cells in tuberculosis. Cytokine Growth Factor Rev 21(6):455-462.
Pedrosa J, et al. (2000) Neutrophils play a protective nonphagocytic role in systemic *Mycobacterium tuberculosis* infection of mice. infect Immun 68(2):577-583.
Seiler P, et al. (2003) Early granuloma formation after aerosol *Mycobacterium tuberculosis* infectibn is regulated by neutrophils via CXCR3-signaling chemokines. Eur J Immunol 33(10):2676-2686.
Khader SA, et al. (2007) IL-23 and IL-17 in the establishment of protective pulmonary CD4+ T cell responses after vaccination and during *Mycobacterium tuberculosis* challenge. Nat Immunol 8(4):369-377.

(56) References Cited

OTHER PUBLICATIONS

Desvignes L & Ernst JD (2009) Interferon-gamma-responsive nonhematopoietic cells regulate the immune response to *Mycobacterium tuberculosis*. Immunity. 31(6):974-985.
Nandi B & Behar SM (2011) Regulation of neutrophils by interferon-gamma limits lung inflammation during tuberculosis infection. The Journal of experimental medicine 208(11):2251-2262.
Cruz A, et al. (2010) Pathological role of interleukin 17 in mice subjected to repeated BCG vaccination after infection with *Mycobacterium tuberculosis*. The Journal of experimental medicine 207(8):1609-1616.
Berry MP, et al. (2010) An interferon-inducible neutrophil-driven blood transcriptional signature in human tuberculosis. Nature 466(7309):973-977.
Desvignes L, Wolf AJ, & Ernst JD (2012) Dynamic roles of type I and type II IFNs in early infection with *Mycobacterium tuberculosis*. J Immunol 188(12):6205-6215.
Harris J, et al. (2011).Autophagy controls IL-1{beta} secretion by targeting pro-IL-1{beta} for degradation. J Biol Chem.
Cadwell K, et al. (2008) A key role for autophagy and the autophagy gene Atg16I1 in mouse and human intestinal Paneth cells. Nature 456(7219):259-263.
Nunn P, et al. (2005) Tuberculosis control in the era of HIV. Nat Rev Immunol 5(10):819-826.
Mizushima N, Yamamoto A, Matsui M, Yoshimori T, & Ohsumi Y (2004) In vivo analysis of autophagy in response to nutrient starvation using transgenic mice expressing a fluorescent autophagosome marker. Mol Biol Cell 15(3):1101-1111.
Komatsu M, et al. (2007) Homeostatic levels of p62 control cytoplasmic inclusion body formation in autophagy-deficient mice. Cell 131(6):1149-1163.
Talaat AM, Lyons R, Howard ST, & Johnston SA (2004) The temporal expression profile of *Mycobacterium tuberculosis* infection in mice. Proceedings of the National Academy of Sciences of the United States of America 101 (13):4602-4607.
Zahrt TC & Deretic V (2001) *Mycobacterium tuberculosis* signal transduction system required for persistent infections. Proc Natl Acad Sci U S A 98(22):12706-12711.
Mizushima, N., Levine, B., Cuervo, A. M. & Klionsky, D. J. Autophagy fights disease through cellular self-digestion. Nature 451, 1069-1075 (2008).
Mizushima, N., Yoshimori, T. & Ohsumi, Y. The role of atg proteins in autophagosome formation. Annual review of cell and developmental biology 27, 107-132, doi:10.1146/annurev-cellbio-092910-154005 (2011).
Sarbassov, D. D., Ali, S. M. & Sabatini, D. M. Growing roles for the mTOR pathway. Curr Opin Cell Biol17, 596-603, doi:S0955-0674(05)00148-1 [pii] 10.1016/j.ceb.2005.09.009 (2005).
Laplante, M. & Sabatini, D. M. mTOR signaling in growth control and disease. Cell 149, 274-293;doi:10.1016/j.cell.2012.03.017 (2012).
Bar-Peled, L., Schweitzer, L. D., Zoncu, R. & Sabatini, D. M. Regulator Is a GEF for the Rag GTPasesthat Signal Amino Acid Levels to mTORC1. Cell 150, 1196-1208, doi:10.1016/j.cell.2012.07.032 (2012).
Neufeld, T. P. TOR-dependent control of autophagy: biting the hand that feeds. Curr Opin Cell Biol 22, 157-168, doi:10.1016/j.ceb.2009.11.005 (2010).
Scott, R. C., Schuldiner, O. & Neufeld, T. P. Role and regulation of starvation-induced autophagy in the *Drosophila* fat body. Dev Cell 7, 167-178, doi:10.1016/j.devcel.2004.07.009 (2004).
Rabinowitz, J. D. & White, E. Autophagy and metabolism. Science 330, 1344-1348, doi:10.1126/science.1193497 (2010).
Green, D. R., Galluzzi, L. & Kroemer, G. Mitochondria and the autophagy-inflammation-cell death axis in organismal aging. Science 333, 1109-1112, doi:10.1126/science.1201940 (2011).
Rubinsztein, D. C., Marino, G. & Kroemer, G. Autophagy and aging. Cell 146, 682-695, doi:10.1016/j. cell.2011.07.030 (2011).
Rubinsztein, D. C., Codogno, P. & Levine, B. Autophagy modulation as a potential therapeutic target for diverse diseases. Nature reviews. Drug discovery 11, 709-730, doi:10.1038/nrd3802 (2012).

Deretic, V. Autophagy in innate and adaptive immunity. Trends Immunol 26, 523-528, doi:S1471-4906(05)00206-1 [pii] 10.1016/j.it.2005.08.003 (2005).
Deretic, V. & Levine, B. Autophagy, immunity, and microbial adaptations. Cell Host Microbe 5, 527-549, doi: S1931-3128(09)00183-8 [pii] 10.1016/j.chom.2009.05.016 (2009).
Levine, B. & Deretic, V. Unveiling the roles of autophagy in innate and adaptive immunity. Nat Rev Immunol 7, 767-777 (2007).
Levine, B., Mizushima, N. & Virgin, H. W. Autophagy in immunity and inflammation. Nature 469, 323-335.
Deretic, V., Jiang, S. & Dupont, N. Autophagy intersections with conventional and unconventional secretion in tissue development, remodeling and inflammation. Trends in cell biology 22, 397-406,doi:10.1016/j.tcb.2012.04.008 (2012).
Deselm, C. J. et al. Autophagy proteins regulate the, secretory component of osteoclastic bone resorption. Dev Cell 21, 966-974, doi:10.1016/j.devcel.2011.08.016 (2011).
Ushio, H. et al. Crucial role for autophagy in degranulation of mast cells. The Journal of allergy and clinical immunology 127, 1267-1276 e1266, doi:10.1016/j.jaci.2010.12.1078 (2011).
Marino, G. et al. Autophagy is essential for mouse sense of balance. The Journal of clinical investigation 120, 2331-2344, doi:10.1172/JCI42601 (2010).
Ganesan, A. K. et al. Genome-wide siRNA-based functional genomics of pigmentation identifies novel genes and pathways that impact melanogenesis in human cells. PLoS genetics 4, e1000298,doi:10.1371/journal.pgen.1000298 (2008).
Narita, M. et al. Spatial coupling of mTOR and autophagy augments secretory phenotypes. Science 332, 966-970, doi:10.1126/science.1205407 (2011).
Manjithaya, R., Anjard, C., Loomis, W. F. & Subramani, S. Unconventional secretion of Pichia pastoris Acb1 is dependent on GRASP protein, peroxisomal functions, and autophagosome formation. J CellBiol 188,.537-546 (2010).
Bruns, C., McCaffery, J. M., Curwin, A. J., Duran, J. M. & Malhotra, V. Biogenesis of a novelcompartment for autophagosome-mediated unconventional protein secretion. J Cell Biol 195, 979-992,doi:10.1083/jcb.201106098 (2011).
Duran, J. M., Anjard, C., Stefan, C., Loomis, W. F. & Malhotra, V. Unconventional secretion of Acb1 is mediated by autophagosomes. J Cell Biol 188, 527-536 (2010).
Dupont, N. et al. Autophagy-based unconventional secretory pathway for extracellular delivery of IL-1beta. The EMBO journal 30, 4701-4711, doi:10.1038/emboj.2011.398 (2011).
Gee, H. Y., Noh, S. H., Tang, B. L., Kim, K. H. & Lee, M. G. Rescue of DeltaF508-CFTR Trafficking vies GRASP-Dependent Unconventional Secretion Pathway, Cell 146, 746-760, doi:10.1016/j.cell,2011.07.021 (2011).
Giuliani, F., Grieve, A. & Rabouille, C. Unconventional secretion: a stress on GRASP. Curr Opin CellBiol 23, 498-504, doi.10.1016/jceb.2011.04.005 (2011).
Nickel, W. & Rabouille, C. Mechanisms of regulated unconventional protein secretion. Nat Rev Mol Cell Biol 10, 148-155, doi:nrm2617 [pii]10.1038/nrm2617 (2009).
Rabouille, C., Malhotra, V. & Nickel, W. Diversity of unconventional protein secretion. Journal of CellScience In press (2012).
Cabral, M., Anjard, C., Malhotra, V., Loomis, W. F. & Kuspa, A. Unconventional secretion of AcbA in Dictyostelium discoideum through a vesicular intermediate. Eukaryot Cell 9, 1009-1017, doi:EC.00337-09 [pii] 10.1128/EC.00337-09 (2010).
Dinarello, C. A. Immunological and inflammatory functions of the interleukin-1 family. Annual review of immunology 27, 519-550, doi:10.1146/annurev.immunol.021908.132612 (2009).
Andersson, U. & Tracey, K. J. HMGB1 Is a Therapeutic Target for Sterile Inflammation and Infection. Annual review of immunology 29, 139-162, doi:10.1146/annurev-immunol-030409-101323 (2011).
Taguchi, A. et al. Blockade of RAGE-amphoterin signalling suppresses tumour growth and metastases. Nature 405, 354-360, doi:10,1038/35012626 (2000).
Tang, D. et al. HMGB1 release and redox regulates autophagy and apoptosis in cancer cells. Oncogene 29, 5299-5310, doi:onc2010261 [pii] 10.1038/onc.2010.261 (2010).

(56) References Cited

OTHER PUBLICATIONS

Rabinovich, G. A. & Croci, D. O. Regulatory circuits mediated by lectin-glycan interactions in autoimmunity and cancer. Immunity 36, 322-335, doi:10.1016/j.immuni.2012.03.004 (2012).
Vasta, G. R. et al. Galectins as self/non-self recognition receptors in innate and adaptive immunity: an unresolved paradox. Frontiers in immunology 3, 199, doi:10.3389/fimmu.2012.00199 (2012).
Vasta, G. R. Galectins as pattern recognition receptors: structure, function, and evolution. Advances in experimental medicine and biology 946, 21-36, doi:10.1007/978-1-4614-0106-3_2 (2012).
Starossom, S. C. et al. Galectin-1 deactivates classically activated microglia and protects from inflammation-induced neurodegeneration. Immunity 37, 249-263, doi:10,1016/j,immuni.2012.05.023 (2012).
Liu, F. T. & Rabinovich, G. A. Galectins as modulators of tumour progression. Nature reviews. Cancer 5, 29-41, doi:10.1038/nrc1527 (2005).
Thijssen, V. L. et al. Galectin-1 is essential in tumor angiogenesis and is a target for antiangiogenesis therapy. Proceedings of the National Academy of Sciences of the United States of America 103, 15975-15980, doi:10.1073/pnas.0603883103 (2006).
Michaud, M. et al. Autophagy-dependent anticancer immune responses induced by chemotherapeutic agents in mice. Science 334, 1573-1577, doi:10.1126/science.1208347 (2011).
Egan, D. F. et al. Phosphorylation of ULK1 (hATG1) by AMP-activated protein kinase connects energy sensing to mitophagy. Science 331, 456-461, doi:10.1126/science.1196371 (2011).
Nakatogawa, H., Ichimura, Y. & Ohsumi, Y. Atg8, a ubiquitin-like protein required for autophagosome formation, mediates membrane tethering and hemifusion. Cell 130, 165-178, doi:10.1016/j.cell. 2007.05.021 (2007).
Weidberg, H. et al. LC3 and GATE-16 N termini mediate membrane fusion processes required for autophagosome biogenesis. Dev Cell 20, 444-454, doi:10.1016/j.devcel.2011.02.006 (2011).
Nair, U. et al. SNARE proteins are required for macroautophagy. Cell 146, 290-302, doi:10.1016/j.cel1.2011.06.022 (2011).
Nakahira, K. et al. Autophagy proteins regulate innate immune responses by inhibiting the release of mitochondrial DNA mediated by the NALP3 inflammasome. Nature immunology 12, 222-230, doi:10.1038/ni.1980 (2011).
Martinon, F., Petrilli, V., Mayor, A., Tardivel, A. & Tschopp, J. Gout-associated uric acid crystals activate the NALP3 inflammasome. Nature 440, 237-241 (2006).
Sun, Y., Bilan, P. J., Liu, Z. & Klip, A. Rab8A and Rab13 are activated by insulin and regulate GLUT4 translocation in muscle cells. Proceedings of the National Academy of Sciences of the United States of America 107, 19909-19914, doi:10.1073/pnas. 1009523107 (2010).
Moritz, O. L. et al. Mutant rab8 Impairs docking and fusion of rhodopsin-bearing post-Golgi membranes and causes cell death of transgenic Xenopus rods. Mol Biol Cell 12, 2341-2351. (2001).
Bravo-Cordero, J. J. et al. MT1-MMP proinvasive activity is regulated by a novel Rab8-dependent exocytic pathway. The EMBO journal 26, 1499-1510, doi:10.1038/sj.emboj.7601606 (2007).
Nachury, M. V. et al. A core complex of BBS proteins cooperates with the GTPase Rab8 to promote ciliary membrane biogenesis. Cell 129, 1201-1213, doi:10.1016/j.cell.2007.03.053 (2007).
Bryant, D. M. et al. A molecular network for de novo generation of the apical surface and lumen. Nature cell biology 12, 1035-1045, doi:10.1038/ncb2106 (2010).
Mazelova, J., Ransom, N., Astuto-Gribble, L., Wilson, M. C. & Deretic, D. Syntaxin 3 and SNAP-25 pairing, regulated by omega-3 docosahexaenoic acid, controls the delivery of rhodopsin for the biogenesis of cilia-derived sensory organelles, the rod outer segments. J Cell Sci 122, 2003-2013, doi:jcs.039982 [pii] 10.1242/jcs. 039982 (2009).
Bodemann, B. O. et al. RalB and the Exocyst Mediate the Cellular Starvation Response by Direct Activation of Autophagosome Assembly. Cell 144, 253-267, doi:S0092-8674(10)01436-4 [pii]10.1016/ j.cell.2010.12.018 (2011).

Kinseth, M. A. et al. The Golgi-associated protein GRASP is required for unconventional protein secretion during development. Cell 130, 524-534, doi:S0092-8674(07)00826-4 [pii] 10.1016/j.cell. 2007.06.029 (2007).
Mizushima, N., Yoshimori, T. & Levine, B. Methods in mammalian autophagy research. Cell 140, 313-326 (2010).
Kimura, S., Noda, T. & Yoshimori, T. Dissection of the autophagosome maturation process by a novel reporter protein, tandem fluorescent-tagged LC3. Autophagy 3, 452-460 (2007).
Tang, D. et al. Endogenous HMGB1 regulates autophagy. J Cell Biol 190, 881-892; doi:jcb.200911078 [pii] 10.1083/jcb.200911078 (2010).
Singh, S. B. et al. Human IRGM regulates autophagy and cell-autonomous immunity functions through mitochondria. Nat Cell Biol 12, 1154-1165, doi:ncb2119 [pii] 10.1038/ncb2119 (2010).
Keller, M., Ruegg, A., Werner, S. & Beer, H. D. Active caspase-1 is a regulator of unconventional protein secretion. Cell 132, 818-831, doi:10.1016/j.cell.2007.12.040 (2008).
Lamkanfi, M. Emerging inflammasome effector mechanisms. Nature reviews. Immunology 11, 213-220, doi:10.1038/nri2936 (2011).
Lamkanfi, M. et al. Inflammasome-dependent release of the alarmin HMGB1 in endotoxemia. Journal of immunology 185, 4385-4392, doi:10.4049/jimmunol.1000803 (2010).
Willingham, S. B. et al. NLRP3 (NALP3, Cryopyrin) facilitates in vivo caspase-1 activation, necrosis,and HMGB1 release via inflammasome-dependent and -independent pathways. Journal of immunology183, 2008-2015, doi:10.4049/jimmunol.0900138 (2009).
Axe, E. L. et al. Autophagosome formation from membrane compartments enriched in phosphatidylinositol 3-phosphate and dynamically connected to the endoplasmic reticulum. J Cell Biol182, 685-701 (2008).
Hayashi-Nishino, M. et al. A subdomain of the endoplasmic reticulum forms a cradle for autophagosome formation. Nature cell biology 11, 1433-1437, doi:10.1038/ncb1991 (2009).
Moreau, K., Ravikumar, B., Renna, M., Puri, C. & Rubinsztein, D. C. Autophagosome precursor maturation requires homotypic fusion. Cell 146, 303-317, doi:10.1016/j.cell.2011.06.023 (2011).
Hailey, D. W. & Lippincott-Schwartz, J. Using photoactivatable proteins to monitor autophagosome lifetime. Methods Enzymol 452, 25-45, doi:S0076-6879(08)03603-3 [pii] 10.1016/S0076-6879(08)03603-3 (2009).
Young, A. R. et al. Starvation and ULK1-dependent cycling of mammalian Atg9 between the TGN and endosomes. J Cell Sci 119, 3888-3900 (2006).
Yen, W. L. et al. The conserved oligomeric Golgi complex is involved in double-membrane vesicle formation during autophagy. J Cell Biol 188, 101-114, doi:jcb.200904075 [pii] 10.1083/jcb. 200904075 (2010).
Yamamoto, H. et al. Atg9 vesicles are an important membrane source during early steps of autophagosome formation. J Cell Biol 198, 219-233, doi:10.1083/jcb.201202061 (2012).
Lum, J. J., Deberardinis, R. J. & Thompson, C. B. Autophagy in metazoans: cell survival in the land of plenty. Nat Rev Mol Cell Biol 6, 439.448 (2005).
Bernales, S., McDonald, K. L. & Walter, P. Autophagy counterbalances endoplasmic reticulum expansion during the unfolded protein response. PLoS Biol 4, e423 (2006).
Schotman, H., Karhinen, L. & Rabouille, C. dGRASP-mediated noncanonical integrin secretion is required for *Drosophila epithelial* remodeling. Dev Cell 14, 171-182, doi:10.1016/j.devcel.2007.12. 006 (2008).
Glick, B. S. & Nakano, A. Membrane traffic within the Golgi apparatus. Annual review of cell and developmental biology 25, 113-132, doi:10.1146/annurev.cellbio.24.110707.175421 (2009).
Lorente-Rodriguez, A. & Barlowe, C. Entry and exit mechanisms at the cis-face of the Golgi complex. Cold Spring Harbor perspectives in biology 3, doi:10.1101/cshperspect.a005207 (2011).
Truschel, S. T., Zhang, M., Bachert, C., Macbeth, M. R. & Linstedt, A. D. Allosteric regulation of GRASP protein-dependent Golgi membrane tethering by mitotic phosphorylation. The Journal of biological chemistry 287, 19870-19875, doi:10.1074/jbc.M111. 326256 (2012).

(56) References Cited

OTHER PUBLICATIONS

Jarvela, T. & Linstedt, A. Golgi GRASPs: moonlighting membrane tethers. Cell Health and Cytoskeleton 4, 37-47 (2012).
Roberts, E. A. & Deretic, V. Autophagic proteolysis of long-lived proteins in nonliver cells. Methods Mol Biol 445, 111-117 (2008).
Ponpuak, M., Delgado, M. A., Elmaoued, R. A. & Deretic, V. Monitoring autophagy during *Mycobacterium tuberculosis* infection. Methods Enzymol 452, 345-361, doi:S0076-6879(08)03621-5 [pii] 10.1016/S0076-6879(08)03621-5 (2009).
Pilli, M. et al. TBK-1 Promotes Autophagy-Mediated Antimicrobial Defense by Controlling Autophagosome Maturation. Immunity 37, 223-234, doi:10.1016/j.immuni.2012.04.015 (2012).
Ponpuak, M. et al. Delivery of cytosolic components by autophagic adaptor protein p62 endows autophagosomes with unique antimicrobial properties. Immunity 32, 329-341 (2010).
Miller, J. C. et al. A TALE nuclease architecture for efficient genome editing. Nature biotechnology 29,143-148, doi:10.1038/nbt.1755 (2011).
Tang, H. W. et al. Atg1-mediated myosin II activation regulates autophagosome formation during starvation-induced autophagy. The EMBO journal 30, 636-651, doi:10.1038/emboj.2010.338 (2011).
Soderberg, O. et al. Direct observation of individual endogenous protein complexes in situ by proximity ligation. Nature methods 3, 995-1000, doi:10.1038/nmeth947 (2006).
Ishihara, N. et al. Autophagosome requires specific early Sec proteins for its formation and NSF/SNARE for vacuolar fusion. Mol Biol Cell 12, 3690-3702 (2001).
Proikas-Cezanne, T. et al. WIPI-1alpha (WIPI49), a member of the novel 7-bladed WIPI protein family,is aberrantly expressed in human cancer and is linked to starvation-induced autophagy. Oncogene 23,9314-9325 (2004).
Wei, Y., Pattingre, S., Sinha, S., Bassik, M. & Levine, B. JNK1-mediated phosphorylation of Bcl-2 regulates starvation-induced autophagy. Mol Cell 30, 678-688 (2008).
Urano, F. et al. Coupling of stress in the ER to activation of JNK protein kinases by transmembrane protein kinase IRE1. Science 287, 664-666 (2000).
Lu, B. et al. Novel role of PKR in inflamasome activation and HMGB1 release. Nature 488, 670-674,doi:10.1038/nature11290 (2012).
Talloczy, Z. et al. Regulation of starvation- and virus-induced autophagy by the elF2alpha kinase signaling pathway. Proc Natl Acad Sci U S A 99, 190-195 (2002).
Tsukamoto, S. et al. Autophagy is essential for preimplantation development of mouse embryos. Science 321, 117-120 (2008).
Lynch-Day, M. A. et al. Trs85 directs a Ypt1 GEF, TRAPPIII, to the phagophore to promote autophagy. Proc Natl Acad Sci U S A 107, 7811-7816, doi:1000063107 [pii] 10.1073/pnas.1000063107 (2010).
Meiling-Wesse, K. et al. Trs85 (Gsg1), a component of the TRAPP complexes, is required for the organization of the preautophagosomal structure during selective autophagy via the Cvt pathway. J Biol Chem 280, 33669-33678 (2005).
Weidberg, H. et al. LC3 and GATE-16/GABARAP subfamilies are both essential yet act differently in autophagosome biogenesis. The EMBO journal 29, 1792-1802, doi:10.1038/emboj.2010.74 (2010).
Wild, P. et al. Phosphorylation of the autophagy receptor optineurin restricts Salmonella growth. Science 333, 228-233, doi:10.1126/science.1205405 (2011).
Thurston, T. L., Wandel, M. P., Von Muhlinen, N., Foeglein, A. & Randow, F. Galectin 8 targets damaged vesicles for autophagy to defend cells against bacterial invasion. Nature 482, 414-418, doi:10.1038/nature10744 (2012).
Kirkin, V. et al. A role for NBR1 in autophagosomal degradation of ubiquitinated substrates. Mol Cell 33, 505-516 (2009).
Johansen, T. & Lamark, T. Selective autophagy mediated by autophagic adapter proteins. Autophagy 7, 279-296 (2011).
Matsumoto, G., Wada, K., Okuno, M., Kurosawa, M. & Nukina, N. Serine 403 Phosphorylation of p62/SQSTM1 Regulates Selective Autophagic Clearance of Ubiquitinated Proteins. Molecular Cell 44, 279-289 (2011).

Stenmark, H. Rab GTPases as coordinators of vesicle traffic. Nat Rev Mol Cell Biol 10, 513-525, doi:nrm2728 [pii] 10.1038/nrm2728 (2009).
Rezaie, T. et al. Adult-onset primary open-angle glaucoma caused by mutations in optineurin. Science 295, 1077-1079, doi:10.1126/science.1066901 (2002).
Morton, S., Hesson, L., Peggie, M. & Cohen, P. Enhanced binding of TBK1 by an optineurin mutant that causes a familial form of primary open angle glaucoma. FEBS Lett 582,997-1002, doi:S0014-5793(08)00160-9 [pii] 10.1016/j.febslet.2008.02.047 (2008).
Rusten, T. E., Vaccari, T. & Stenmark, H. Shaping development with ESCRTs. Nature cell biology 14,38-45, doi:10.1038/ncb2381 (2012).
Munson, M. & Novick, P. The exocyst defrocked, a framework of rods revealed. Nature structural &molecular biology 13, 577-581, doi:10.1038/nsmb1097 (2006).
Ishikawa, H., Ma, Z. & Barber, G. N. STING regulates intracellular DNA-mediated, type I interferondependent innate immunity. Nature 461, 788-792, doi:10.1038/nature08476 (2009).
Jia, Jingyue et al.; Galectins Control MTOR and AMPK in Response to Lysosomal Damage to Induce Autophagy. Autophagy 2018, DOI: 10.1080/15548627.2018.1505155.
Choi, Seong Won et al.; Ambroxol induces autophagy and potentiates Rifampicin antimycobacterial activity. Antimicrob. Agents Chemother.2018; DOI: 10.1128/AAC.01019-18.
Deretic, Vojo et al.; Autophagy, Inflammation, and Metabolism (AIM) Center of biomedical Research Excellence: supporting the next generation of autophagy researchers and fostering international collaborations. Autophagy 2018, vol. 14, No. 6, pp. 925-929. DOI: 10.1080/15548627.2018.1465784.
Bissa, Bhawana and Deretic, Vojo.; Autophagosome Formation: Cutting the Gordian Knot at the ER. Current Biology Apr. 23, 2018, vol. 28, pp. R342-R366. DOI:10.1016/J.CUB.2018.03.015.
Jia, Jingyue et al.; Galectins Control mTOR in Response to Endomembrane Damage. Molecular Cell Apr. 5, 2018, vol. 70, pp. 120-135. DOI: 10.1016/j.molcel.2018.03.009.
Claude-Taupin, Aurore et al.; Role of autophagy in IL-1-beta export and releasee from cells. Seminars in Cell & Developmental Biology 2018; DOI: 10.1016/j.semcdb.2018.03.012.
Kumar, Suresh et al.; Mechanism of Stx17 recruitment to autophagosomes via IRGM and mammalian Atg8 proteins. J. Cell. Biol. Aug 9, 2018; vol. 217, No. 3, pp. 997-1013. DOI: 10.1083/jcb.2017080239.
Castillo, Eliseo F. et al.; Orchestration of epithelial-derived cytokines and innate immune cells in allergic airway inflammation. Cytokine and Growth Factor Reviews 2018; vol. 39, pp. 19-25. Available online Nov. 21, 2017 DOI: 10.1016/j.cyto.gfr.2017.11.004.
Deretic, Vojo & Klionsky, Daniel J.; Autophagy and Inflammation: A special review issue. Autophagy Jan. 29, 2018; vol. 14, No. 2, pp. 179-180. DOI: 10.1080/15548627.2017.1412229.
Deretic, Vojo & Levine, Beth; Autophagy balances inflammation in innate immunity. Autophagy 2018; vol. 14, No. 2, pp. 243-251 DOI: 10.1080/15548627.2017.1402992 Accepted author version available online Nov. 22, 2018; published online Jan. 17, 2018.
Claude-Taupin, Aurore et al.; Autophagy's secret life: secretion instead of degradation. Essays in Biochemistry Dec. 12, 2012; vol. 61, pp. 637-647. DOI: 10/1042/EBC20170024.
Galluzzi, Lorenzo et al.; Molecular definitions of autophagy andrelated processes. The EMBO Journal Jun. 8, 2017; vol. 36, pp. 1811-1836. DOI: 10.15252/embj..201796697.
Kimura, Tomonori et al.; Cellular and Molecular Mechanism for Secretory Autophagy. Autophagy 2017; vol. 13, No. 6, pp. 1084-1085. DOI: 10.1080/15548627.2017.1307486.
Kumar, Suresh et al.; Galectins and TRIMs directly interact andorchestrate autophagic respoonse to endomembrane damage. Autophagy 2017; vol. 13, No. 6, pp. 1086-1087 DOI: 10.1080/15548627.2017.1307487.
Kimura, Tomonori et al.; trim-Directed Selective Autophagy Regulates Immune Activation. autophagy 2017; vol. 13, No. 5, pp. 989-990 DOI: 10.1080/15548627.2016.1154254.
Mandell, Michael A. et al.; Correction: TRIM17 contributes to autophagy of midbodies while actively sparing other targets from degradation. J. Cell Sci. 2017; vol. 130, p. 1194 DOI: 10.1242/jcs.202499.

(56) References Cited

OTHER PUBLICATIONS

Kimura, Tomonori et al.; Dedicated SNAREs and specialized TRIM cargo receptors mediate secretory autophagy. The EMBO Journal 2017; vol. 36, pp. 42-60.

Deretic, Vojo; Autophagy in leukocytes and other cells: mechanisms, subsystem organization, selectivity, and links to innate immunity. Journal of Leukocyte Biology Nov. 2016; vol. 100, pp. 969-978 DOI: 10.1189/jlb.4MR0216-0798.

Chauhan, Santosh et al.; TRIMs and Galectins globally cooperate and TRIM16 and Galectin-3 co-direct autophagy ini endomembrane damage homeostasis. Dev. Cell. Oct. 10, 2016; vol 39, No. 1, pp. 13-27 DOI: 10.1016/j.devcel.2016.08.003.

* cited by examiner

Figure 25

| Potential Substrates | Signal peptide | Score |
|---|---|---|
| Vimentin | No | -0.2 |
| Galectin 1 | No | -0.1 |
| Galectin 3 | No | -0.1 |
| IL-1β | Yes | -0.4 |
| Ferritin | No | -0.4 |
| IGF | No | -0.1 |
| Annexine C2 | Yes | -0.7 |
| Osirin | No | -0.2 |
| TIMP-1 | No | variable |
| Cathepsin B | Yes | -0.5 |
| Cathepsin L | Yes | -0.4 |
| Cathepsin Z | Yes | -0.4 |
| Thioredoxin | No | -0.1 |
| Peroxiredoxin5 | No | -0.2 |

TREATMENT OF AUTOPHAGY-BASED DISORDERS AND RELATED PHARMACEUTICAL COMPOSITIONS, DIAGNOSTIC AND SCREENING ASSAYS AND KITS

This application is a divisional application of United States national phase patent application Ser. No. 14/434,931 filed on Apr. 10, 2015, which is based on international patent application number PCT/US2013/064946 filed on Oct. 15, 2013, which claims the benefit of priority from two United States provisional patent applications, U.S. 61/713,919 and U.S. 61/713,843, both filed on Oct. 15, 2012. These four priority applications are hereby incorporated by reference in their entirety herein.

RELATED APPLICATIONS AND GOVERNMENT SUPPORT

This invention was made with government support under grant numbers R01 AI069345 and R01 AI042999 awarded by the National Institutes of Health (NIH). The government has certain rights in the invention.

FIELD OF THE INVENTION

In one embodiment, the invention provides a method of treating a subject suffering from a *Mycobacterium* infection by administering to the subject a therapeutically-effective amount of a degradative autophagy agonist or a secretory autophagy antagonist.

In another embodiment, the invention provides a method of treating a subject suffering from one or more diseases selected from the group consisting of a *Mycobacterium* infection, an inflammatory disorder, an immune disorder, a cancer and a neurodegenerative disorder by administering to the subject a therapeutically-effective amount of a TBK-1 antagonist (e.g. BX795 or amlexanox).

Related pharmaceutical compositions, diagnostic and screening assays and kits are also provided.

BACKGROUND OF THE INVENTION

Autophagy is a fundamental cell biological process (1) with impact on aging, development, cancer, neurodegeneration, myodegeneration, and metabolic disorders (2), idiopathic inflammatory diseases and infection and immunity (3). Much of the physiological effects of autophagy are the result of degradative activities of autophagy (1), although biogenesis and secretory roles (4-6) of autophagy are beginning to be recognized (7). The execution of autophagy depends on factors collectively termed Atg such as Atg5 (1) and Beclin 1 (Atg6) (8) whereas regulation of autophagy responds to various inputs via mTOR, including presence of microbes (9), TAB2/3-TAK1-IKK signaling axis (10), and processes downstream of pattern recognition receptors and immune cytokine activation (3, 11-13).

In the context of its immunological functions, autophagy acts in four principal ways (14): (i) Autophagy cooperates with conventional PRRs, such as TLRs, RLRs, and NLRs, and it plays the role of both a regulator (11, 12, 15, 16) and an effector of PRR signaling (17-19). (ii) Autophagy affects presentation of cytosolic antigens in the context of MHC II molecules (20) in T cell development, differentiation, polarization and homeostasis (21, 22). (iii) Most recently, autophagy has been shown to contribute to both the negative (6, 7, 23-25) and positive regulation (6, 7) of unconventional secretion of the leaderless cytosolic proteins known as alarmins such as IL-1β and HMGB1. (iv) Autophagy can capture and eliminate intracellular microbes including *M. tuberculosis* (17, 26-29) as one of the first two bacterial species (26, 30) to be recognized as targets for autophagic removal. This has been recently shown to depend on a recognition and capture by adaptors that represent a specialized subset of pattern recognition receptors (PRR) termed sequestosome-like receptors (SLRs) (31).

*M. tuberculosis* is one of the first microbes recognized as being subject to elimination by immunological autophagy in ex vivo systems in murine and human macrophages (17, 22, 26, 27, 29). Although it has been shown that macrophages from Atg5$^{fl/fl}$ r LysM-Cre$^+$ mice defective for autophagy in myeloid lineage fail to control *M. tuberculosis* H37Rv (32) the in vivo role of autophagy in control of *M. tuberculosis* has not been reported. Given the compelling reasons for testing whether autophagy matters in control of *M. tuberculosis* in vivo, here we used a mouse model of tuberculosis and employed transgenic mice deficient in Atg5 in the myeloid lineage including macrophages, a cell type parasitized by *M. tuberculosis* (33). We demonstrate that autophagy controls tuberculosis infection in vivo and uncover a parallel role of autophagy in preventing excessive inflammatory reactions in the host.

The notion of autophagy as a purely degradative pathway was recently challenged by the emergence of reports of the secretory function of autophagy by three independent groups on the secretion of Acb1 in yeast (25A,26A,32A) and IL-1β secretion in mammalian cells (17A,27A). These new developments assign to autophagy a non-degradative function manifested as unconventional protein secretion (FIG. 3A). Furthermore, it has become apparent that autophagy even more broadly intersects with protein trafficking to include effects on the constitutive biosynthetic pathway (23A), regulated exocytosis (19A), and alternative sorting of integral membrane proteins to the plasma membrane (28A).

SUMMARY OF THE INVENTION

We have characterized a conditional gene knockout mouse model (Atg5$^{fl/fl}$ LysM-Cre) with a well documented Atg5 defect in macrophages and infected these mice aerogeneously with the virulent *M. tuberculosis* strain H37Rv. An increase in bacterial burden in the lungs and increased lung pathology was observed in Atg5$^{fl/fl}$ LysM-Cre$^+$ compared to Atg5$^{fl/fl}$ LysM-Cre$^+$ littermates (FIG. 1P, panel A). With higher doses of *M. tuberculosis* Atg5$^{fl/fl}$ LysM-Cre$^+$ mice succumbed sooner to infection. These findings demonstrate for the first time that autophagy is important for control of *Mycobacterium* infections such as *M. tuberculosis* in vivo.

As explained hereinafter, we have also identified and proposed a variety of secretory autophagy-related biomarkers and cellular processes that enable us to utilize the machinery and mechanisms of autophagy-dependent unconventional protein secretion in mammalian cells in novel therapeutic, diagnostic and screening methods.

In one embodiment, our invention provides a method of treating a subject suffering from a *Mycobacterium* infection by administering to the subject a therapeutically-effective amount of a degradative autophagy agonist.

In another embodiment, the invention provides a method of treating a subject suffering from a *Mycobacterium* infection by administering to the subject a therapeutically-effective amount of a secretory autophagy antagonist (e.g. an IL-1 receptor (IL-1RA) antagonist, an IL-1β antagonist, an IL-18 (IL-1F4) antagonist, an IL-33 antagonist, a galectin antagonist (antagonist of any one or more of the human galectins galectin-1, galectin-2, galectin-3, galectin-4, galectin-7, galectin-8, galectin-9, galectin-10, galectin-12 and galectin-13), a TSG101 antagonist, a HMGB1 antagonist, a Rab GTPase antagonist or a GRASP55 or GRASP65 antagonist). In certain preferred embodiments, the IL-1RA antagonist and IL-1β antagonist are anti-IL-1RA antibodies, IL-1β antibodies or Anakinra; the TSG101 antagonist is a TSG101 siRNA; the HMGB1 antagonist is selected from the group consisting of anti-HMGB1 antibody, ethyl pyruvate, a high mobility group box (HMGB1) peptide or a biologically active fragment thereof, an antibody to HMGB or an antigen-binding fragment thereof, an HMGB small molecule antagonist, an antibody to TLR2 or an antigen-binding fragment thereof, a soluble TLR2 polypeptide, an antibody to RAGE or an antigen-binding fragment thereof, a soluble RAGE polypeptide and a RAGE small molecule antagonist; the Rab GTPase antagonist is 2-(benzoylcarbamothioylamino)-5,5-dimethyl-4,7-dihydrothieno[2,3-c]pyran-3-carboxylic acid and the GRASP55 or GRASP65 antagonist is a GRASP55 or GRASP65 siRNA. In another preferred embodiment of this method of treatment, the HMGB1 antagonist is glycyrrhizin. In certain embodiments, the galectin antagonist/inhibitor is a galactomannan based carbohydrate such as GM-CT-01, GR-MD-02 (Galectin Therapeutics, Inc., as described in U.S. Pat. No. 8,236,780 which is incorporated by reference herein), GCS-100 (CAS No. 531508-98-2) (a pectin have multiple side-branches containing the sugar β-galactose), taloside (a C-2 epimer of galactose) or a pectin (apple, rhubarb, okra, onion), among others. One or more of the above-described antagonists also may be used in the treatment of a number of disease states and/or conditions such as sepsis, inflammatory disease states and disorders and cancer as described herein.

In another embodiment, the invention provides a method of treating a subject suffering from one or more diseases selected from the group consisting of a *Mycobacterium* infection, an inflammatory disorder, an immune disorder, a cancer and a neurodegenerative disorder, the method comprising administering a therapeutically-effective amount of a TBK-1 antagonist to the subject. In a preferred embodiment, the TBK-1 antagonist is BX795 or amlexanox.

In another embodiment, the present invention is directed to the treatment or prophylaxis (reducing the likelihood) of a disease state or condition modulated by secretory autophagy including sepsis, an inflammatory disease state (as otherwise described herein) and cancer in a patient in need comprising administering an effective amount of agent which modulates (inhibits and/or promotes/induces) secretory autophagy to said patient in need. The disease state or condition may be modulated by any one or more of $HMGB_1$ (sepsis, inflammatory disease states and disorders and cancer, often by inhibition of $HMGB_1$), IL-1β (sepsis, cancer and inflammatory disease states and disorders, often by inhibition of IL-1β), IL-18 (sepsis, inflammatory disease states and disorders and cancer, often by inhibition of IL-18 using IL-18 binding protein IL-18BP, antibodies against IL-18 including humanized antibodies or a mutein or fused protein thereof as inhibitors), IL-33 (sepsis, inflammatory disease and cancer often by inhibition the release of IL-33, or in the case of cancer, both inhibition and inducing release of IL-33 by ST2 Inhibitor (ST2 protein) or IL-33 inhibitor or antibodies which bind to IL-33), or one or more galectin inhibitor/antagonists described above. It is noted that in the case of sepsis and inflammatory disease states and disorders and conditions, the inhibition (including the secretion of the modulator), rather than the induction or promotion of the secretion of one or more of the above modulators is often therapeutic. In the case of cancer therapy, the inhibition of one or more of the above-modulators, including its secretion from cells, may provide an anticancer benefit, and in certain instances, the induction or promotion of secretion of one or more of the above-modulators may prove therapeutically beneficial for the treatment of cancer.

In another embodiment, the invention provides a method of identifying a protein that is a substrate for secretory autophagy (i.e. an autophagic secretome), the method comprising:
(a) providing a sample of Atg5-proficient cells and isogenic Atg5-deficient cells; and
(b) subjecting the sample to subtractive analysis by inducing autophagy in the sample and identifying protein entities released into supernatants from Atg5-proficient cells but not from isogenic Atg5-deficient cells;
wherein protein entities released into supernatants from Atg5-proficient cells are identified as substrates for secretory autophagy.

In another embodiment, the invention provides a method of identifying a protein that is a substrate for secretory autophagy (i.e. an autophagic secretome), the method comprising:
(a) providing a sample of Atg5-proficient cells and isogenic Atg5-deficient cells; and
(b) subjecting the sample to subtractive analysis by: (1) inducing autophagy in primary macrophages of the sample for a period of time selected to avoid nonspecific leakage of cytosolic proteins from cells; and (2) identifying protein entities released into supernatants from Atg5-proficient cells but not from isogenic Atg5-deficient cells;
wherein protein entities released into supernatants from Atg5-proficient cells are identified as substrates for secretory autophagy.

In another embodiment, the invention provides a method of determining whether a composition is a secretory autophagy antagonist, the method comprising contacting a eukaryotic cell sample with the composition, measuring cellular expression levels of one or more biomarkers selected from the group consisting of vimentin, galectin-1, galectin-3 (or other galectins such as galectin-2, -4, -7, -8, -9, -10, -12 and -13), ASC (an inflammasome component), ferritin and thioredoxin, and comparing measured cellular expression levels of the one or more biomarkers with expression levels of corresponding biomarkers in a control eukaryotic cell sample, wherein reduced expression levels of the one or more biomarkers when compared to control expression levels indicates that the composition is a secretory autophagy antagonist. In a preferred embodiment of this screening method, the cells are human primary peripheral blood monocyte-derived macrophages.

In another embodiment, the invention provides a method of determining whether a composition is a secretory autophagy antagonist, the method comprising contacting a eukaryotic cell sample with the composition, measuring cellular expression levels of one or more biomarkers selected from the group consisting of Atg8 (LC3A, B and C, and GABARAP, GABARAPL1 and L2), Rab8a, Atg9, FIP200, VMP1, WIPIs 91 and DFCP-1 69, and comparing measured cellular expression levels of the one or more biomarkers with corresponding expression levels of the biomarkers in a control eukaryotic cell sample, wherein reduced expression levels of the one or more biomarkers when compared to control expression levels indicates that the composition is a secretory autophagy antagonist. In a preferred embodiment of this screening method, the cells are human primary peripheral blood monocyte-derived macrophages.

In another embodiment, the invention provides a method of determining whether a composition is a secretory autophagy antagonist, the method comprising contacting a eukaryotic cell sample with the composition, measuring cellular expression levels of at least one biomarkers selected from the group consisting of IL-1RA, IL-1β, IL-18 (IL-1F4), IL-33, a galectin (galectin-1, -2, -3, -4, -7, -8, -9, -10, -12 and -13), TSG101, HMGB1, a Rab GTPase, GRASP55 and GRASP65 and comparing cellular expression levels of the at least one biomarkers with expression levels of corresponding biomarkers in a control eukaryotic cell sample, wherein reduced measured expression levels of the at least one biomarkers when compared to control expression levels indicates that the composition is a secretory autophagy antagonist.

In still another embodiment, the invention provides a method of determining whether a subject suffers from, or is likely to develop, one or more autophagy-related disorders selected from the group consisting of an inflammatory disorder, an immune disorder, a cancer and a neurodegenerative disorder (as described herein), the method comprising measuring expression levels in a cell sample obtained from the subject of one or more biomarkers selected from the group consisting of vimentin, galectin-1, galectin-3 (other galectins including galectin-2, -4, -7, -8, -9, -10, -12 and -13), ASC, ferritin and thioredoxin and comparing measured expression levels of the one or more biomarkers to expression levels of corresponding biomarkers in a control cell sample, wherein elevated expression levels of the one or more biomarkers when compared to control levels indicates that the subject suffers from, or is likely to develop, one or more of the autophagy-related disorders.

In still another embodiment, the invention provides a method of determining whether a subject suffers from, or is likely to develop, a *Mycobacterium* infection, the method comprising measuring expression levels in a cell sample obtained from the subject of one or more biomarkers selected from the group consisting of Atg8 (LC3A, B and C, and GABARAP, GABARAPL1 and L2), Rab8a, Atg9, FIP200, VMP1, WIPIs 91, DFCP-1 69, IL-1RA, IL-1β, IL-18 (IL-1F4), IL-33, a galectin (galectin-1, -2, -3, -4, -7, -8, -9, -10, -12 and -13), TSG101, HMGB1, a Rab GTPase, GRASP55 and GRASP65 and comparing measured expression levels of the one or more biomarkers to expression levels of corresponding biomarkers in a control cell sample, wherein elevated expression levels of the one or more biomarkers when compared to control levels indicates that the subject suffers from, or is likely to develop, one or more of the autophagy-related disorders.

In still another embodiment, the invention provides a pharmaceutical composition comprising an amount of a TBK-1 antagonist which is effective in treating a *Mycobacterium* infection and, optionally, a pharmaceutically-acceptable excipient.

In one particular embodiment, a particular assay is provided (see FIGS. 13A and 13B) comprising a population of two distinct cells, the first population of cells expressing a sequestome-like receptor (SLR) and a galectin-GFP (green fluorescent protein) fusion protein (which provides a green fluorescent signal in the first population of cells), the galectin-GFP fusion protein binding to said SLR and being secreted from said first population of cells, especially in the presence of an autophagy secretion inducer. The second population of cells express red fluorescent protein and galectin receptors on their surfaces which concentrate and take up (by endocytosis) galectin bound on the surface of the cells. The two populations of cells, when mixed together in the absence of an inhibitor or promoter of autophagy secretion will provide a mixture of green cells and red cells (and either no red fluorescent cells or relatively few red fluorescent cells which also express green fluorescent protein from galectin-GFP being taken up under control conditions) from the two populations of cells (control). In the presence of a compound which is an inducer of autophagy secretion, the fluorescence emitted from the two populations of cells reflect the induction of autophagy secretion (as evidenced by a decrease in green fluorescence emanating from the first population of cells and an increase in green fluorescence emanating from the second population of cells). In the presence of an inhibitor of autophagy, any green fluorescence which is emitted from the first population of cells may be increased and any green fluorescence emitted from the second population of cells which occurs naturally (control) between the cells will be reduced, evidencing the compound as a potential inhibitor of autophagy. In certain embodiments, the release of galectin-GFP from the first population of cells under control conditions (i.e. in the absence of an inhibitor or inducer of autophagy secretion) will be sufficiently high so that the exposure of the cells to an inhibitor of autophagy secretion will increase the green fluorescence emitted from the first population of cells and reduce the green fluorescence emitted by the second population of cells compared to control, and exposure to an inducer of autophagy secretion will decrease the green fluorescence emitted from the first population of cells and increase the green fluorescence emitted from the second population of cells. Through use of the above-described assays system, an inducer or inhibitor of autophagy (galectin) may be readily provided. The same system may be readily adapted for other autophagy modulators described herein. Methods of using the above-described assay(s) to identify a compound of unknown activity as an inhibitor or inducer of autophagy secretion represent additional embodiments of the present invention. The method can be readily adapted for use in flow cytometry. A kit based upon the above-described assay comprises a first cell population which expresses sequestome-like receptor (SLR) and galectin-GFP fusion protein and a second cell population which expresses red fluorescent protein and galectin surface receptors which concentrate and take up galectin into the cell. While any eukaryotic cell may be readily engineered to provide a first population of cells and a second population of cells, preferred cells are human engineered cells including engineered HeLa cells.

It is noted that any galectin-GFP fusion protein in the above-described assays and methods, including galectin-1, galectin-2, galectin-3, galectin-4, galectin-7, galectin-8, galectin-9, galectin-10, galectin-12 and galectin-13, but often galectin-1 and galectin-3 are the galectins which are most commonly used in the assays and methods described hereinabove.

As described in detail herein, we have utilized degradative and secretory autophagy processes to provide a wide variety of therapeutic, diagnostic and screening methods. Our discoveries relating to common and disparate aspects of degradative and secretory autophagy enable diagnoses and treatments of a wide variety of disorders.

These and other aspects of the invention are described further in the detailed Description of the Invention.

BRIEF DESCRIPTION OF THE FIGURES

FIG. 6C-E).

FIG. 22. Duolink (PLA) method for detecting direct interactions in situ. See text for explanation (presence of red dots indicates direct protein-protein interactions, in this case between Tab8b and TBK-1 but not between TBK-1 and NDP52 as they have an adaptor in between.

FIG. 25. Table 1. A selection of proteins identified as released from macrophages induced for secretory autophagy FIGS. 26A and 26B. These figures show an assay which is used for determining whether a compound of unknown activity is a potential inhibitor or inducer of autophagy secretion.

DETAILED DESCRIPTION OF THE INVENTION

Figure 1:
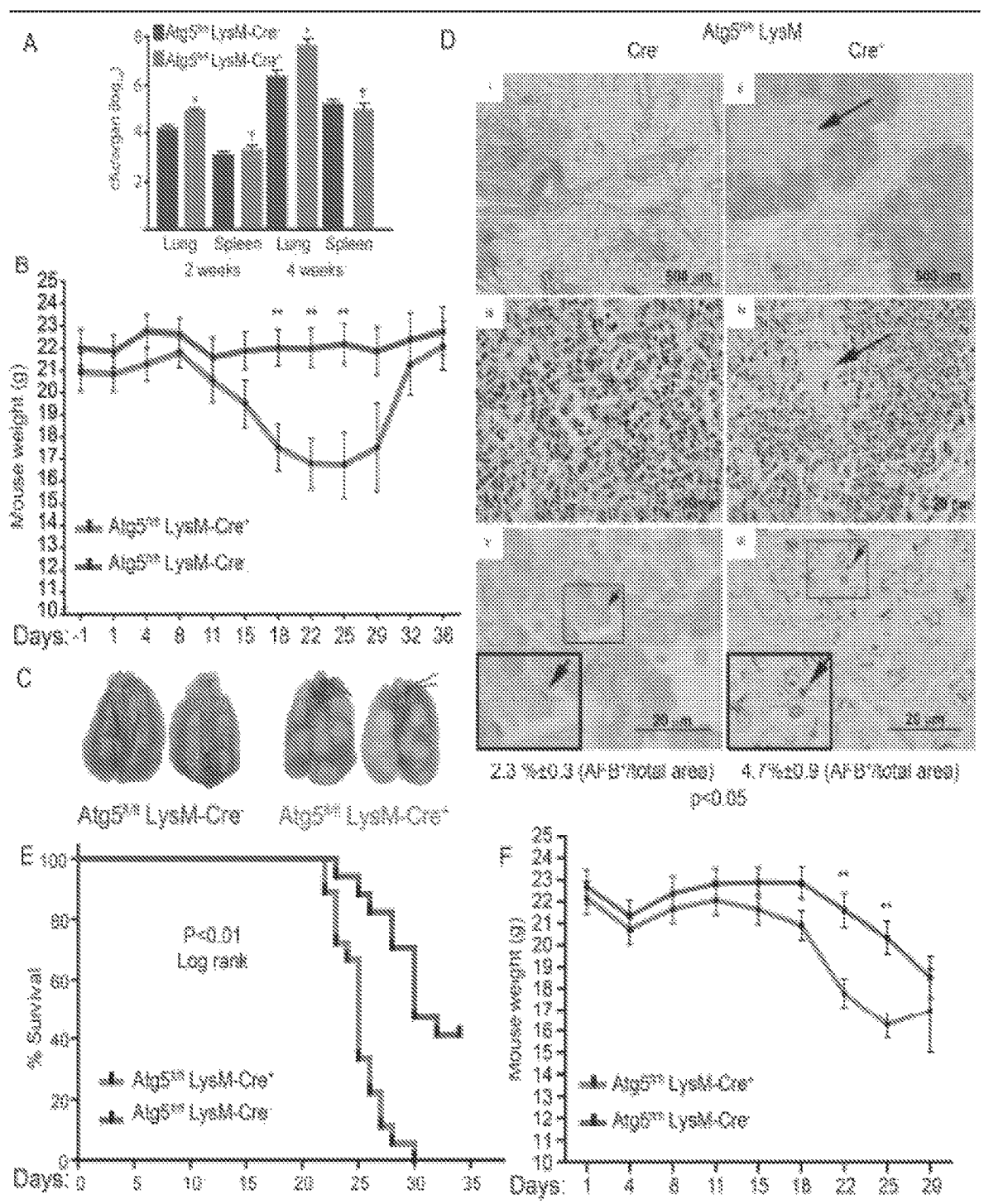
FIG. 1. Autophagy protects from excessive inflammation in a mouse model of tuberculosis infection. (A) Bacterial burden (colony forming units; cfu) in organs of Atg5$^{fl/fl}$ LysM-Cre$^+$ and Atg5$^{fl/fl}$ LysM-Cre$^-$ mice infected aerogenously with low dose *M tuberculosis* H37Rv. The data shown are representative of >3 independent low dose experiments. (B) Weight loss in Atg5$^{fl/fl}$ LysM-Cre$^+$ and Atg5$^{fl/fl}$ LysM-Cre$^-$ mice infected with low dose *M. tuberculosis* H37Rv. (C) Gross lung pathology (low dose). (D) Lung histological sections (low dose, day 36). Panels: i-iv, H&E stain (arrows, necrotic lesions); v and vi, acid-fast staining (arrows, bacilli; insets enlarged area). Numbers: % of total area occupied by acid fast bacilli (AFB). (E) Survival of Atg5$^{fl/fl}$ LysM-Cre$^-$ and Cre$^+$ mice infected with *M. tuberculosis* H37Rv (high dose). (F) Weight loss in Atg5$^{fl/fl}$ LysM-Cre$^-$ and Cre$^+$ mice infected with *M. tuberculosis* H37Rv (high dose). Low infectious dose: $3 \times 10e^2$ ($\pm 30\%$) cfu of initial bacterial deposition per lung following exposure to the infectious inoculum. High dose: $10e^4$ cfu per lung. Mouse survival statistics: Kaplan-Meier survival analysis with the Log-Rank method. Other data, mean±SE, *$p<0.05$, **$p<0.01$, †$>0.05$ (ANOVA; n≥3).

It is noted that, as used in this specification and the appended claims, the singular forms "a," "an," and "the," include plural referents unless expressly and unequivocally limited to one referent. Thus, for example, reference to "a compound" includes two or more different compound. As used herein, the term "include" and its grammatical variants are intended to be non-limiting, such that recitation of items in a list is not to the exclusion of other like items that can be substituted or other items that can be added to the listed items.

The term "compound" or "agent", as used herein, unless otherwise indicated, refers to any specific chemical compound disclosed herein and includes tautomers, regioisomers, geometric isomers as applicable, and also where applicable, optical isomers (e.g. enantiomers) thereof, as well as pharmaceutically acceptable salts thereof. Within its use in context, the term compound generally refers to a single compound, but also may include other compounds such as stereoisomers, regioisomers and/or optical isomers (including racemic mixtures) as well as specific enantiomers or enantiomerically enriched mixtures of disclosed compounds as well as diastereomers and epimers, where applicable in context. The term also refers, in context to prodrug forms of compounds which have been modified to facilitate the administration and delivery of compounds to a site of activity.

The term "patient" or "subject" is used throughout the specification within context to describe an animal, generally a mammal, including a domesticated mammal including a farm animal (dog, cat, horse, cow, pig, sheep, goat, etc.) and preferably a human, to whom treatment, including prophylactic treatment (prophylaxis), with the methods and compositions according to the present invention is provided. For treatment of those conditions or disease states which are specific for a specific animal such as a human patient, the term patient refers to that specific animal, often a human.

The terms "effective" or "pharmaceutically effective" are used herein, unless otherwise indicated, to describe an amount of a compound or composition which, in context, is used to produce or affect an intended result, usually the modulation of secretive or degradative autophagy within the context of a particular treatment or alternatively, the effect of a bioactive agent which is coadministered with the secretive or degradative autophagy modulator in the treatment of disease.

The terms "treat", "treating", and "treatment", etc., as used herein, refer to any action providing a benefit to a patient at risk for or afflicted by a secretive or degradative autophagy mediated disease state or condition as otherwise described herein. The benefit may be in curing the disease state or condition, inhibition its progression, or ameliorating, lessening or suppressing one or more symptom of a secretive autophagy mediated disease state or condition. Treatment, as used herein, encompasses both prophylactic and therapeutic treatment. Prophylactic, when used, refers to "reducing the likelihood" of a disease state, condition or symptom associated with same occurring.

The term "co-administration" or "combination therapy" is used to describe a therapy in which at least two active compounds in effective amounts are used to treat a *M. tuberculosis* infection or other secretive or degradative autophagy-related disorder as otherwise described herein, either at the same time or within dosing or administration schedules defined further herein or ascertainable by those of ordinary skill in the art. Although the term co-administration preferably includes the administration of at least two active compounds to the patient at the same time, it is not necessary that the compounds be administered to the patient at the same time, although effective amounts of the individual compounds will be present in the patient at the same time. In addition, in certain embodiments, co-administration will refer to the fact that two or more compounds are administered at significantly different times, but the effects of the two compounds are present at the same time. Thus, the term co-administration includes an administration in which one active agent (especially a traditional anti-tuberculosis agent such as aminosalicylic acid, isoniazid, ethionamide, myambutol, rifampin, rifabutin, rifapentine, carpeomycin, cycloserine, or a pharmaceutically acceptable salt) is administered at approximately the same time (contemporaneously), or from about one to several minutes to about 24 hours or more than the other bioactive agent coadministered with the autophagy modulator as described herein.

Autophagy modulators include, but are not limited to, autophagy agonists (such as flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline or a mixture thereof or their pharmaceutically acceptable salts) to the patient or subject at risk for or suffering from a tuberculosis infection. Additional agents which may be used in the present invention to inhibit, prevent and/or treat tuberculosis include one or more of benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, betaescin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene and mixtures thereof.

Additional autophagy modulators are those which inhibit or induce the secretion of autophagy modulators, including HMGB1, IL-1 . . . , IL-18, IL-33 or a galectin (e.g. galectin-1, galectin-2, galectin-3, galectin-4, galectin-7, galectin-8, galectin-9, galectin 10, galectin-12 and galectin-13). Inhibitors or inducers of the secrecy of these autophagy modulators include (for HMGB1) anti-HMGB1 antibody, ethyl pyruvate, a high mobility group box (HMGB1) peptide or a biologically active fragment thereof, an antibody to HMGB or an antigen-binding fragment thereof, an HMGB small molecule antagonist, an antibody to TLR2 or an antigen-binding fragment thereof, a soluble TLR2 polypeptide, an antibody to RAGE or an antigen-binding fragment thereof, a soluble RAGE polypeptide and a RAGE small molecule antagonist. In a preferred embodiment, the HMGB1 antagonist is glycyrrhizin. In the case of IL-1β, the inhibitor is an anti-IL-1β humanized monoclonal antibody or Anakinra. In the case of IL-18, the antagonist is IL-18 binding protein (IL-18BP), an antibody against IL-18 including a humanized antibody or a mutein or fused protein. In the case of IL-33, the antagonist is ST2, an anti-ST2 antibody or an antibody, including a humanized antibody which binds to IL-33. In certain embodiments, in the case of galectin (especially galectin-1 and galectin-3), the galectin antagonist/inhibitor is a galactomannan based carbohydrate such as GM-CT-01, GR-MD-02, GCS-100 (CAS No. 531508-98-2) (a pectin have multiple side-branches containing the sugar β-galactose), taloside (a C-2 epimer of galactose) or a pectin (apple, rhubarb, okra, onion), among others.

Any one or more of the inhibitors or inducers of the secretion of these autophagy modulators find use in the treatment of sepsis, inflammatory disease states and disorders and conditions as otherwise described herein and cancer.

The term "*Mycobacterium*", is used to describe a genus of Actinobacteria, given its own family, the Mycobacteriaceae. The genus includes pathogens known to cause serious diseases in mammals, including tuberculosis and leprosy. The Latin prefix "myco" means both fungus and wax; its use here relates to the "waxy" compounds in the cell wall. Mycobacteria are aerobic and non-motile bacteria (except for the species *Mycobacterium marinum* which has been shown to be motile within macrophages) that are characteristically acid-alcohol fast. Mycobacteria do not contain endospores or capsules, and are usually considered Gram-positive. While mycobacteria do not seem to fit the Gram-positive category from an empirical standpoint (i.e. they do not retain the crystal violet stain), they are classified as an acid-fast Gram-positive bacterium due to their lack of an outer cell membrane. All *Mycobacterium* species share a characteristic cell wall, thicker than in many other bacteria, which is hydrophobic, waxy, and rich in mycolic acids/mycolates. The cell wall makes a substantial contribution to the hardiness of this genus.

Many *Mycobacterium* species adapt readily to growth on very simple substrates, using ammonia or amino acids as nitrogen sources and glycerol as a carbon source in the presence of mineral salts. Optimum growth temperatures vary widely according to the species and range from 25° C. to over 50° C.

Some species can be very difficult to culture (i.e. they are fastidious), sometimes taking over two years to develop in culture. Further, some species also have extremely long reproductive cycles: *M. leprae* (leprosy), may take more than 20 days to proceed through one division cycle (for comparison, some *E. coli* strains take only 20 minutes), making laboratory culture a slow process.

A natural division occurs between slowly- and rapidly-growing species. Mycobacteria that form colonies clearly visible to the naked eye within 7 days on subculture are termed rapid growers, while those requiring longer periods are termed slow growers. Mycobacteria are slightly curved or straight rods between 0.2-0.6 m wide by 1.0-10 μm long.

A "*Mycobacterium* infection" includes, but is not limited to, tuberculosis and atypical mycobacterial infections cause by a *Mycobacterium* species other than *M. tuberculosis*. Atypical mycobacterial infections include, but are not limited to, abscesses, septic arthritis, and osteomyelitis (bone infection). They can also infect the lungs, lymph nodes, gastrointestinal tract, skin, and soft tissues. Atypical mycobacterial infections can be caused by *Mycobacterium avium-intracellulare*, which frequently affects AIDS patients and causes lung disease. *Mycobacterium marinum* cause skin infections and is also responsible for swimming pool granuloma. *Mycobacterium ulcerans* cause skin infections. *Mycobacterium kansasii* causes lung disease.

A particularly important *Mycobacterium* species to the present invention is *M. tuberculosis*. The term "Tuberculosis" or "TB" is used to describe the infection caused by the infective agent "*Mycobacterium tuberculosis*" or "*M. tuberculosis*", a tubercle *bacillus* bacteria. Tuberculosis is a potentially fatal contagious disease that can affect almost any part of the body but is most frequently an infection of the lungs. It is caused by a bacterial microorganism, the tubercle bacillus or Mycobacterium tuberculosis.

Tuberculosis is primarily an infection of the lungs, but any organ system is susceptible, so its manifestations may be varied. Effective therapy and methods of control and prevention of tuberculosis have been developed, but the disease remains a major cause of mortality and morbidity throughout the world. The treatment of tuberculosis has been complicated by the emergence of drug-resistant organisms, including multiple-drug-resistant tuberculosis, especially in those with HIV infection.

*Mycobacterium tuberculosis*, the causative agent of tuberculosis, is transmitted by airborne droplet nuclei produced when an individual with active disease coughs, speaks, or sneezes. When inhaled, the droplet nuclei reach the alveoli of the lung. In susceptible individuals the organisms may then multiply and spread through lymphatics to the lymph nodes, and through the bloodstream to other sites such as the lung apices, bone marrow, kidneys, and meninges.

The development of acquired immunity in 2 to 10 weeks results in a halt to bacterial multiplication. Lesions heal and the individual remains asymptomatic. Such an individual is said to have tuberculous infection without disease, and will show a positive tuberculin test. The risk of developing active disease with clinical symptoms and positive cultures for the tubercle *bacillus* diminishes with time and may never occur, but is a lifelong risk. Approximately 5% of individuals with tuberculous infection progress to active disease. Progression occurs mainly in the first 2 years after infection; household contacts and the newly infected are thus at risk.

Many of the symptoms of tuberculosis, whether pulmonary disease or extrapulmonary disease, are nonspecific. Fatigue or tiredness, weight loss, fever, and loss of appetite may be present for months. A fever of unknown origin may be the sole indication of tuberculosis, or an individual may have an acute influenza-like illness. Erythema nodosum, a skin lesion, is occasionally associated with the disease.

The lung is the most common location for a focus of infection to flare into active disease with the acceleration of the growth of organisms. Infections in the lung are the primary focus of the present invention. There may be complaints of cough, which can produce sputum containing mucus, pus- and, rarely, blood. Listening to the lungs may disclose rales or crackles and signs of pleural effusion (the escape of fluid into the lungs) or consolidation if present. In many, especially those with small infiltration, the physical examination of the chest reveals no abnormalities.

Miliary tuberculosis is a variant that results from the blood-borne dissemination of a great number of organisms resulting in the simultaneous seeding of many organ systems. The meninges, liver, bone marrow, spleen, and genitourinary system are usually involved. The term miliary refers to the lung lesions being the size of millet seeds (about 0.08 in. or 2 mm). These lung lesions are present bilaterally. Symptoms are variable.

Extrapulmonary tuberculosis is much less common than pulmonary disease. However, in individuals with AIDS, extrapulmonary tuberculosis predominates, particularly with lymph node involvement, with some pulmonary impact. For example, fluid in the lungs and lung lesions are other common manifestations of tuberculosis in AIDS. The lung is the portal of entry, and an extrapulmonary focus, seeded at the time of infection, breaks down with disease occurring.

Development of renal tuberculosis can result in symptoms of burning on urination, and blood and white cells in the urine; or the individual may be asymptomatic. The symptoms of tuberculous meningitis are nonspecific, with acute or chronic fever, headache, irritability, and malaise.

A tuberculous pleural effusion can occur without obvious lung involvement. Fever and chest pain upon breathing are common symptoms. Bone and joint involvement results in pain and fever at the joint site. The most common complaint is a chronic arthritis usually localized to one joint. Osteomyelitis is also usually present. Pericardial inflammation with fluid accumulation or constriction of the heart chambers secondary to pericardial scarring are two other forms of extrapulmonary disease.

At present, the principal methods of diagnosis for pulmonary tuberculosis are the tuberculin skin test (an intracutaneous injection of purified protein derivative tuberculin is performed, and the injection site examined for reactivity), sputum smear and culture, and the chest x-ray. Culture and biopsy are important in making the diagnosis in extrapulmonary disease.

A combination of two or more drugs is often used in the initial traditional therapy of tuberculous disease. Drug combinations are used to lessen the chance of drug-resistant organisms surviving. The preferred treatment regimen for both pulmonary and extrapulmonary tuberculosis is a 6-month regimen of the antibiotics isoniazid, rifampin, and pyrazinamide given for 2 months, followed by isoniazid and rifampin for 4 months. Because of the problem of drug-resistant cases, ethambutol can be included in the initial regimen until the results of drug susceptibility studies are known. Once treatment is started, improvement occurs in almost all individuals. Any treatment failure or individual relapse is usually due to drug-resistant organisms.

An "inflammatory disorder" "inflammatory disease state" or "inflammatory condition" includes, but is not limited to, lung diseases, hyperglycemic disorders including diabetes and disorders resulting from insulin resistance, such as Type I and Type II diabetes, as well as severe insulin resistance, hyperinsulinemia, and dyslipidemia (e.g. hyperlipidemia (e.g., as expressed by obese subjects), elevated low-density lipoprotein (LDL), depressed high-density lipoprotein (HDL), and elevated triglycerides) and insulin-resistant diabetes, such as Mendenhall's Syndrome, Werner Syndrome, leprechaunism, and lipoatrophic diabetes, renal disorders, such as acute and chronic renal insufficiency, end-stage chronic renal failure, glomerulonephritis, interstitial nephritis, pyelonephritis, glomerulosclerosis, e.g., Kimmelstiel-Wilson in diabetic patients and kidney failure after kidney transplantation, obesity, GH-deficiency, GH resistance, Turner's syndrome, Laron's syndrome, short stature, increased fat mass-to-lean ratios, immunodeficiencies including decreased $CD4^+$ T cell counts and decreased immune tolerance or chemotherapy-induced tissue damage, bone marrow transplantation, diseases or insufficiencies of cardiac structure or function such as heart dysfunctions and congestive heart failure, neuronal, neurological, or neuromuscular disorders, e.g., diseases of the central nervous system including Alzheimer's disease, or Parkinson's disease or multiple sclerosis, and diseases of the peripheral nervous system and musculature including peripheral neuropathy, muscular dystrophy, or myotonic dystrophy, and catabolic states, including those associated with wasting caused by any condition, including, e.g., mental health condition (e.g., anorexia nervosa), trauma or wounding or infection such as with a bacterium or human virus such as HIV, wounds, skin disorders, gut structure and function that need restoration, and so forth.

"Inflammatory disorder" also includes a cancer and an "infectious disease" as defined herein, as well as disorders of bone or cartilage growth in children, including short stature, and in children and adults disorders of cartilage and bone in children and adults, including arthritis and osteoporosis. An "inflammation-associated metabolic disorder" includes a combination of two or more of the above disorders (e.g., osteoporosis that is a sequela of a catabolic state). Specific disorders of particular interest targeted for treatment herein are diabetes and obesity, heart dysfunctions, kidney disorders, neurological disorders, bone disorders, whole body growth disorders, and immunological disorders.

In one embodiment, an "inflammatory disorder" includes central obesity, dyslipidemia including particularly hypertriglyceridemia, low HDL cholesterol, small dense LDL particles and postpranial lipemia; glucose intolerance such as impaired fasting glucose; insulin resistance and hypertension, and diabetes. The term "diabetes" is used to describe diabetes mellitus type I or type II. The present invention relates to a method for improving renal function and symptoms, conditions and disease states which occur secondary to impaired renal function in patients or subjects with diabetes as otherwise described herein. It is noted that in diabetes mellitus type I and II, renal function is impaired from collagen deposits, and not from cysts in the other disease states treated by the present invention.

A "neurodegenerative disorder" or "neuroinflammation" includes, but is not limited to inflammatory disorders such as Alzheimer's Dementia (AD), amyotrophic lateral sclerosis, depression, epilepsy, Huntington's Disease, multiple sclerosis, the neurological complications of AIDS, spinal cord injury, glaucoma and Parkinson's disease.

The term "cancer" is used throughout the specification to refer to the pathological process that results in the formation and growth of a cancerous or malignant neoplasm, i.e., abnormal tissue that grows by cellular proliferation, often more rapidly than normal and continues to grow after the stimuli that initiated the new growth cease. Cancers generally show partial or complete lack of structural organization and functional coordination with the normal tissue and most invade surrounding tissues, metastasize to several sites, and are likely to recur after attempted removal and to cause the death of the patient unless adequately treated. As used herein, the term cancer is used to describe all cancerous disease states applicable to treatment according to the present invention and embraces or encompasses the pathological process associated with all virtually all epithelial cancers, including carcinomas, malignant hematogenous, ascitic and solid tumors. Examples of cancers which may be treated using methods according to the present invention include, without limitation, carcinomas (e.g., squamous-cell carcinomas, adenocarcinomas, hepatocellular carcinomas, and renal cell carcinomas), particularly those of the bladder, bowel, breast, cervix, colon, esophagus, head, kidney, liver, lung, neck, ovary, pancreas, prostate, and stomach; leukemias; benign and malignant lymphomas, particularly Burkitt's lymphoma and Non-Hodgkin's lymphoma; benign and malignant melanomas; myeloproliferative diseases; sarcomas, particularly Ewing's sarcoma, hemangiosarcoma, Kaposi's sarcoma, liposarcoma, myosarcomas, peripheral neuroepithelioma, and synovial sarcoma; tumors of the central nervous system (e.g., gliomas, astrocytomas, oligodendrogliomas, ependymomas, gliobastomas, neuroblastomas, ganglioneuromas, gangliogliomas, medulloblastomas, pineal cell tumors, meningiomas, meningeal sarcomas, neurofibromas, and Schwannomas); germ-line tumors (e.g., bowel cancer, breast cancer, prostate cancer, cervical cancer, uterine cancer, lung cancer, ovarian cancer, testicular cancer, thyroid cancer, astrocytoma, esophageal cancer, pancreatic cancer, stomach cancer, liver cancer, colon cancer, and melanoma); mixed types of neoplasias, particularly carcinosarcoma and Hodgkin's disease; and tumors of mixed origin, such as Wilms' tumor and teratocarcinomas. See, for example, The Merck Manual of Diagnosis and Therapy, 17.sup.th ed. (Whitehouse Station, N.J.: Merck Research Laboratories, 1999) 973-74, 976, 986, 988, 991).

In addition to the treatment of ectopic cancers as described above, the present invention also may be used preferably to treat eutopic cancers such as choriocarcinoma, testicular choriocarcinoma, non-seminomatous germ cell testicular cancer, placental cancer (trophoblastic tumor) and embryonal cancer, among others.

An "immune disorder" includes, but is not limited to, lupus, multiple sclerosis, rheumatoid arthritis, psoriasis, Type I diabetes, complications from organ transplants, xeno transplantation, diabetes, cancer, asthma, atopic dermatitis, autoimmune thyroid disorders, ulcerative colitis, Crohn's disease, Alzheimer's disease and leukemia.

A "biomarker" is any gene or protein whose level of expression in a biological sample is altered compared to that of a pre-determined level. The pre-determined level can be a level found in a biological sample from a normal or healthy subject. Biomarkers include genes and proteins, and variants and fragments thereof. Such biomarkers include DNA comprising the entire or partial sequence of the nucleic acid sequence encoding the biomarker, or the complement of such a sequence. The biomarker nucleic acids also include RNA comprising the entire or partial sequence of any of the nucleic acid sequences of interest. A biomarker protein is a protein encoded by or corresponding to a DNA biomarker of the invention. A biomarker protein comprises the entire or partial amino acid sequence of any of the biomarker proteins or polypeptides. Biomarkers can be detected, e.g. by nucleic acid hybridization, antibody binding, activity assays, polymerase chain reaction (PCR), SI nuclease assay and gene chip.

A "control" as used herein may be a positive or negative control as known in the art and can refer to a control cell, tissue, sample, or subject. The control may, for example, be examined at precisely or nearly the same time the test cell, tissue, sample, or subject is examined. The control may also, for example, be examined at a time distant from the time at which the test cell, tissue, sample, or subject is examined, and the results of the examination of the control may be recorded so that the recorded results may be compared with results obtained by examination of a test cell, tissue, sample, or subject. For instance, as can be appreciated by a skilled artisan, a control may comprise data from one or more control subjects that is stored in a reference database. The control may be a subject who is similar to the test subject (for instance, may be of the same gender, same race, same general age and/or same general health) but who is known to not have a fibrotic disease. As can be appreciated by a skilled artisan, the methods of the invention can also be modified to compare a test subject to a control subject who is similar to the test subject (for instance, may be of the same gender, same race, same general age and/or same general health) but who is known to express symptoms of a disease. In this embodiment, a diagnosis of a disease or staging of a disease can be made by determining whether protein or gene expression levels as described herein are statistically similar between the test and control subjects.

The terms "level" and/or "activity" as used herein further refer to gene and protein expression levels or gene or protein activity. For example, gene expression can be defined as the utilization of the information contained in a gene by transcription and translation leading to the production of a gene product.

In certain non-limiting embodiments, an increase or a decrease in a subject or test sample of the level of measured biomarkers (e.g. proteins or gene expression) as compared to a comparable level of measured proteins or gene expression in a control subject or sample can be an increase or decrease in the magnitude of approximately ±5,000-10,000%, or approximately ±2,500-5,000%, or approximately ±1,000-2,500%, or approximately ±500-1,000%, or approximately ±250-500%, or approximately ±100-250%, or approximately ±50-100%, or approximately +25-50%, or approximately ±10-25%, or approximately ±10-20%, or approximately ±10-15%, or approximately ±5-10%, or approximately ±1-5%, or approximately ±0.5-1%, or approximately ±0.1-0.5%, or approximately ±0.01-0.1%, or approximately ±0.001-0.01%, or approximately ±0.0001-0.001%.

The values obtained from controls are reference values representing a known health status and the values obtained from test samples or subjects are reference values representing a known disease status. The term "control", as used herein, can mean a sample of preferably the same source (e.g. blood, serum, tissue etc.) which is obtained from at least one healthy subject to be compared to the sample to be analyzed. In order to receive comparable results the control as well as the sample should be obtained, handled and treated in the same way. In certain examples, the number of healthy individuals used to obtain a control value may be at least one, preferably at least two, more preferably at least five, most preferably at least ten, in particular at least twenty. However, the values may also be obtained from at least one hundred, one thousand or ten thousand individuals.

A level and/or an activity and/or expression of a translation product of a gene and/or of a fragment, or derivative, or variant of said translation product, and/or the level or activity of said translation product, and/or of a fragment, or derivative, or variant thereof, can be detected using an immunoassay, an activity assay, and/or a binding assay. These assays can measure the amount of binding between said protein molecule and an anti-protein antibody by the use of enzymatic, chromodynamic, radioactive, magnetic, or luminescent labels which are attached to either the anti-protein antibody or a secondary antibody which binds the anti-protein antibody. In addition, other high affinity ligands may be used. Immunoassays which can be used include e.g. ELISAs, Western blots and other techniques known to those of ordinary skill in the art (see Harlow and Lane, Antibodies: A Laboratory Manual, Cold Spring Harbor Laboratory Press, Cold Spring Harbor, N.Y., 1999 and Edwards R, Immunodiagnostics: A Practical Approach, Oxford University Press, Oxford; England, 1999). All these detection techniques may also be employed in the format of microarrays, protein-arrays, antibody microarrays, tissue microarrays, electronic biochip or protein-chip based technologies (see Schena M., Microarray Biochip Technology, Eaton Publishing, Natick, Mass., 2000).

Certain diagnostic and screening methods of the present invention utilize an antibody, preferably, a monoclonal antibody, capable of specifically binding to a protein as described herein or active fragments thereof. The method of utilizing an antibody to measure the levels of protein allows for non-invasive diagnosis of the pathological states of kidney diseases. In a preferred embodiment of the present invention, the antibody is human or is humanized. The preferred antibodies may be used, for example, in standard radioimmunoassays or enzyme-linked immunosorbent assays or other assays which utilize antibodies for measurement of levels of protein in sample. In a particular embodiment, the antibodies of the present invention are used to detect and to measure the levels of protein present in a renal cell or urine sample.

Humanized antibodies are antibodies, or antibody fragments, that have the same binding specificity as a parent antibody, (i.e., typically of mouse origin) and increased human characteristics. Humanized antibodies may be obtained, for example, by chain shuffling or by using phage display technology. For example, a polypeptide comprising a heavy or light chain variable domain of a non-human antibody specific for a disease related protein is combined with a repertoire of human complementary (light or heavy) chain variable domains. Hybrid pairings specific for the antigen of interest are selected. Human chains from the selected pairings may then be combined with a repertoire of human complementary variable domains (heavy or light) and humanized antibody polypeptide dimers can be selected for binding specificity for an antigen. Techniques described for generation of humanized antibodies that can be used in the method of the present invention are disclosed in, for example, U.S. Pat. Nos. 5,565,332; 5,585,089; 5,694,761; and 5,693,762. Furthermore, techniques described for the production of human antibodies in transgenic mice are described in, for example, U.S. Pat. Nos. 5,545,806 and 5,569,825.

In order to identify small molecules and other agents useful in the present methods for treating or preventing a renal disorder by modulating the activity and expression of a disease-related protein and biologically active fragments thereof can be used for screening therapeutic compounds in any of a variety of screening techniques. Fragments employed in such screening tests may be free in solution, affixed to a solid support, borne on a cell surface, or located intracellularly. The blocking or reduction of biological activity or the formation of binding complexes between the disease-related protein and the agent being tested can be measured by methods available in the art.

Other techniques for drug screening which provide for a high throughput screening of compounds having suitable binding affinity to a protein, or to another target polypeptide useful in modulating, regulating, or inhibiting the expression and/or activity of a disease, are known in the art. For example, microarrays carrying test compounds can be prepared, used, and analyzed using methods available in the art. See, e.g., Shalon, D. et al., 1995, International Publication No. WO95/35505, Baldeschweiler et al., 1995, International Publication No. WO95/251116; Brennan et al., 1995, U.S. Pat. No. 5,474,796; Heller et al., 1997, U.S. Pat. No. 5,605,662.

Identifying small molecules that modulate protein activity can also be conducted by various other screening techniques, which can also serve to identify antibodies and other compounds that interact with proteins identified herein and can be used as drugs and therapeutics in the present methods. See, e.g., Enna et al., eds., 1998, Current Protocols in Pharmacology, John Wiley & Sons, Inc., New York N.Y. Assays will typically provide for detectable signals associated with the binding of the compound to a protein or cellular target. Binding can be detected by, for example, fluorophores, enzyme conjugates, and other detectable labels well known in the art. The results may be qualitative or quantitative.

For screening the compounds for specific binding, various immunoassays may be employed for detecting, for example, human or primate antibodies bound to the cells. Thus, one may use labeled anti-hIg, e.g., anti-hIgM, hIgG or combinations thereof to detect specifically bound human antibody. Various labels can be used such as radioisotopes, enzymes, fluorescers, chemiluminescers, particles, etc. There are numerous commercially available kits providing labeled anti-hIg, which may be employed in accordance with the manufacturer's protocol.

In one embodiment, a kit can comprise: (a) at least one reagent which is selected from the group consisting of (i) reagents that detect a transcription product of the gene coding for a protein marker as described herein (ii) reagents that detect a translation product of the gene coding for proteins, and/or reagents that detect a fragment or derivative or variant of said transcription or translation product; (b) optionally, one or more types of cells, including engineered cells in which cellular assays are to be conducted; (c) instructions for diagnosing, or prognosticating a disease, or determining the propensity or predisposition of a subject to develop such a disease or of monitoring the effect of a treatment by determining a level, or an activity, or both said level and said activity, and/or expression of said transcription product and/or said translation product and/or of fragments, derivatives or variants of the foregoing, in a sample obtained from said subject; and comparing said level and/or said activity and/or expression of said transcription product and/or said translation product and/or fragments, derivatives or variants thereof to a reference value representing a known disease status (patient) and/or to a reference value representing a known health status (control) and/or to a reference value; and analyzing whether said level and/or said activity and/or expression is varied compared to a reference value representing a known health status, and/or is similar or equal to a reference value representing a known disease status or a reference value; and diagnosing or prognosticating a disease, or determining the propensity or predisposition of said subject to develop such a disease, wherein a varied or altered level, expression or activity, or both said level and said activity, of said transcription product and/or said translation product and/or said fragments, derivatives or variants thereof compared to a reference value representing a known health status (control) and/or wherein a level, or activity, or both said level and said activity, of said transcription product and/or said translation product and/or said fragments, derivatives or variants thereof is similar or equal to a reference value and/or to a reference value representing a known disease stage, indicates a diagnosis or prognosis of a disease, or an increased propensity or predisposition of developing such a disease, a high risk of developing signs and symptoms of a disease.

Reagents that selectively detect a transcription product and/or a translation product of the gene coding for proteins can be sequences of various length, fragments of sequences, antibodies, aptamers, siRNA, microRNA, and ribozymes. Such reagents may be used also to detect fragments, derivatives or variants thereof.

Compounds used in the methods of treatment of the present invention may be used in pharmaceutical compositions having biological/pharmacological activity for the treatment of, for example, Mycobacterial infections, including a number of other conditions and/or disease states which may appear or occur secondary to the bacterial infection.

These compositions comprise an effective amount of any one or more of the compounds disclosed hereinabove, optionally in combination with a pharmaceutically acceptable additive, carrier or excipient. Compounds used in the methods of treatment of the present invention may also be used as intermediates in the synthesis of compounds exhibiting biological activity as well as standards for determining the biological activity of the present compounds as well as other biologically active compounds.

The compounds used in the methods of treatment of the present invention may be formulated in a conventional manner using one or more pharmaceutically acceptable carriers. Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as prolamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compounds used in the methods of treatment of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally, or intravenously. Preferred routes of administration include oral administration and pulmonary administration (by inhaler/inhalation spray).

Sterile injectable forms of the compounds used in the methods of treatment of the invention may be aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally-acceptable diluent or solvent, for example as a solution in 1, 3-butanediol. Among the acceptable vehicles and solvents that may be employed are water, Ringer's solution and isotonic sodium chloride solution. In addition, sterile, fixed oils are conventionally employed as a solvent or suspending medium. For this purpose, any bland fixed oil may be employed, including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as Ph. Helv or similar alcohol.

The pharmaceutical compositions used in the methods of treatment of this invention may be orally administered in any orally acceptable dosage form including, but not limited to, capsules, tablets, aqueous suspensions or solutions. In the case of tablets for oral use, carriers which are commonly used include lactose and corn starch. Lubricating agents, such as magnesium stearate, are also typically added. For oral administration in a capsule form, useful diluents include lactose and dried corn starch. When aqueous suspensions are required for oral use, the active ingredient is combined with emulsifying and suspending agents. If desired, certain sweetening, flavoring or coloring agents may also be added.

Alternatively, the pharmaceutical compositions used in the methods of treatment of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials include cocoa butter, beeswax and polyethylene glycols.

The pharmaceutical compounds used in the methods of treatment of this invention may also be administered topically, especially when the target of treatment includes areas or organs readily accessible by topical application. Suitable topical formulations are readily prepared for each of these areas or organs.

Topical application also can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention include, but are not limited to, mineral oil, liquid petrolatum, white petrolatum, propylene glycol, polyoxyethylene, polyoxypropylene compound, emulsifying wax and water. Alternatively, the pharmaceutical compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions used in the methods of treatment of this invention may also be administered by nasal aerosol or by inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

The amount of compounds used in the methods of treatment of the instant invention that may be combined with the carrier materials to produce a single dosage form will vary depending upon the host treated, the particular mode of administration. Preferably, the compositions should be formulated so that a therapeutically effective dosage of between about 1 and 25 mg/kg, about 5 to about 15 mg/kg of patient/day of the novel compound can be administered to a patient receiving these compositions. Preferably, pharmaceutical compositions in dosage form according to the present invention comprise a therapeutically effective amount of at least 25 mg of isotopically labeled compound, at least 50 mg of isotopically labeled compound, at least 60 mg of isotopically labeled compound, at least 75 mg of isotopically labeled compound, at least 100 mg of isotopically labeled, at least 150 mg of isotopically labeled compound, at least 200 mg of isotopically labeled compound, at least 250 mg of isotopically labeled compound, at least 300 mg of isotopically labeled compound, about 350 mg of isotopically labeled compound, about 400 mg of isotopically labeled compound, about 500 mg of isotopically labeled compound, about 750 mg of isotopically labeled compound, about 1 g (1000 mg) of isotopically labeled compound, alone or in combination with a therapeutically effective amount of at least one additional anti-tuberculosis agent. Exemplary additional anti-tuberculosis agents which may be used in pharmaceutical compositions include one or more of aminosalicyclic acid/aminosalicylate sodium, capreomycin sulfate, clofazimine, cycloserine, ethambutol hydrochloride (myambutol), kanamycin sulfate, pyrazinamide, rifabutin, rifampin, rifapentine, streptomycin sulfate, gatifloxacin and mixtures thereof, all in therapeutically effective amounts.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease or condition being treated.

Administration of the active compound may range from continuous (intravenous drip) to several oral or inhalation (intratracheal) administrations per day (for example, B.I.D. or Q.I.D.) and may include oral, pulmonary, topical, parenteral, intramuscular, intravenous, sub-cutaneous, transdermal (which may include a penetration enhancement agent), buccal and suppository administration, among other routes of administration. Enteric coated oral tablets may also be used to enhance bioavailability of the compounds from an oral route of administration. The most effective dosage form will depend upon the pharmacokinetics of the particular agent chosen as well as the severity of disease in the patient. Oral dosage forms are particularly preferred, because of ease of administration and prospective favorable patient compliance.

To prepare the pharmaceutical compositions according to the present invention, a therapeutically effective amount of one or more of the compounds according to the present invention is preferably intimately admixed with a pharmaceutically acceptable carrier according to conventional pharmaceutical compounding techniques to produce a dose. A carrier may take a wide variety of forms depending on the form of preparation desired for administration, e.g., oral or parenteral. In preparing pharmaceutical compositions in oral dosage form, any of the usual pharmaceutical media may be used. Thus, for liquid oral preparations such as suspensions, elixirs and solutions, suitable carriers and additives including water, glycols, oils, alcohols, flavoring agents, preservatives, colouring agents and the like may be used. For solid oral preparations such as powders, tablets, capsules, and for solid preparations such as suppositories, suitable carriers and additives including starches, sugar carriers, such as dextrose, mannitol, lactose and related carriers, diluents, granulating agents, lubricants, binders, disintegrating agents and the like may be used. If desired, the tablets or capsules may be enteric-coated or sustained release by standard techniques. The use of these dosage forms may significantly the bioavailability of the compounds in the patient.

For parenteral formulations, the carrier will usually comprise sterile water or aqueous sodium chloride solution, though other ingredients, including those which aid dispersion, also may be included. Of course, where sterile water is to be used and maintained as sterile, the compositions and carriers must also be sterilized. Injectable suspensions may also be prepared, in which case appropriate liquid carriers, suspending agents and the like may be employed.

Liposomal suspensions (including liposomes targeted to viral antigens) may also be prepared by conventional methods to produce pharmaceutically acceptable carriers. This may be appropriate for the delivery of free nucleosides, acyl/alkyl nucleosides or phosphate ester pro-drug forms of the nucleoside compounds according to the present invention.

The present invention also relates to the use of pharmaceutical compositions in an oral dosage form comprising therapeutically effective amounts of isotopically labeled compound according to the present invention, optionally in combination with a pharmaceutically acceptable carrier, additive or excipient. Compositions for oral administration include powders or granules, suspensions or solutions in water or non-aqueous media, sachets, capsules or tablets. Thickeners, diluents, flavorings, dispersing aids, emulsifiers or binders may be desirable.

In preferred aspects of the invention, especially for treatment of *M. tuberculosis* infections, the compound is administered to the lungs of the subject via pulmonary administration, including intratracheal administration. The pharmaceutical composition of the invention for pulmonary administration is usually used as an inhalant. The composition can be formed into dry powder inhalants, inhalant suspensions, inhalant solutions, encapsulated inhalants and like known forms of inhalants. Such forms of inhalants can be prepared by filling the pharmaceutical composition of the invention into an appropriate inhaler such as a metered-dose inhaler, dry powder inhaler, atomizer bottle, nebulizer etc. before use. Of the above forms of inhalants, powder inhalants may be preferable.

When the pharmaceutical composition used in the methods of treatment of the invention is used in the form of a powder, the mean particle diameter of the powder is not especially limited but, in view of the residence of the particles in the lungs, is preferably that the particles fall within the range of about 0.1 to 20 µm, and particularly about 1 to 5 µm. Although the particle size distribution of the powder pharmaceutical composition of the invention is not particularly limited, it is preferable that particles having a size of about 25 µm or more account for not more than about 5% of the particles, and preferably, 1% or less to maximize delivery into the lungs of the subject.

The pharmaceutical composition in the form of a powder can be produced by, for example, using the drying-micronization method, the spray drying method and standard pharmaceutical methodology well known in the art.

By way of example without limitation, according to the drying-pulverization method, the pharmaceutical composition in the form of a powder can be prepared by drying an aqueous solution (or aqueous dispersion) containing the compound or mixtures with other active agents thereof and excipients which provide for immediate release in pulmonary tissue and microparticulating the dried product. Stated more specifically, after dissolving (or dispersing) a pharmaceutically acceptable carrier, additive or excipient in an aqueous medium, compounds according to the present invention in effective amounts are added and dissolved (or dispersed) by stirring using a homogenizer, etc. to give an aqueous solution (or aqueous dispersion). The aqueous medium may be water alone or a mixture of water and a lower alcohol. Examples of usable lower alcohols include methanol, ethanol, 1-propanol, 2-propanol and like watermiscible alcohols. Ethanol is particularly preferable. After the obtained aqueous solution (or aqueous dispersion) is dried by blower, lyophilization, etc., the resulting product is pulverized or microparticulated into fine particles using jet mills, ball mills or like devices to give a powder having the above mean particle diameter. If necessary, additives as mentioned above may be added in any of the above steps.

According to the spray-drying method, the pharmaceutical composition in the form of a powder of the invention can be prepared, for example, by spray-drying an aqueous solution (or aqueous dispersion) containing isoniazid, urea or mixtures thereof and excipients, additives or carriers for microparticulation. The aqueous solution (or aqueous dispersion) can be prepared following the procedure of the above drying-micronization method. The spray-drying process can be performed using a known method, thereby giving a powdery pharmaceutical composition in the form of globular particles with the above-mentioned mean particle diameter.

The inhalant suspensions, inhalant solutions, encapsulated inhalants, etc. can also be prepared using the pharmaceutical composition in the form of a powder produced by the drying-micronization method, the spray-drying method and the like, or by using a carrier, additive or excipient and isoniazid, urea or mixtures thereof that can be administered via the lungs, according to known preparation methods.

Furthermore, the inhalant comprising the pharmaceutical composition of the invention is preferably used as an aerosol. The aerosol can be prepared, for example, by filling the pharmaceutical composition of the invention and a propellant into an aerosol container. If necessary, dispersants, solvents and the like may be added. The aerosols may be prepared as 2-phase systems, 3-phase systems and diaphragm systems (double containers). The aerosol can be used in any form of a powder, suspension, solution or the like.

Examples of usable propellants include liquefied gas propellants, compressed gases and the like. Usable liquefied gas propellants include, for example, fluorinated hydrocarbons (e.g., CFC substitutes such as HCFC-22, HCFC-123, HFC-134a, HFC-227 and the like), liquefied petroleum, dimethyl ether and the like. Usable compressed gases include, for example, soluble gases (e.g., carbon dioxide, nitric oxide), insoluble gases (e.g., nitrogen) and the like.

The dispersant and solvent may be suitably selected from the additives mentioned above. The aerosol can be prepared, for example, by a known 2-step method comprising the step of preparing the composition of the invention and the step of filling and sealing the composition and propellant into the aerosol container.

As a preferred embodiment of the aerosol according to the invention, the following aerosol can be mentioned: Examples of the compounds to be used include isotopically labeled compound alone or in mixtures with other compounds according to the present invention or with other anti-Mycobacterial agents. As propellants, fluorinated hydrocarbons such as HFC-134a, HFC-227 and like CFC substitutes are preferable. Examples of usable solvents include water, ethanol, 2-propanol and the like. Water and ethanol are particularly preferable. In particular, a weight ratio of water to ethanol in the range of about 0:1 to 10:1 may be used.

The aerosol of the invention contains excipient in an amount ranging from about 0.01 to about $10^4$ wt. % (preferably about 0.1 to $10^3$ wt. %), propellant in an amount of about $10^2$ to $10^7$ wt. % (preferably about $10^3$ to $10^6$ wt. %), solvent in an amount of about 0 to $10^6$ wt. % (preferably about 10 to $10^5$ wt. %), and dispersant in an amount of 0 to $10^3$ wt. % (preferably about 0.01 to $10^2$ wt. %), relative to the weight of compound according to the present invention which is included in the final composition.

The pharmaceutical compositions of the invention are safe and effective for use in the therapeutic methods according to the present invention. Although the dosage of the compounds used in the methods of treatment of the invention may vary depending on the type of active substance administered (isoniazid, ethionamide, propionamide and optional additional anti-tuberculosis agents) as well as the nature (size, weight, etc.) of the subject to be diagnosed, the composition is administered in an amount effective for allowing the pharmacologically active substance to be cleaved to cleavage products to be measured. For example, the composition is preferably administered such that the active ingredient (isotopically labeled compound) can be given to a human adult in a dose of at least about 25 mg, at least about 50 mg, at least about 60 mg, at least about 75 mg., at least about 100 mg, at least about 150 mg, at least about 200 mg, at least about 250 mg, at least about 300 mg, at least about 350 mg, at least about 400 mg, at least about 500 mg, at least about 750 mg, at least about 1000 mg, and given in a single dose, including sustained or controlled release dosages once daily.

The form of the pharmaceutical composition of the invention such as a powder, solution, suspension etc. may be suitably selected according to the type of substance to be administered.

As an administration route, direct inhalation via the mouth using an inhaler is usually administered into the airways and in particular, directly to pulmonary tissue, the active substance contained therein produces immediate effects. Furthermore, the composition is formulated as an immediate release product so that cleavage and analysis can begin soon after administration.

Autophagy Overview

During the canonical presentation of autophagy (FIG. 1A), cells digest their cytoplasmic components as an endogenous source of nutrients and energy at times of starvation or as a mechanism for clearance of disused organelles and toxic intracellular aggregates (2A,11A). The canonical autophagy pathway, also referred to as macroautophagy, has been worked out (FIG. 2A) and includes a set of autophagy-specific factors (termed Atgs) responsive to upstream signaling by TOR, AMPK and other inputs (2A,44A,45A). The Atg factors are responsible for the execution of autophagy and the formation of the specialized double membrane organelles, termed autophagosomes. The Atg factors include, among others, the Atg5-Atg12/Atg16 complex. This complex acts as an equivalent to E3 ligases and regulates C-terminal lipidation of Atg8 (or its mammalian equivalent LC3) with phosphatidylethanolamine (PE) essential for autophagosomal membrane growth (2A). Atg8-PE may have a role in membrane tethering and fusion (46A, 47A), albeit this has been disputed and instead SNAREs, the typical regulators of membrane fusion have been invoked (48A). The membrane sources for the formation of autophagosomes primarily originate from transient domains of the ER, termed omegasomes (FIG. 2A), with potential (but heavily debated) contributions of other compartments such as the plasma membrane, mitochondria and Golgi. During degradative stages, autophagosomes fuse with lysosomes to form autolysosomes where the captured cargo is degraded.

Figure 2:
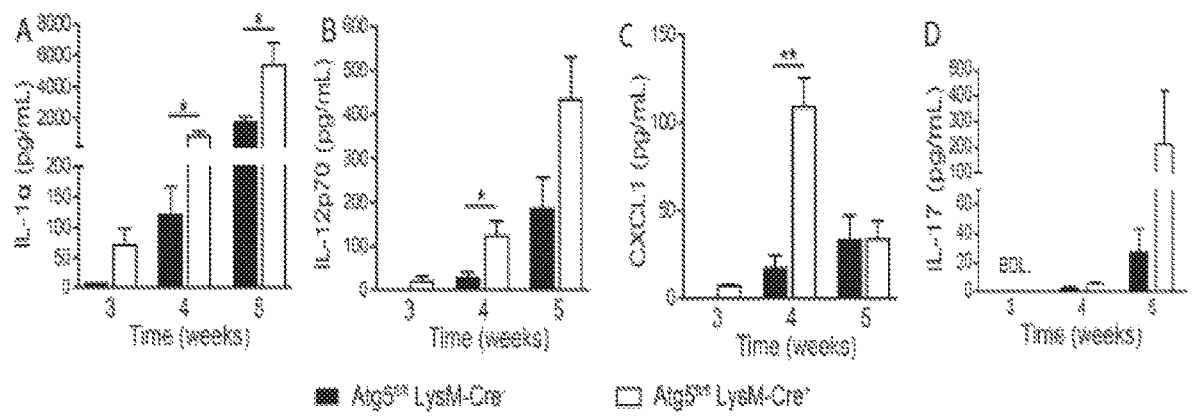
FIG. 2. Increased inflammatory cytokines in Atg5$^{fl/fl}$ LysM-Cre$^+$ mice. Multiplex cytokine detection by Luminex in the lungs of *M. tuberculosis* H37Rv infected Atg5$^{fl/fl}$ LysM-Cre$^-$ and Cre$^+$ mice (low dose). See SI Appendix, Fig. S2 for additional cytokines. BDL, below detection limit. Data, mean±SE, *$p<0.05$, **$p<0.01$, †$>0.05$ (t test; n≥3). Data (D) mean±range from a single cohort of infected mice (see SI Appendix, Fig. S2A for pooled IL-17 data).

FIG. 2A presents three autophagy models ("ER": endoplasmic reticulum; "PM": plasma membrane; "MT": mitochondria). These models are described below.

Model 1. The central membranous structure, omegasome (Ω-some) is derived from the ER (ER cradle model), and is believed to be an early precursor of autophagic isolation membranes (IM) or phagophores. Phagophore crescents close to form double membrane autophagosomes that fuse with lysosomal intermediates to form the degradative organelles, autolysosomes.

Model 2. Mitochondria may contribute membrane or phosphatidylinositol (PE) of relevance for LC3 (A, B and C; and other Atg8 paralogs, GABARAP and GATE-16) C-terminal lipidation into the LC3-II, autophagic membrane-associated form. Mitochondria may also be a source of reactive oxygen species that inactivate ATG4, an LC3 delipidating enzyme. Mitochondria are also one of the major target substrates for autophagic elimination.

Model 3. Plasma membrane Atg16L1-positive (initially LC3-negative) vesicles may contribute to autophagic membrane growth. Factors in the left upper corner represent upstream signaling systems (AMPK, mammalian TOR-mTOR, Ral) controlling induction of autophagy in response to nutritional and cellular energetics signals. Beclin 1 (BEC-1) and class III phosphatidylinositol 3-kinase hVPS34 cooperate in control of phosphatidylinositol 3-phosphate (PI3P) structures that start with omegasome, identifiable by the marker DFCP-1 for which a functional role in autophagy is yet to be established. NBR1 and p62 (also known as sequestosome 1) are autophagic adaptor proteins that capture cargo and interact with LC3; p62 is also present very early at the sites leading to omegasome formation, and is furthermore found in complexes with mTOR that sense amino acid starvation (not shown). Ambra and Atg14L are additional factors interacting with Beclin 1 complexes that are responsible for the early autophagosomal pathway. The lipid kinase hVPS34 interacts with UVRAG and additional factors (not shown) to control autophagosomal maturation into autolysosomes. Several tethering systems along the different stages of the early secretory pathway and the Golgi apparatus (TRAPP, COG, GRASP) influence the formation, expansion (contributed by the only Atg integral membrane protein Atg9) and maturation of autophagosomal organelles.

Figure 3:
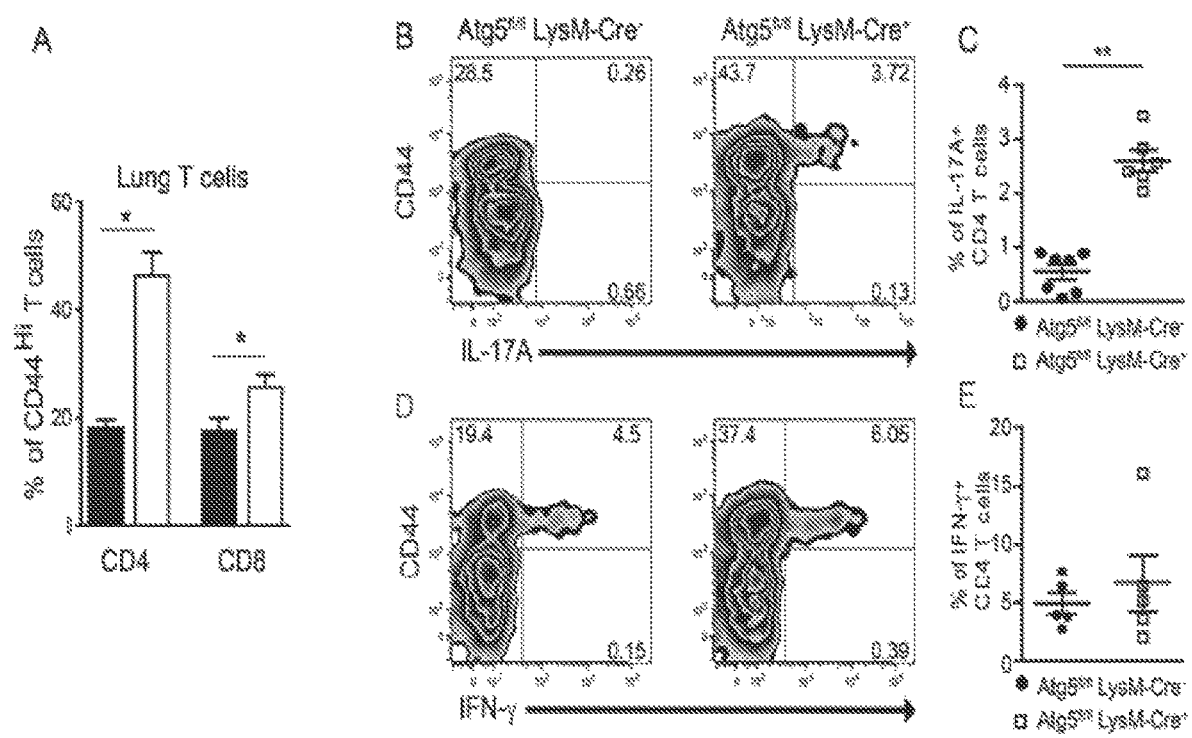
FIG. 3. Activated phenotype of CD4 T cells from uninfected Atg5$^{fl/fl}$ LysM-Cre$^+$ mice and their propensity to undergo polarization into IL-17 producing cells. (A) CD44 expression on lung T cells. Graph displays the percent of CD44$^{high}$ CD4 and CD8 T cells in the lung of uninfected Atg5$^{fl/fl}$ LysM-Cre$^-$ or Cre$^+$ mice. The uninfected mice were 10-12 weeks of age. (B-E) Intracellular levels of IL-17A (top panel) and IFNγ (bottom panel) in CD4 T cells isolated from lungs of uninfected Atg5$^{fl/fl}$ LysM-Cre$^-$ and Cre$^+$ mice and stimulated with phorbol 12-myristate 13-acetate and ionomycin ex vivo in the presence of brefeldin A and monensin. Data: mean±SE; *$p<0.0^5$, **$p<0.01$ (t test; n≥3).

As stated above, autophagy has been assumed to represent primarily a catabolic, lysosomal degradative pathway. The notion of autophagy as a purely degradative pathway was recently challenged by the emergence of reports of the secretory function of autophagy by three independent groups on the secretion of Acb1 in yeast (25A,26A,32A) and IL-1β secretion in mammalian cells (17A,27A). These new developments assign to autophagy a non-degradative function manifested as unconventional protein secretion (FIG. 3A). Furthermore, it has become apparent that autophagy even more broadly intersects with protein trafficking to include effects on the constitutive biosynthetic pathway (23A), regulated exocytosis (19A), and alternative sorting of integral membrane proteins to the plasma membrane (28A). In this proposal, we will delineate the machinery and mechanisms of autophagy-dependent unconventional protein secretion in mammalian cells.

FIG. 3A illustrates the role of autophagy in conventional and unconventional secretion. (From Trends in Cell Biology; 1A) 1. Regulated secretion: secretory lysosomes, granules and other organelles, partially derived from or affected by the post-Golgi vesicles. ATG symbolizes that Atg factors affect regulated secretion, delivering various biologically active cargo as indicated. Others include non-proteinaceous cargo (e.g. ATP secreted from drug-treated cancer cells), provided that they are competent to undergo autophagy, with inflammatory consequences and clearance of transplanted tumors. 2. Autophagy affects constitutive secretion (e.g. IL-6, IL-8) via a compartment intermixed with autophagic organelles, called TASCC (TOR-autophagy spatial coupling compartment). 3. A subset of unconventional secretion processes depend on autophagy (autophagy-based unconventional secretion; secretory autophagy) for secretion of proinflammatory factors IL-1β and HMGB1 in mammalian cells and Acb1 in yeast. GRASP (note that GRASP is normally localized to the Golgi and that it affects early stages of autophagy) is required for autophagy-based unconventional secretion (secretory autophagy). CUPS, a yeast structure implicated in autophagy-based unconventional secretion, may be equivalent to omegasomes in mammalian cells. In addition, autophagy plays a role in unconventional trafficking of the ER-form of CFTR (cystic fibrosis transmembrane conductance regulator) to the apical aspect of the plasma membrane, bypassing the Golgi and rescuing function of mutant CFTR responsible for cystic fibrosis. GRASP plays a role in autophagy-dependent unconventional trafficking of CFTR and in unconventional trafficking of α-integrin to the basolateral plasma membrane in *Drosophila* (a role for autophagy has not been established as yet for α-integrin trafficking).

Figure 4:
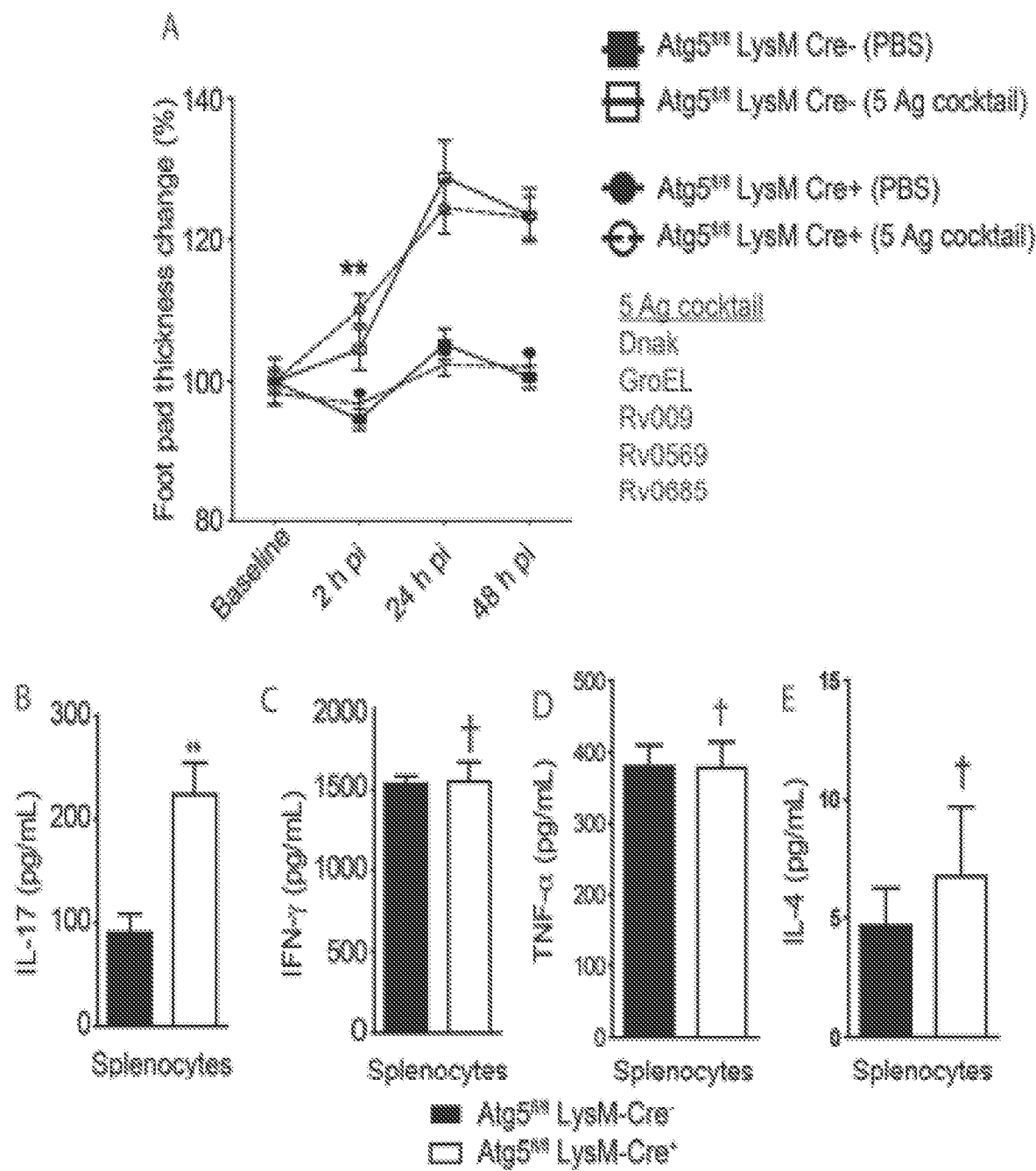
FIG. 4. In vivo and ex vivo immune response to defined *M. tuberculosis* antigens of Atg5$^{fl/fl}$ LysM-Cre$^+$ mice and IL-17 production by their splenocytes upon ex vivo restimulation. (A) DTH reaction (footpad induration) in BCG-infected Atg5$^{fl/fl}$ LysM-Cre and Cre$^+$ mice footpad-injected with the synthetic PPD at day 21 postinfection. Data, percent change (footpad thickness) upon challenge with the synthetic PPD relative to the contralateral PBS-challenged footpad. (B-E) Cytokine production by splenocytes from Atg5$^{fl/fl}$ LysM-Cre$^-$ and Cre$^+$ mice (day 23 post-peritoneal injection of BCG) re-stimulated for 3 days ex vivo with the synthetic PPD. All mice were 10-12 weeks of age at the onset of the experiment. Data: mean±SE; *$p<0.0^5$, **$p<0.01$, † $p>0.05$ (t test; n≥3).

Our present view of protein secretion from eukaryotic cells is dominated by an established, classical paradigm of conventional secretion (FIG. 4A). FIG. 4A shows the well-developed paradigm of conventional protein secretion through endoplasmic reticulum (ER), Golgi and post-Golgi trafficking (right arrow) versus autophagy-dependent unconventional secretion of cytosolic proteins (secretory autophagy). The proteins destined for conventional secretion enter ER via signal peptides, whereas cytosolic proteins destined for secretory autophagy are sequestered into autophagosomes to be exported from the cell.

The Secretory Role of Autophagy

Induction of Autophagy Promotes Inflammasome-Dependent IL-1β Secretion.

Whereas it has been found that basal autophagy reduces extracellular release of the major proinflammatory cytokine IL-1β (50A,51A), we detected the opposite when autophagy was induced in primary murine bone marrow-derived macrophages (BMM). Stimulation of autophagy by starvation strongly enhanced IL-1β secretion in response to the conventional NLRP3 (NALP3) inflammasome agonist nigericin. This effect was also seen in Western blots of caspase 1 and mature IL-1β of culture supernatants from cells grown in the absence of serum, as conventionally done when assessing IL-1β secretion by immunoblotting (52A). A reduced secretion in BMMs from Atg5Fl/Fl LyzM-Cre+ mice, compared to BMMs from their Cre– littermates, was accompanied and contrasted by the higher level of cell-associated pro-IL-1β in Cre– vs Cre+ BMMs. The effects of induced autophagy on secretion of inflammasome substrates described above were not limited to IL-1β, since secretion of another inflammasome-dependent cytokine from the IL-1 family, IL-18 (IL-1F4), was enhanced when autophagy was induced. The increased secretion of IL-1β was not due to increased cell death or non-specific membrane permeability as LDH release showed a kinetic lag behind release of IL-1β whether the inflammasome agonist used was nigericin or silica.

IL-1β and Autophagic Protein LC3 Colocalize in the Cytoplasm.

Figure 5:
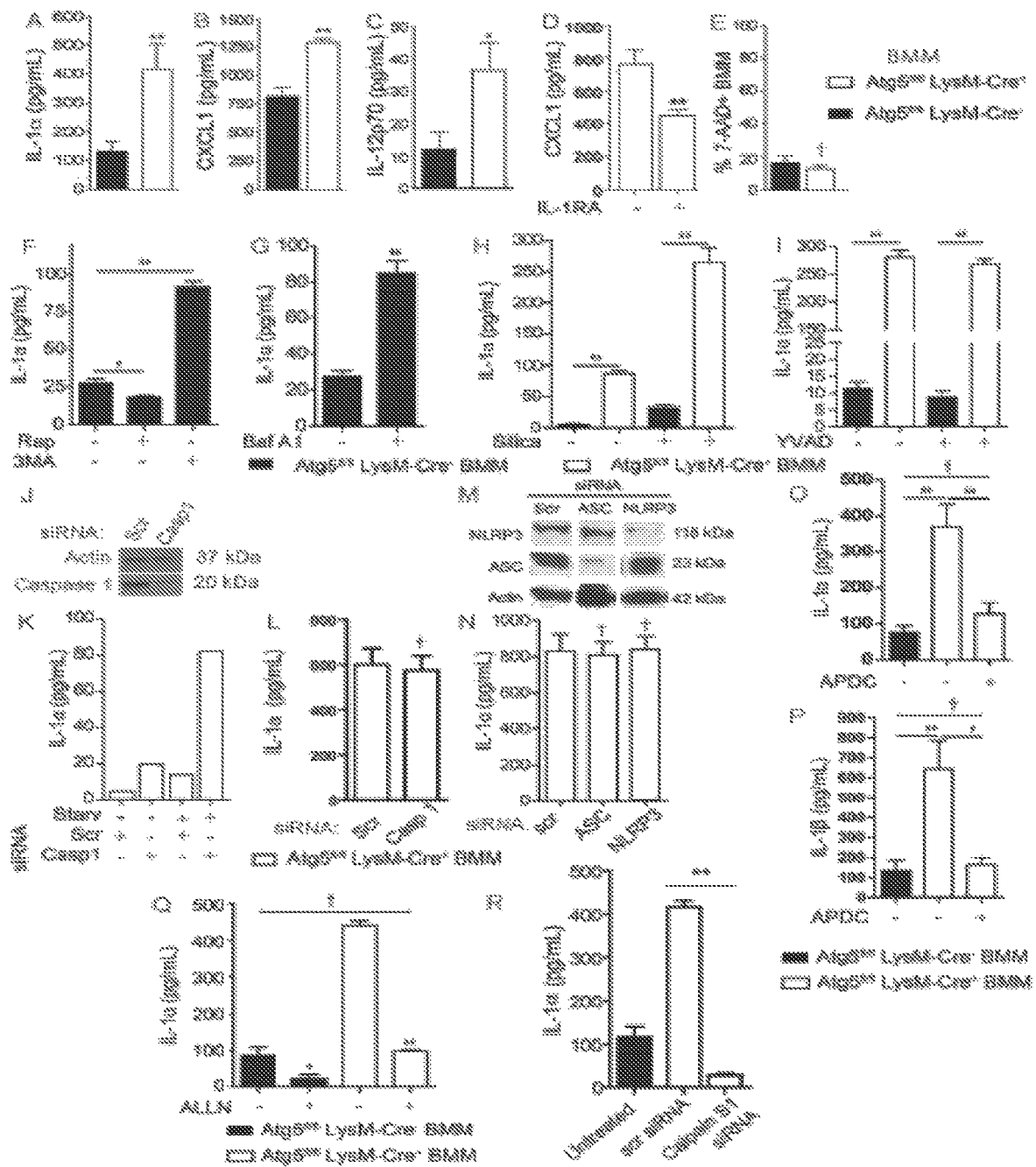
FIG. 5. Excess cytokine secretion is a cell-autonomous property of autophagy-deficient macrophages and IL-1α hypersecretion by Atg5$^{fl/fl}$ LysM-Cre$^+$ macrophages depends on reactive oxygen intermediates and calpain. (A-C) In vitro cytokine (IL-1α, CXCL1, and IL-12p70) release (ELISA) from LPS- and IFN-γ-stimulated Atg5$^{fl/fl}$ LysM-Cre$^-$ and Cre$^+$ bone marrow-derived macrophages (BMM). (D) CXCL1 released from LPS- and IFN-γ-stimulated Atg5$^{fl/fl}$ LysM-Cre$^+$ BMM in the absence of presence of IL-1RA (0.5 g/mL). (E) Fraction of 7-AAD$^+$ BMM after LPS and IFN-γ stimulation in vitro. (F,G) IL-1α and CXCL1 levels (ELISA) in lung homogenates of uninfected Atg5$^{fl/fl}$ LysM-Cre$^-$ and Cre$^+$ mice. (H,I) IL-1α (ELISA) released from LPS- and IFN-γ stimulated Atg5$^{fl/fl}$ LysM-Cre BMM in the presence of 50 µg/ml rapamycin (Rap), 10 mM 3-MA, or 100 nM Bafilomycin A1 (Baf A1) after 12 h of stimulation. (J) IL-1α secretion during inflammasome activation. Atg5$^{fl/fl}$ LysM-Cre$^-$ and Cre$^+$ BMM were pretreated overnight with LPS (100 ng/ml) then stimulated for 1 h in the absence or presence of the inflammasome agonist silica (250 µg/ml) in EBSS. (K) IL-1α secretion in the presence of caspase 1 inhibitor YVAD. Atg5$^{fl/fl}$ LysM-Cre$^-$ and Cre$^+$ BMM were pretreated overnight with LPS (100 ng/ml) then stimulated for 1 h in the absence or presence of YVAD (50 µM) during inflammasome activation with silica as in J. (L) Effects of caspase 1 siRNA knockdown (immunoblot, left) on IL-1α release (graph, right) from Atg5$^{fl/fl}$ LysM-Cre$^+$ BMM. Graph (center), IL-1α release from LPS-stimulated siRNA-treated Atg5$^{fl/fl}$ LysM-Cre$^+$ BMM in full media or EBSS (Starv). Graph (right), same as middle graph in full medium only. Casp 1, caspase 1 siRNA: Scr, scrambled, control siRNA. (M) IL-1α release from LPS- and IFN-γ-stimulated Atg5$^{fl/fl}$ LysM-Cre$^+$ BMM knocked down with siRNA for inflammasome components ASC and NLRP3. (N,O) ROS inhibition and IL-1 secretion: IL-1α (N) and IL-1β (0) released (ELISA) from LPS- and IFN-γ-stimulated Atg5$^{fl/fl}$ LysM-Cre$^-$ and Cre$^+$ BMM in the absence or presence of ROS antagonist APDC (50 µM) after 12 h of incubation. (P) Calpain and IFN-γ hypersecretion phenotype. IL-1β (ELISA) released from LPS- and IFN-γ stimulated Atg5$^{fl/fl}$ LysM-Cre$^-$ and Cre$^+$ BMM in the absence or presence of calpain inhibitor ALLN (100 µM) after 12 h of stimulation. Data, mean±SE, *$p<0.05$, **$p<0.01$, † $p>0.05$ (t test; n≥3).

We considered a model in which autophagy, as a process that can translocate cytosolic proteins and other targets (en masse or specific components) from the cytosol to the inside of vesicular compartments, brought IL-1β into the lumen of autophagic vacuoles followed by exocytosis. When we examined IL-1β and the key marker of autophagosomes, LC3, by immunofluorescence confocal microscopy, LC3 and IL-1β colocalized and displayed major similarities in the overall intracellular organellar distribution (FIG. 5A). The overlap between IL-1β and LC3 remained detectable when cells were treated with nigericin. These observations indicate that autophagic organelles and IL-3 intersect.

Rab8a and Exocyst Components, Regulator of Polarized Sorting to Plasma Membrane, Co-Localize with IL-1β and LC3 and Control IL-1β Secretion.

We also addressed the features of the compartment where LC3 and IL-1β colocalized. We observed an overlap between the LC3+IL-1β+ profiles and Rab8a (FIG. 5A). Rab8a is a regulator of polarized membrane trafficking, constitutive biosynthetic trafficking, and plasma membrane fusion of insulin-responsive 53 and other vesicular carriers (54A-57A). Rab8a also co-localized with LC3 and IL-13 in cells exposed to nigericin. Rab8a was required for enhanced IL-1 secretion caused by starvation-induced autophagy and inflammasome activation with nigericin, since siRNA knockdown of Rab8a diminished IL-1β secretion from BMMs under these conditions. Rab8a knockdown did not change pro-IL-1β mRNA levels. Overexpression of the Rab8a dominant negative mutant (S22N) inhibited IL-1β secretion from RAW264.7 cells, employed in that experiment based on their high efficiency of transfection (verified by flow cytometry of GFP-Rab8a for equal yields). Additionally, LC3+IL-1β + profiles were positive for subunits of the exocyst complex. The exocyst has been shown to cooperate with Rab8a in polarized plasma membrane delivery of vesicular carriers (57A,58A). The presence of exocyst components on IL-1β+ autophagic organelles was also in keeping with a recent report implicating exocyst in autophagy 59. In summary, these experiments indicate that systems involved in vectorial vesicular transport to the plasma membrane participate in autophagy-based unconventional secretion and that Rab8a is required for efficient autophagy-dependent secretion of IL-1β.

GRASP55 Controls Secretion of IL-1.

Figure 6:
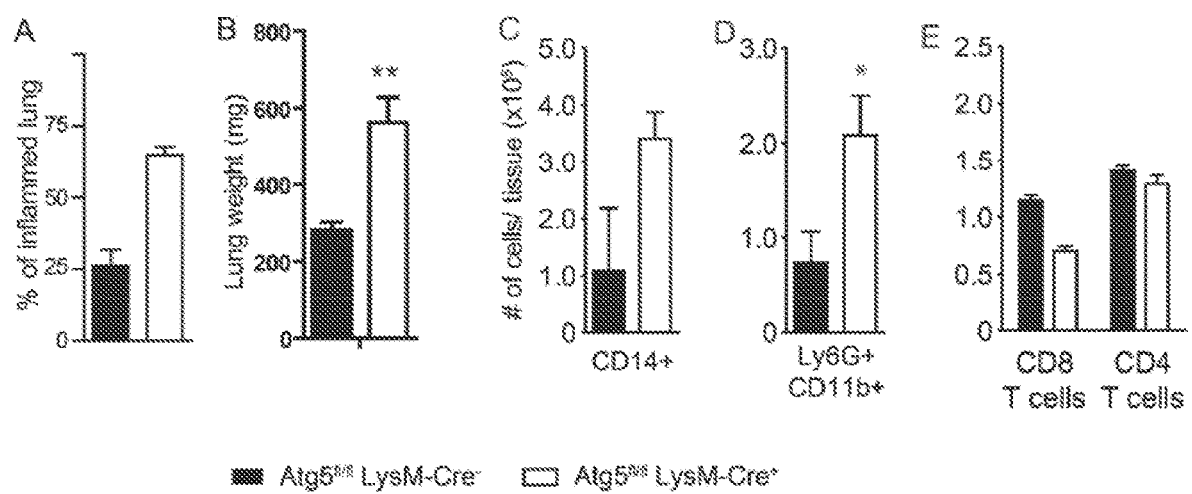
FIG. 6. Atg5$^{fl/fl}$ LysM-Cre$^+$ lung tissue revealed extensive necrotic centers (FIG. 1D, subpanels i-iv) with increase in percent of involved lung area and total lung weight (SI Appendix; Fig. S1A,B) and differential increase in polymorphonucelar (PMN) leukocytes (Ly6G$^+$) (SI Appendix.

Two studies in yeast (24A,26A) have reported that autophagic machinery is required for unconventional secretion of the protein Acb1, and that this pathway depends on the yeast equivalent of mammalian Golgi-associated GRASPs (Golgi reassembly stacking proteins) (30A,60A). Mammalian cells encode two GRASP paralogs, GRASP55 (GORASP2) and GRASP65 (GORASP1). We first tested whether any of the mammalian GRASPs were required for IL-1β secretion. We could not obtain a good knockdown of GRASP65 (GORASP1) and thus could not evaluate its involvement. However, a knockdown of GRASP55 diminished IL-1β secretion (FIG. 6A). A similar downregulation of IL-18 secretion was observed with GRASP55 knockdown. We next tested whether GRASP55 showed any detectable response to inflammasome stimulation. GRASP55 in resting cells is mostly localized aligned within the perinuclear Golgi. However, a fraction of it dispersed upon treatment of cells with the inflammasome agonist nigericin and was found juxtaposed and partially overlapping with LC3 profiles. Thus, GRASP55 responds to inflammasome stimulation and is important for secretion of IL-1β and IL-18.

GRASP55 Controls Autophagy Initiation.

Figure 7:
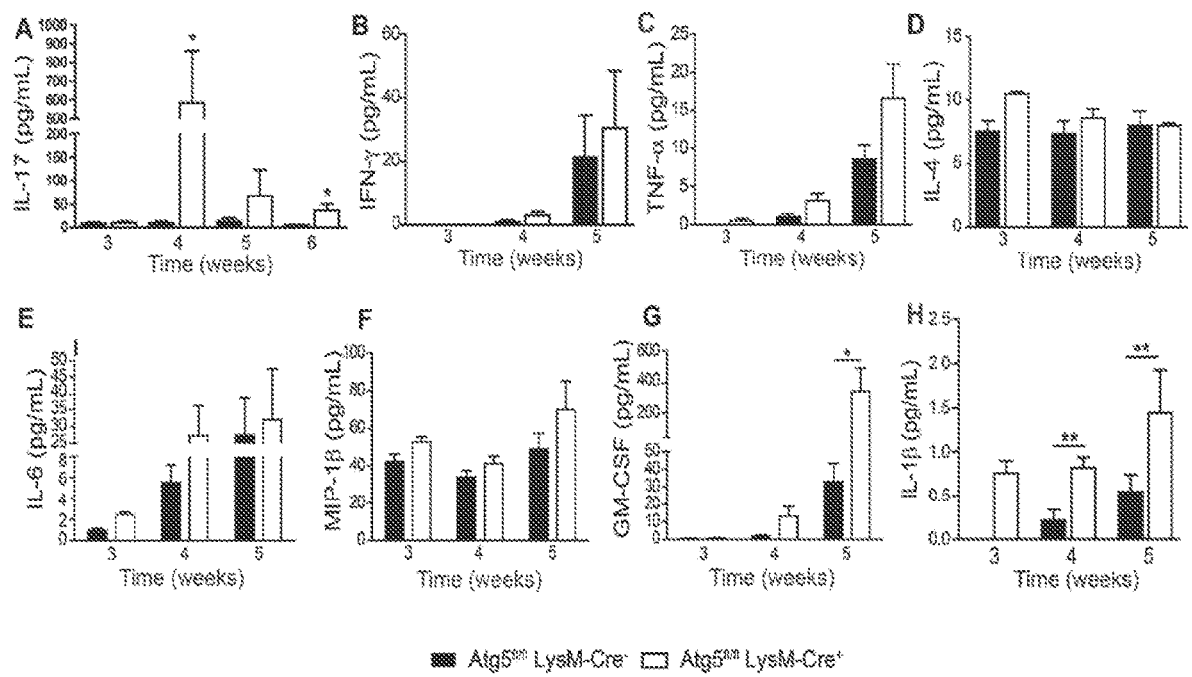
FIG. 7. Cytokines in the lungs of Atg5fl/fl LysM-Cre+ and Cre-mice infected with *M. tuberculosis* H37Rv. (A-H) Multiplex cytokine measurement of IL-17, IFNγ, TNF-α, IL-4, IL-6, MIP-10, GM-CSF, and IL-1β as detected by Luminex in lung homogenates of Atg5fl/fl LysM-Cre and Cre+mice infected with low *M. tuberculosis* dose at weeks 3, 4 and 5 postinfection. IL-17 in panel A represents the combined data from 3 independent cohorts of infections for weeks 3, 4, 5 and 6. Data: mean±SE, *$p<0.05$,**$p<0.01$ (t test; n≥3).

In addition to being required for IL-1β secretion, GRASP55 showed functional effects on LC3 and autophagy, tested by employing two core assays (61A): LC3-II lipidation and the RFP-GFP-LC3 tandem probe. When GRASP55 was knocked down, autophagy initiation was negatively affected, as LC3-II levels were lower in both untreated and bafilomycin A1-treated cells. A partial down regulation of GRASP65 (to the extent that it could be achieved in BMMs) suggested a minor synergistic effect with GRASP55 on LC3-II levels upon induction of autophagy. Knocking down GRASP55 reduced the total number of autophagic puncta, and selectively reduced the formation of autophagosomes but not their maturation (FIG. 7A). This was apparent from the data obtained with the RFP-GFP-LC3 probe following published methods (62A), which showed reduced GFP+ RFP+LC3 profiles (early autophagosome) and equal number of GFP-RFP+LC3 profiles (mature autophagic organelles) in cells knocked down for GRASP55 (FIG. 7A). Thus, mammalian GRASP55, a paralog of GRASP from lower organisms that has thus far been the sole definitive molecular factor associated with unconventional secretion (29A), displays important and previously unappreciated positive regulatory effects on autophagy induction. These findings strengthen the connections between autophagy and GRASPs in general, and specifically demonstrate the role of mammalian GRASP55 both in autophagy initiation and in the secretion of leaderless inflammasome substrates such as IL-1β and IL-18.

Autophagy-Based Unconventional Secretion is not Limited to Proteolytically Processed Inflammasome Substrates.

We tested whether induction of autophagy affected other proteins not connected to proteolytic processing in the inflammasome, such as HMGB1 (high mobility group box 1 protein). HMGB1 is a major pro-inflammatory alarmin or DAMP (damage-associated molecular pattern) normally present in the nucleus (34A). This chromatin-associated nuclear protein (with additional intracellular and extracellular signaling roles), upon exposure to inputs including those that induce autophagy (63A,64A), undergoes a complex set of biochemical and localization changes. In the process, it first translocates from the nucleus into the cytoplasm and then is released from the cytoplasm to act in tissue remodeling signaling (when acting alone) or as an inflammatory mediator (when combined with bacterial agonists or other alarmins such as IL-1β). When tested, starvation and nigericin co-treatment caused HMGB1 extracellular release in an Atg5-dependent manner. An HMGB1 band was detected by immunoblots in BMM culture supernatants upon stimulation of cells with nigericin, whereas HMGB1 was largely diminished when BMMs from Atg5Fl/Fl Cre-LysM mice were tested. HMGB1, along with additional unconventional substrates, depends on inflammasome for secretion although the protein itself is not subjected to proteolytic processing by caspase 1 (65A-68A). These experiments show that autophagy-based unconventional secretion affects release of HMGB1 in a manner similar to IL-1β, broaden the spectrum of autophagy-based unconventional secretion substrates, and establish this type of unconventional secretion as a more general process in extracellular delivery of cytosolic proteins.

Common Versus Specialized Model for Secretory and Degradative Autophagy

Figure 8:
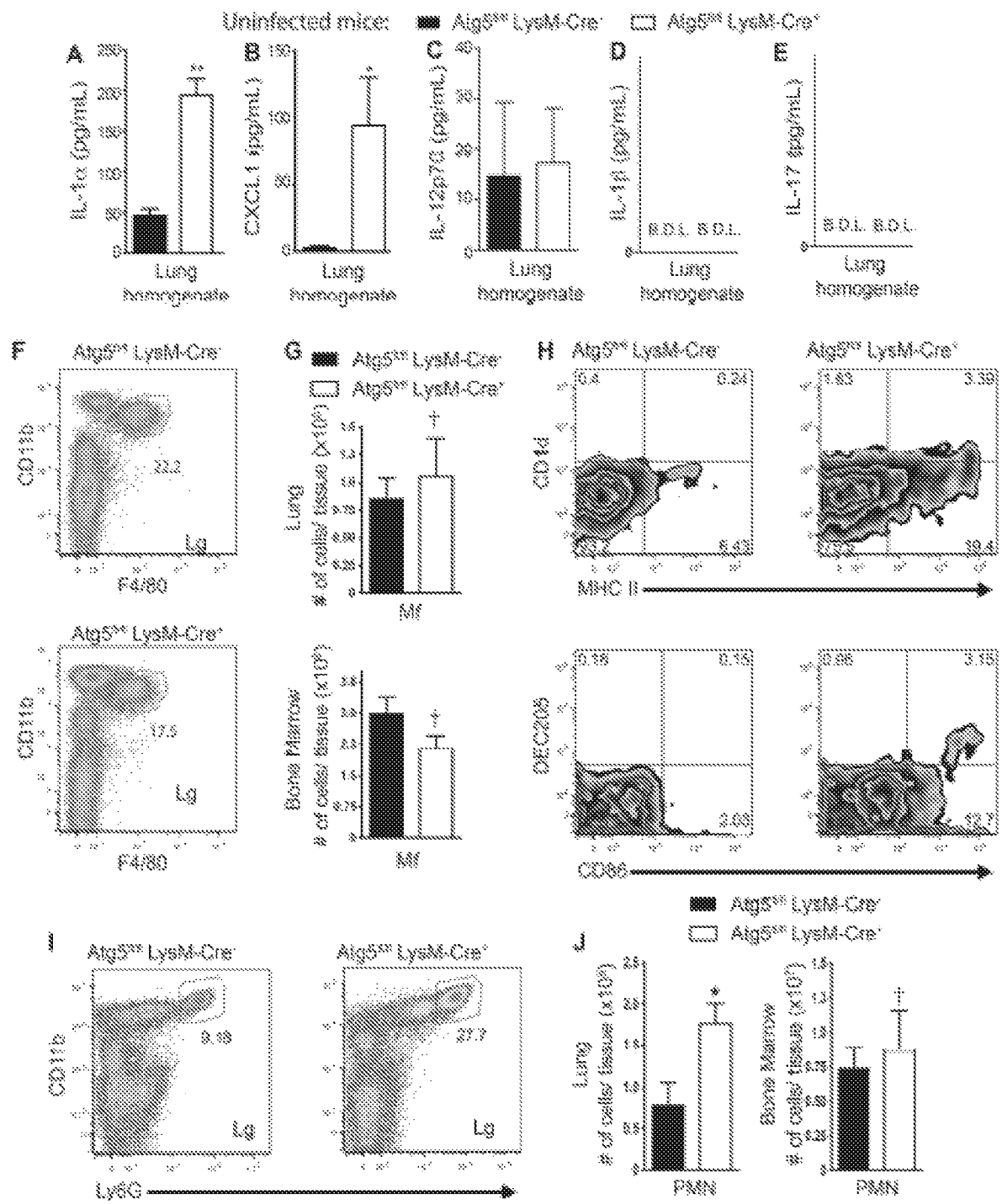
FIG. 8. Cytokine and cellular analysis of uninfected Atg5fl/fl LysM-Cre+ lungs. (A-E) IL-1αCXCL1, IL-12p70, IL-1β, and IL-17 levels (ELISA) in lung homogenates of uninfected Atg5fl/fl LysM-Cre– and Atg5fl/fl LysM-Cre+ mice. (F, G) Flow cytometric quantification of macrophages per organ tissues in uninfected Atg5fl/fl LysM-Cre– and Cre+mice. (H) Activation state of macrophages measured by surface markers CD1d, MHC II, DEC205 and CD86 in the lungs of uninfected Atg5fl/fl LysM-Cre– (left plots) and Cre+mice (right plots). (I,J) Flow cytometric quantification of neutrophils in the lungs and bone marrow of uninfected Atg5fl/fl LysM-Cre– and Cre+mice.
Data, mean±SE, n≥3,
*$p<0.05$, †$>0.05$ (t test).

Our recently published work (17A,27A), presented in the preliminary results section, indicates that GRASP55 (one of the two mammalian GRASPs) is also necessary for canonical, degradative autophagy (27A). Thus, the early secretory and degradative autophagosomes may originate from the common ancestral membrane domains. When and how these domains become sub-specialized is not known. We will test in aim 1 whether such specialization may be driven by different isoforms of early autophagy factors (see FIG. 8A, ER-associated structures entitled "Precursor specialization" and "Precursor").

Secretory and degradative autophagy could diverge later in the pathway. Thus, we seek to determine whether autophagic adapters differ or are modified to select the correct cargo into secretory autophagosomes vs. degradative autophagosomes. Furthermore, since there are six different Atg8 paralogs (three LC3s and three GABARAPs) in mammalian cells, there could be a specialization of a subset of them for secretory autophagy.

We have identified a number of proteins (IL-1, IL-18, HMGB1) that start as cytosolic proteins and end up being secreted through autophagy-dependent unconventional secretion (27A). These proteins exert their known biological functions extracellularly (IL-13, IL-18) or both intracellularly and extracellularly (HMGB1).

The invention is described further in the following non-limiting examples.

Example 1

The In Vivo Role for Autophagy in Protecting Against Tuberculosis
Overview

We used a characterized conditional gene knockout mouse model (Atg5$^{fl/fl}$ LysM-Cre$^+$) with a well documented Atg5 defect in macrophages and infected these mice aerogeneously with the virulent *M. tuberculosis* strain H37Rv. An increase in bacterial burden in the lungs and increased lung pathology were observed in Atg5$^{fl/fl}$ LysM-Cre$^+$ compared to Atg5$^{fl/fl}$ LysM-Cre$^+$ littermates (FIG. 1P, panel A). With higher doses of *M. tuberculosis* Atg5$^{fl/fl}$ LysM-Cre$^+$ mice succumbed sooner to infection. These findings demonstrate for the first time that autophagy is important for control of *M. tuberculosis* in vivo.

It was noticed that the bacterial burden differences between Atg5-proficient and Atg5-deficient mice were quite narrow; they were in the range of one log increase in *M. tuberculosis* colony forming units in the lungs of the autophagy-defective mice. This prompted us to look beyond the previously in vitro established role of autophagy in direct elimination of mycobacteria within macrophages (2). Mice deficient for autophagy in myeloid lineage showed elements of endogenous inflammation in the lung. We furthermore found that lungs of infected autophagy-deficient animals displayed higher levels of IL-17 and IL-1α (FIG. 1P, panel A). We also observed that IL-1α was elevated even in the uninfected lungs and that IL-1α was secreted at higher levels from cultured Atg5-deficient macrophages (FIG. 1P, panel B). Importantly, IL-1α promoted (similarly to the previously known property of IL-1U (3)) a Th17 response in vitro. Furthermore, mixed immune cells isolated from Atg5$^{fl/fl}$ LysM-Cre$^+$ had the propensity to polarize T cells into IL-17-producing phenotype after re-stimulation with specific *M. tuberculosis* antigens. This for the first time implicates autophagy as a negative regulator of Th17 inflammation, and suggests that autophagy suppresses Th17 response and neutrophilia, the potentiators of pathogenesis in tuberculosis (4).

We could not address in vivo the pathology-inducing role of IL-1α inferred from the above experiments, because IL-1α also confers a key protective role against *M. tuberculosis* bacteria as recently shown in the IL-1α knockout mice (5). We nevertheless determined the cell-autonomous mechanism of its elevated secretion by Atg5$^{fl/fl}$ LysM-Cre$^+$ macrophages. The drivers of IL-1α hypersecretion differed from the previously reported mechanisms of increased IL-1β production by autophagy-deficient macrophages (6-8). They were independent of inflammasome constituents and caspase 1, and instead involved a calpain-dependent pathway (FIG. 1P, panel C). The process is initiated by accumulation of unkempt mitochondria in autophagy-deficient macrophages (autophagy normally removes depolarized mitochondria), resulting in reactive oxygen intermediates that lead to increased IL-1α secretion in a calpain-dependent fashion.

Along with the previous in vitro studies addressing the antimycobacterial effector mechanisms of autophagy (17, 22, 26-29, 50, 51) this establishes that autophagy is a bona fide barrier again tuberculosis. Autophagy protects against tissue necrosis and lung pathology, the hallmarks of active tuberculosis. This effect is not a simple consequence of increased bacillary loads but is compounded by the cell-autonomous action of autophagy in macrophage-driven inflammatory processes. Autophagy-deficient macrophages release excessive amounts of inflammatory mediators, such as IL-1α even in the absence of infection. A model emerges whereby these mediators, when in excess, pivot inflammation with features of Th17 response, neutrophilic infiltration, tissue necrosis and organ damage, the main features of active tuberculosis and contagious state of the host.

The mechanisms of cell-autonomous elimination of *M. tuberculosis* by autophagy have been extensively studied in vitro and include direct microbial digestion in autophagolysosomes (26), delivery of neoantimicrobial peptides generated in autolysosomes to compartments harboring intracellular mycobacteria (27, 32, 50) and an interplay of autophagy with conventional antimicrobial peptides (28). Our previous work (32) has highlighted the role of the sequestosome-like receptors (SLR) p62 in these processes, complementing the examples of other SLRs engaging an array of intracellular bacteria (31, 52-55) and viruses (56). In contrast to a preponderance of studies in vitro, autophagic control of microbes is not fully documented in vivo (34, 56). Altered intestinal tissue and Paneth cell function has been noted in response to microbial flora and viral co-infection in an Atg16L1 hypomorph mouse model of Crohn's disease, a chronic inflammatory condition (57). In the animal model of protection against lethal Sindbis virus infection, the dominant contribution of autophagy was in preventing tissue damage independently of viral loads (56). This dovetails with the aspect of our study that shows autophagic protection against excessive inflammation and necrosis in the murine model of tuberculosis. We interpret our data and reports by others (23, 24, 57, 58) as evidence that partial seeds of endogenous inflammation and predisposition to hyper-reactivity exist in autophagy deficient uninfected animals. This is in keeping with the cell autonomous IL-1α hypersecretion shown here, and eventually leads to increased pathology in infected animals. Although leukocytes from uninfected Atg5$^{fl/fl}$ LysM-Cre$^+$ animals show a propensity to polarize into IL-17 cells when tested ex vivo, IL-17 has been detected in vivo only in infected animals.

Thus, the elevated IL-17 response represents a product of interactions between *M. tuberculosis* and a host defective for autophagy in myeloid cells.

The findings that a loss of autophagy in macrophages results in increased release of IL-1α and fosters an environment where T cells produce IL-17 link for the first time autophagy with elements of the Th17 response. The associated elevated presence of neutrophils in the lungs of Atg5$^{fl/fl}$ LysM-Cre$^+$ mice infected with *M. tuberculosis* may be linked to increased pathology. IL-17 and neutrophils play a complex role in tuberculosis (59) and confer both positive (60-62) and negative elements of protection (63-65). The latter aspect of the role of neutrophils in tuberculosis has been recently highlighted in patient cohort studies (66) further compounded by correlates between type I IFN (not addressed in our study) and different participating cells (66, 67). The pathogenic effects of neutrophils are notably manifested during repeat exposure to mycobacterial antigens (65), and at times when a lingering Th17 response does not give way to Th1 control (64) or is not suppressed by regulatory mechanisms (63). Our findings indicate that autophagy, when functional, curbs neutrophilic response, possibly at the time when it needs to be diminished (63-65).

All reports thus far (6, 23-25, 58, 68) agree that autophagy plays a negative role in inflammasome activation through a variety of triggers or additional mechanisms. Autophagy suppresses basal level of inflammasome activation by continually removing (23, 24) endogenous sources of inflammasome agonists such as ROS and mitochondrial DNA (23, 24). Our findings with the ROS-calpain axis in IL-1α activation, and findings by others regarding the ROS-RLR signaling (16) expand these pro-inflammatory phenomena to non-inflammasome pathways downstream of the accumulation of dysfunctional mitochondria and ROS in autophagy-deficient cells. Other changes with inflammatory consequences have been noted in mice with Atg5-deficient macrophages (57, 69).

Tuberculosis has been and remains one of the main global public health hazards further augmented by the HIV co-pandemic (70). The classical presentation of disease is often masked by the untreated HIV co-infection (70), but in principle the majority of humans have a well-developed capacity to contain the infection so that the majority of the world's population infected with the tubercle bacillus is asymptomatic and only approximately 10% of individuals develop active disease. This tip of the iceberg is nevertheless key to continuing the tuberculosis contagion in human populations, since active disease is necessary for the transmission of tuberculosis. We propose that autophagy plays a dual role: it both protects against the microbe and guards against host-inflicted tissue destruction and active disease. In this model autophagy curbs tuberculosis transmission by helping maintain the majority of the infected population asymptomatic. Strategies aimed at pharmacological manipulation of autophagy may diminish tuberculosis spread, which may prove vital in containing the emergence of the increasingly drug-resistant tuberculosis strains.

In conclusion, this work demonstrates for the first time the in vivo role for autophagy in protection against tuberculosis and reveals that autophagy acts beyond its known role as a cellular antimycobacterial effector mechanism. Autophagy prevents excessive inflammation with features of a Th17 response and neutrophilic infiltration, tissue necrosis, and organ damage, the main features of active tuberculosis and contagious state of the host.

Results

Autophagy Protects Mice from *M. tuberculosis*.

The in vivo role of autophagy was investigated by selective genetic deletion of Atg5 in myeloid cells (which include macrophages and granulocytes), with macrophages being of principal interest as the cells both successfully parasitized by intracellular *M. tuberculosis* (33) and targeted by protective immune responses. We used the previously reported conditional gene knockout mouse model Atg5$^{fl/fl}$ LysM-Cre$^+$ with Atg5 deletion in myeloid lineage (34). The Atg5$^+$ mice (Atg5$^{fl/fl}$ LysM-Cre) and their Atg5$^{fl/fl}$ LysM-Cre$^+$ littermates, previously characterized for lack of Atg5 and autophagy in macrophages (6), were subjected to aerogenic infection with low dose (10e$^2$-10e$^3$ cfu) virulent *M. tuberculosis* H37Rv. An increase in bacterial burden (FIG. 1A) and weight loss (FIG. 1B) were observed in Atg5$^M$ LysM-Cre$^+$ compared to Atg5$^{fl/fl}$ LysM-Cre$^-$ littermates. The lung pathology in Atg5$^{fl/fl}$ LysM-Cre$^+$ was remarkable for gross tubercle lesions in contrast to smaller infected foci in the lungs of Atg5$^+$ animals (FIG. 1C). Atg5$^{fl/fl}$ LysM-Cre$^+$ lung tissue revealed extensive necrotic centers (FIG. 1D, subpanels i-iv) with increase in percent of involved lung area and total lung weight (SI Appendix; Fig. S1A,B) and differential increase in polymorphonucelar (PMN) leukocytes (Ly6G$^+$) (SI Appendix; Fig. S1C-E). Acid fast bacilli per unit area were twofold higher in Atg5$^{fl/fl}$ LysM-Cre$^+$ compared to Atg5$^{fl/fl}$ LysM-Cre$^-$ lung sections (FIG. 1D, subpanels v and vi). In keeping with the well-known general resistance of mice to tuberculosis, neither group of mice succumbed to the infection in short term (36 days). When a 10-fold higher infection dose (10e$^4$ cfu) was employed, this resulted in animal mortality with accelerated deaths (along with continuing weight loss) among Atg5$^{fl/fl}$ LysM-Cre$^+$ mice relative to their Atg5$^{fl/fl}$ LysM-Cre$^-$ littermates, starting three weeks post infection (FIG. 1E,F). The above data indicate that Atg5$^f$ LysM-Cre$^+$ mice are more susceptible to *M. tuberculosis* infection over a range of infectious doses and at the same time suggest that the differences in lung pathology exceed the observed differences in bacterial burden.

Atg5-Deficiency in Myeloid Lineage Results in Excessive Inflammatory Response During Infection and Reflects in Part the Elevated Basal Markers of Inflammation.

The cytokine profile in the lungs of *M. tuberculosis* infected animals was remarkable for significant increase in IL-1α, IL-12, and CXCL1 in the Atg5$^{fl/fl}$ LysM-Cre$^+$ lungs relative to Cre$^-$ littermates (FIG. 2A-C). Additionally, IL-17 was elevated in infected mice with disabled autophagy in myeloid cells (FIG. 2D and SI Appendix, Fig. S2A). No differences were observed in the lungs of infected Atg5$^{fl/fl}$ LysM-Cre$^+$ vs. Cre$^-$ mice for IFNγ and TNFα, the well-established anti-tuberculosis cytokines (35), IL-4, a cytokine known to inhibit autophagy ex vivo (22), IL-6, and MIP-1 (SI Appendix; Fig. S2B-F). Some increase in infected Atg5$^{fl/fl}$ LysM-Cre$^+$ vs. Cre$^-$ animals were detected for GM-CSF and IL-1β but the absolute levels of the latter were much lower compared to IL-1α (SI Appendix; Fig. S2G,H).

The uninfected Atg5$^{fl/fl}$ LysM-Cre$^+$ and Cre$^-$ animals did not display signs of or differences in mortality, morbidity, overt disease or discomfort per standards of veterinary care. However, even in the lungs of uninfected mice, IL-1α was detectable at low basal levels and was higher in Atg5$^{fl/fl}$ LysM-Cre$^+$ than in Atg5$^{fl/fl}$ LysM-Cre$^-$ littermates (SI Appendix; Fig. S3A). Increased basal levels of CXCL1 were observed in Atg5$^{fl/fl}$ LysM-Cre$^+$ vs Cre$^-$ lungs (SI Appendix; Fig. S3B) whereas IL-12p70 levels were equal in both uninfected animal groups (SI Appendix; Fig. S3C). IL-1β and IL-17 were below detection limits in the lungs of both uninfected Atg5$^{fl/fl}$ LysM-Cre$^+$ or Cre$^-$ mice (SI Appendix; Fig. S3D,E). Thus, some aspects of cytokine profiles detected during infection (notably IL-1α and CXCL1) were present at low levels in uninfected animals.

In uninfected Atg5$^{fl/fl}$ LysM-Cre$^+$ and Cre$^-$ mice, similar numbers of cells expressing macrophage markers (F4/80' CD11b+; lineage-negative CD3$^-$ CD19$^-$) were detected in the lungs and bone marrow (Fig. S3F,G). However, unlike in autophagy-competent littermates, a fraction of lung macrophages obtained from uninfected Atg5 LysM-Cre$^+$ mice displayed activated phenotype (Fig. S3H). Depending on the marker, 3-20% of Atg5$^{fl/fl}$ LysM-Cre$^+$ macrophages had increased expression of MHC class II, DEC205, and CD86. An indication of increased CD11b$^+$ F4/80$^-$ cell numbers was observed in uninfected Atg5$^{fl/fl}$ LysM-Cre$^+$ lungs (Fig. S3F; top left quadrant). Further examination revealed that these cells were Ly6G$^+$ (1a8 clone) polymorphonuclear granulocytes (neutrophils; PMN) (SI Appendix; Fig. S3I). This increase in PMN total number was only observed in the lungs, as bone marrow PMN numbers were comparable for both groups of mice (SI Appendix; Fig. S3J). The innate immune cell analyses in uninfected animals, along with the cytokine data indicate that the lungs of Atg5$^{fl/fl}$ LysM-Cre$^+$ mice have elevated markers of immune activation under basal conditions relative to Atg5$^{fl/fl}$ LysM-Cre littermates. Thus, autophagy in myeloid cells of the lung, a peripheral organ where continual immune surveillance is necessary, maintains a homeostatic balance of immune cells and their activations states, a process that was perturbed in Atg5$^{fl/fl}$ LysM-Cre$^+$ mice even prior to *M. tuberculosis* exposure.

Functional Autophagic Machinery in Myeloid Lineage Affects CD4 T Cell Activation and IL-17 Response in Uninfected Animals.

The PMN infiltrates, cytokines and the elevated IL-17 in the infected animals suggest elements of a Th17 response (36, 37). In the absence of infection, a fraction of lung CD4 and CD8 T cells with activated/memory phenotype (CD44$^{high}$; FIG. 3A) was significantly increased in uninfected Atg5$^{fl/fl}$ LysM-Cre$^+$ relative to Atg5$^{fl/fl}$ LysM-Cre$^-$ uninfected littermates. We next stimulated total lung leukocytes from the lungs of uninfected mice with phorbol-12-myristate-13-acetate and ionomycin in the presence of protein secretion inhibitors and assessed intracellular levels of IL-17A and IFNγ expressed by CD4 T cells. CD4 T cells from uninfected Atg5$^{fl/fl}$ LysM-Cre$^+$ lungs but not those from uninfected Atg5$^{fl/fl}$ LysM-Cre$^-$ lungs produced IL-17A (FIG. 3B,C). There was no marked difference between the same cells from two sources in their ability to mount IFNγ response (FIG. 3D,E). These findings show the propensity of CD4 T cells from uninfected Atg5$^{fl/fl}$ LysM-Cre$^+$ mice to produce IL-17A upon stimulation, perhaps due to the increase IL-1α in the lung, reflecting the in vivo state of T cells induced by the lack of autophagy in myeloid cells.

Defective Autophagy in Myeloid Lineage of Atg5$^{fl/fl}$ LysM-Cre$^+$ Mice Promotes IL-17 Response to Defined *M. tuberculosis* Antigens by T Cells.

The above proinflammatory properties were next investigated using *M. tuberculosis* immunologically active components. We employed a cocktail of 5 well defined *M. tuberculosis* protein antigens (DnaK, GroEL, Rv009, Rv0569, Rv0685) collectively referred to as synthetic PPD (38) in reference to the purified protein derivative (PPD) used clinically as tuberculin skin test for evidence of recent tuberculosis infection or BCG vaccination. The synthetic PPD reproduces the anatomical and molecular properties of the tuberculin skin test while eliminating false positive inflammatory reactions (seen in uninfected hosts) caused by the contaminating lipoglycans and carbohydrates resident in conventional PPD (38). Atg5$^{fl/fl}$ LysM-Cre$^+$ and Cre$^-$ mice were injected peritoneally with live *M. bovis* BCG and evaluated for the quality of their immune responses three weeks later. Mice were injected with the synthetic PPD or PBS in the hind footpad and delayed type hypersensitivity (DTH) induration was measured at 0, 2, 24 and 48 h postinoculation (FIG. 4A). No differences were observed at 24 and 48 h time point between the autophagy-competent and mutant mice. However, when splenocytes from the BCG-inoculated animals were re-stimulated ex vivo with synthetic PPD, IL-17A was detected at significantly higher levels with Atg5$^{fl/fl}$ LysM-Cre+ splenocytes (FIG. 4B), whereas no differences were observed for typical Th1 and Th2 cytokine signatures (FIG. 4C-E) indicating polarization to IL-17 producing phenotype in Atg5$^{fl/fl}$ LysM-Cre+mice.

Atg5-Deficiency Causes Cell-Autonomous Increase in IL-1α Secretion by Macrophages.

The increased level of IL-17 in the lungs of infected Atg5$^{fl/fl}$ LysM-Cre$^+$ animals is a product of T cell polarization downstream of the changes in myeloid cells. The Atg5 LysM-Cre$^+$ macrophages are known to possess increased inflammasome activation (6, 7, 23-25) downstream of ROS (16) and mitochondrial DNA (24) released from unkempt mitochondria in the absence of autophagy. A key proinflammatory cytokine activated via inflammasome, IL-1β, can lead to Th17 differentiation via IL-receptor signaling (37). However, in the lungs of Atg5$^{fl/fl}$ LysM-Cre$^+$ animals infected with *M. tuberculosis*, IL-1 was present only in minor quantities and undetectable in uninfected lungs (SI Appendix; Fig. S2H and S3D). Nevertheless, IL-1α which also signals via IL-1 receptor, was a dominant cytokine elevated in both infected and uninfected Atg5$^{fl/fl}$ LysM-Cre$^+$ lungs (FIGS. 2A and S2A). When we tested whether IL-1α can substitute for IL-1 (in combination with TGF-β and IL-6) in driving Th17 differentiation ex vivo, IL-1α showed a capacity to promote Th17 polarization (SI Appendix; Fig. S4C-F).

In vitro activated Atg5$^{fl/fl}$ LysM-Cre$^+$ bone marrow macrophages (BMM) recapitulated the in vivo pattern of elevated secretion of IL-1α (along with CXCL1 and IL-12p70) relative to Atg5$^{fl/fl}$ LysM-Cre$^-$ BMM (FIG. 5A-C). The CXCL1 phenotype was likely secondary to IL-1 increase, since IL-1 receptor antagonist (IL-1RA) lowered CXCL1 levels (FIG. 5D). Differential release of IL-1α which is a cytosolic protein, was not due to changes in cell death or increased membrane permeability since in vitro activated BMM from Atg5$^a$ LysM-Cre$^+$ and Atg5$^{fl/fl}$ LysM-Cre$^-$ mice showed no difference in staining with 7-AAD (FIG. 5E). The above experiments, and additional data showing elevated secretion of IL-1α in the lungs of uninfected Atg5$^{fl/fl}$ LysM-Cre$^+$ animals, whereas IL-12p70 and IL-1β were below detection levels in these mice (SI Appendix; Fig. S3D,E), singled out IL-1α as a potential pivot of proinflammatory pathology observed with Atg5$^{fl/fl}$ LysM-Cre$^+$ mice in the tuberculosis model. We could however not test this in vivo, since IL-1α also plays a critical protective role against bacterial burden as recently shown in IL-1α knockout mice (39).

Cellular Mechanism for Increased Secretion of IL-1α by Autophagy-Deficient Macrophages is Inflammasome Independent.

We wanted to understand the cellular mechanism of the IL-1α hypersecretion phenotype in Atg5$^{fl/fl}$ LysM-Cre$^+$ macrophages. Autophagy was confirmed as a negative regulator of IL-1α release by pharmacologically manipulating autophagy in Atg5$^M$ LysM-Cre$^-$ BMM. When autophagy was induced with rapamycin in autophagy-competent macrophages, this reduced the amount of IL-α being secreted (FIG. 5F), paralleling the effects on IL-1β (SI Appendix; Fig. S5A), a cytokine whose secretion has been previously reported to be affected by autophagy by us (6) and others (23, 24). Conversely, when Atg5$^{fl/fl}$ LysM-Cre$^-$ BMM were treated with 3-methyladenine (3MA), an inhibitor of autophagosome formation, the levels of IL-1α were significantly increased (FIG. 5E). As a control, autophagy-deficient Atg5$^{fl/fl}$ LysM-Cre$^+$ BMM showed no response in IL-1α secretion to these pharmacological agents (SI Appendix; Fig. S5B). An effect similar to 3MA was observed upon treatment of Atg5$^{fl/fl}$ LysM-Cre$^-$ BMM with bafilomycin A1 (Baf A1), an inhibitor of autophagic flux (FIG. 5G).

We next considered multiple levels at which absence of autophagy could result in elevated IL-1α secretion. The autophagic adaptor protein p62, which is consumed during autophagy (40) and is the founding member of the SLR family of PRR (31), also prominently functions in innate immunity signaling (41). It accumulates in the absence of autophagy and has been shown to perturb NF-κB responses and cytokine secretion (41, 42). As IL-1α expression is controlled by NF-κB (43), we tested whether p62-mediated NF-κB activation could be the cause of elevated IL-1α expression. However, knocking down p62 via siRNA in Atg5$^{fl/fl}$ LysM-Cre$^+$ BMM (Fig. S6A) did not abrogate the elevated IL-1α secretion by these cells (Fig. S6B). Atg5 was knocked down in BMM from p62$^{-/-}$ knockout mice and this still caused more (albeit less pronounced due to residual Atg5 levels) IL-1α secretion than in the scrambled siRNA control (Fig. S6C). Finally, no increase in IL-1α mRNA levels was detected in Atg5$^{fl/fl}$ LysM-Cre$^+$ BMM relative to Atg5$^{fl/fl}$ LysM-Cre$^-$ BMM (Fig. S6D). Thus, neither does the p62-NF-κB axis contribute to the IL-1α phenotype in Atg5-deficient cells nor is IL-1α expression transcriptionally activated in Atg5 LysM-Cre+ macrophages. We next considered whether IL-1α was a direct target for removal by autophagic organelles. Endogenous LC3 and IL-1α did not colocalize (SI Appendix; Fig. S6E, left image panels) and displayed negative Pearson's colocalization coefficient even upon treatment with BafA1 (SI Appendix; Fig. S6E, graph) while showing complete separation of respective profiles (SI Appendix; Fig. S6E, right image). Thus, IL-1α is unlikely to be a direct substrate for autophagic elimination.

Pathways leading to IL-1α secretion have been reported to utilize inflammasome components (44, 45) although unlike IL-1β, intracellular IL-1α is not an enzymatic substrate for caspase 1. Atg5$^{fl/fl}$ LysM-Cre$^+$ BMM showed elevated levels of p20 caspase 1 (its activated form) in comparison to Atg5$^{fl/fl}$ LysM-Cre$^-$ BMM (SI Appendix; Fig. S6F,G). FLICA (fluorochrome-labeled inhibitor of caspase) assay confirmed increased enzymatically active caspase 1 in Atg5$^{fl/fl}$ LysM-Cre$^+$ BMM compared to Atg5$^{fl/fl}$ LysM-Cre$^-$ BMM (Fig. S6H). In keeping with the potential role for inflammasome and caspase 1 in IL-1α release (44, 45), adding silica to macrophages increased their IL-1α output (FIG. 5H). However, both the basal and inflammasome agonist (silica)-induced levels of IL-1α released from macrophages were increased in Atg5$^{fl/fl}$ LysM-Cre$^+$ BMM. Furthermore, when we tested whether this release was caspase 1 dependent, neither the enzymatic inhibitor of caspase 1 YVAD (FIG. 5I) nor caspase 1 knockdown (FIG. 5J-L) decreased relative IL-1α output. We next tested whether the elevated IL-1α secretion by Atg5$^{fl/fl}$ LysM-Cre$^+$ BMM was dependent on other inflammasome components. Knocking down the key inflammasome constituents ASC and NLRP3 did not diminish IL-1α output of Atg5$^{fl/fl}$ LysM-Cre$^+$ cells (FIG. 5M). These observations, while surprising, are in agreement with the recent report of inflammasome/caspase 1-independent pathway for IL-1α secretion (46), and show that although the inflammasome is activated in Atg5$^{fl/fl}$ LysM-Cre$^+$ BMM it is not responsible for the increase in IL-1α output.

Increased IL-1α in Atg5$^{fl/fl}$ LysM-Cre$^+$ Macrophages Defines a ROS-Calpain Pro-Inflammatory Pathway.

We next searched for potential sources of IL-1α activation upstream of the inflammasome. Reactive oxygen species (ROS) released by accumulated dysfunctional mitochondria in autophagy-deficient cells have been implicated in inflammatory signaling both during RIG-I-like receptors (RLR) response to viral products (16) and inflammasome activation in IL-1β production (23). Atg5$^{fl/fl}$ LysM-Cre$^+$ BMM had elevated mitochondrial content (increased MitoTracker Green staining; SI Appendix, Fig. S7A-C) accompanied by reduced mitochondrial polarization (decrease in MitoTracker Red staining; SI Appendix, Fig. S7D,E). We tested whether ROS associated with the mitochondrial defect in other inflammatory signaling (16, 23) played a role in elevated IL-1α release from Atg5$^{fl/fl}$ LysM-Cre$^+$ macrophages. ROS inhibitor (2R,4R)-4-aminopyrrolidine-2, 4-dicarboxylate (APDC) abrogated excessive IL-1α (FIG. 5O). In keeping with the previous reports (23), APDC also inhibited excessive IL-1β release from Atg5$^{fl/fl}$ LysM-Cre$^+$ BMM (FIG. 5P). Thus, ROS are mediators leading to both IL-1α and IL-1 hypersecretion by autophagy-deficient cells but the machinery downstream of ROS differs for the two cytokines since IL-1β depends on the inflammasome (23) whereas IL-1α as shown here, does not.

ROS can lead to calpain activation (47, 48) although this pathway has not been previously implicated in inflammation. We used ALLN, a calpain inhibitor, to test whether calpain was involved in the IL-1α hypersecretion phenotype of Atg5$^{fl/fl}$ LysM-Cre$^+$ cells. ALLN treatment of Atg5$^{fl/fl}$ LysM-Cre$^+$ completely inhibited the excess IL-1α production normalizing its output to the levels seen with Atg5$^{fl/fl}$ LysM-Cre$^-$ cells (FIG. 5Q). An siRNA knockdown of the common calpain regulatory (small) subunit Capns1, which forms heterodimers with and is required for function of the conventional murine calpains Capn1 and Capn2 (49), abrogated IL-1α hypersecretion (FIG. 5R). We also considered the possibility that calpain may be a target for degradation by autophagy; however, calpain levels were not different between Atg5$^{fl/fl}$ LysM-Cre$^+$ vs. Cre$^-$ cells (SI Appendix; Fig. S6F) and calpain did not colocalize with autophagic organelles (Fig. S6G). We conclude that the IL-1α increase associated with the Atg5 defect in macrophages is due to elevated ROS and depends not on absolute levels of calpain but on its activation downstream of ROS, thus defining a new pro-inflammatory pathway downstream of autophagy.

Materials and Methods

Mice and Infection.

The transgenic Atg5$^{fl/fl}$ LysM-Cre$^+$ (myeloid specific Atg5 deletion) and Atg5$^{fl/fl}$ LysM-Cre$^-$ mice have been previously characterized (34) and the autophagy defect in BMM extensively documented (6). LC3-GFP knock-in transgenic mice (71) and p62$^4$ knockout mice (72) have been previously described. Mice were maintained under specific pathogen-free conditions. F1 progeny from Atg5$^{fl/fl}$ LysM-Cre×Atg5 crosses were genotyped for presence (LysM-Cre) or absence (LysM-Cre) of the LysM-Cre allele by Transnetyx Inc. (Cordova, Tenn.). Infection studies were carried out using murine respiratory infection model (73) and virulent *M. tuberculosis* H37Rv with modifications (74, 75) described in SI Appendix. The standard low dose resulted in the initial bacterial deposition ranging in independent experiments between $10e^2$ to $10e^3$ cfu of *M. tuberculosis* per lung. The high dose had the deposition range of $10e^4$ cfu per lung.

Cells, Flow Cytometry and Immunodetection.

All cells were pretreated with Stain FcX (anti-CD16/32) (Biolegend) before being stained for: CD14 (Sa14-2), F4/80 (BM8), IFNγ (XMG1.2), IL-17A (TC11-18H10.1), CD11b (M1/70), DEC205 (NLDL-145), CD8 (53-6.7), CD86 (GL-1), Ly6G (1A8), CD25 (PC61), MHC II (M5/114.15.2) (Biolegend). CD19 (eBio1D3), TCRβ (H57-597), CD3e (145-2C11), CD44 (IM7), CD4 (GK1.5), CD1d (1B1), DEC205 (205yekta), CD4 (RM4-5), CD45 (30-F11), CD3 (17A2), F4/80 (BM8), CD11b (M1/70), B220 (RA3-6B2), CD8a (53-6.7), IL-12p35 (4D10p35), IL-1α (ALF-161), MCH II (M5/114.15.2), CD25 (PC61.5) (eBioscience), Ly6G (1a8)(BD Biosciences). Caspase 1 activity was measured by flow cytometry using the FLICA caspase 1 reagent (FAM-YVAD-FMK) (Immunochemistry Technologies). Cells were incubated with 7-AAD for viability assessment. Secreted cytokines (IL-1αIL-1β CXCL1, CXCL2 and IL-12p70) were measured by ELISA (R&D Systems). For cytokine secretion, murine BMM, prepared as described (32), were stimulated with 5 ng/ml mIFN-γ and 1 μg/ml LPS, with autophagy agonist and antagonists: rapamycin (Invivogen), 3-MA, and bafilomycin A1; chemical inhibitors: brefeldin A (Biolegend), YVAD and ALLN (Sigma); or IL-1RA (R&D Systems) all added 30 minutes prior to LPS and IFNγ stimulation. For autophagy-dependent unconventional secretion of cytosolic cytokines as described (6), BMM were stimulated for 1 h with 250 μg/ml silica (MINU-SIL-15, US Silica) with starvation (EBSS) to induce autophagy.

DTH and Cell-Mediated Immunity.

Mice were infected intraperitoneally with $5\times10^6$ BCG for 21 days, and then injected with the synthetic PPD (a five antigens cocktail: Dnak, GroEL, Rv009, Rv0569, and Rv0685) at 1.0 gig/ml in PBS, or PBS control, 50 μl in separate footpads. DTH was assessed as described (38) by comparing swelling to a baseline value immediately after injection. Splenocytes ($5.0\times10^5$ cells/well) were restimulated with the synthetic PPD adjusted for 2.0 μg/ml (Dnak and GroEL), and 4.0 μg/ml (Rv009, Rv0569 and Rv0685) and culture supernatants assayed for IFNγ, TNF-α, IL-4 and IL-17 secretion by ELISA (R&D Systems).

T Cell Assays.

Single cell suspensions from whole lungs isolated from naïve Atg5$^{fl/fl}$ LysM-Cre$^+$ and Cre$^-$ mice were cultured in RPMI 10% FBS and Cell Stimulation Cocktail (phorbol 12-myristate 13-acetate and ionomycin plus brefeldin A and monensin; eBioscience) for 4 h and analyzed by flow cytometry. For in vitro polarization, naïve CD4$^+$ T cell from spleens were sorted CD44$^{low}$CD4$^+$ TCRβ$^+$ cells in a MoFlo high speed cell sorter (Beckman Coulter), sorted cells ($5\times10^5$ cells/well), incubated with plate-bound anti-CD3 antibody (Hu et al., 2011) and stimulated with 20 ng/ml IL-6, 5 ng/ml TGF-β, 20 ng/ml IL-1α or 20 ng/ml IL-1β (R&D Systems) in the presence of anti-CD28 (37.51), anti-IFN-γ (R4.6A2), anti-IL-4 (11B11), anti-IL-2 (JE56-1A12) (eBioscience). After 4 days, cells were stimulated with 1× Cell Stimulation Cocktail in the presence of protein transport inhibitors for 5 hours at 37° C. and analyzed by flow cytometry.

REFERENCES FOR EXAMPLE 1 AND BACKGROUND OF THE INVENTION

1. Mizushima N, Yoshimori T, & Ohsumi Y (2011) The role of atg proteins in autophagosome formation. *Annual review of cell and developmental biology* 27:107-132.
2. Mizushima N, Levine B, Cuervo A M, & Klionsky D J (2008) Autophagy fights disease through cellular self-digestion. *Nature* 451(7182):1069-1075.
3. Levine B, Mizushima N, & Virgin H W (2011) Autophagy in immunity and inflammation. *Nature* 469(7330):323-335.
4. Narita M, et al. (2011) Spatial coupling of mTOR and autophagy augments secretory phenotypes. *Science* 332 (6032):966-970.
5. Manjithaya R, Anjard C, Loomis W F, & Subramani S (2010) Unconventional secretion of *Pichia pastoris* Acb1 is dependent on GRASP protein, peroxisomal functions, and autophagosome formation. *J Cell Biol* 188(4):537-546.
6. Dupont N, et al. (2011) Autophagy-based unconventional secretory pathway for extracellular delivery of IL-1beta. *The EMBO journal* 30(23):4701-4711.
7. Deretic V, Jiang S, & Dupont N (2012) Autophagy intersections with conventional and unconventional secretion in tissue development, remodeling and inflammation. *Trends in Cell Biology* In pres.
8. He C & Levine B (2010) The Beclin 1 interactome. *Current opinion in cell biology* 22(2):140-149.
9. Tattoli I, et al. (2012) Amino acid starvation induced by invasive bacterial pathogens triggers an innate host defense program. *Cell Host & Microbe* 11(6):563-575.
10. Criollo A, et al. (2011) Inhibition of autophagy by TAB2 and TAB3. *The EMBO journal* 30(24):4908-4920.
11. Lee H K, Lund J M, Ramanathan B, Mizushima N, & Iwasaki A (2007) Autophagy-dependent viral recognition by plasmacytoid dendritic cells. *Science* 315(5817):1398-1401.
12. Saitoh T & Akira S (2010) Regulation of innate immune responses by autophagy-related proteins. *J Cell Biol* 189 (6):925-935.
13. Thurston T L, Wandel M P, von Muhlinen N, Foeglein A, & Randow F (2012) Galectin 8 targets damaged vesicles for autophagy to defend cells against bacterial invasion. *Nature* 482(7385):414-418.
14. Deretic V (2012) Autophagy—an emerging immunological paradigm. *J Immunol* In press.
15. Jounai N, et al. (2011) NLRP4 negatively regulates autophagic processes through an association with beclin1. *J Immunol* 186(3):1646-1655.
16. Tal M C, et al. (2009) Absence of autophagy results in reactive oxygen species-dependent amplification of RLR signaling. *Proc Natl Acad Sci USA* 106(8):2770-2775.
17. Xu Y, et al. (2007) Toll-like receptor 4 is a sensor for autophagy associated with innate immunity. *Immunity* 27(1):135-144.
18. Delgado M A, Elmaoued R A, Davis A S, Kyei G, & Deretic V (2008) Toll-like receptors control autophagy. *Embo J* 27(7):1110-1121.
19. Travassos L H, et al. (2010) Nod1 and Nod2 direct autophagy by recruiting ATG16L1 to the plasma membrane at the site of bacterial entry. *Nature immunology* 11(1):55-62.
20. Lee H K, et al. (2010) In vivo requirement for Atg5 in antigen presentation by dendritic cells. *Immunity* 32(2): 227-239.
21. Jia W, Pua H H, Li Q J, & He Y W (2011) Autophagy regulates endoplasmic reticulum homeostasis and calcium mobilization in T lymphocytes. *J Immunol* 186(3):1564-1574.
22. Harris J, et al. (2007) T helper 2 cytokines inhibit autophagic control of intracellular *Mycobacterium tuberculosis*. *Immunity* 27(3):505-517.

23. Zhou R, Yazdi A S, Menu P, & Tschopp J (2011) A role for mitochondria in NLRP3 inflammasome activation. *Nature* 469(7329):221-225.
24. Nakahira K, et al. (2011) Autophagy proteins regulate innate immune responses by inhibiting the release of mitochondrial DNA mediated by the NALP3 inflammasome. *Nature immunology* 12(3):222-230.
25. Shi C S, et al. (2012) Activation of autophagy by inflammatory signals limits IL-1beta production by targeting ubiquitinated inflammasomes for destruction. *Nature immunology* 13(3):255-263.
26. Gutierrez M G, et al. (2004) Autophagy is a defense mechanism inhibiting BCG and *Mycobacterium tuberculosis* survival in infected macrophages. Cell 119(6):753-766.
27. Alonso S, Pethe K, Russell D G, & Purdy G E (2007) Lysosomal killing of *Mycobacterium* mediated by ubiquitin-derived peptides is enhanced by autophagy. *Proc Natl Acad Sci USA* 104(14):6031-6036.
28. Yuk J M, et al. (2009) Vitamin D3 induces autophagy in human monocytes/macrophages via cathelicidin. *Cell host & microbe* 6(3):231-243.
29. Kim J J, et al. (2012) Host cell autophagy activated by antibiotics is required for their effective antimycobacterial drug action. *Cell host & microbe* 11(5):457-468.
30. Nakagawa L et al. (2004) Autophagy defends cells against invading group A *Streptococcus*. *Science* 306 (5698):1037-1040.
31. Deretic V (2012) Autophagy as an innate immunity paradigm: expanding the scope and repertoire of pattern recognition receptors. *Current opinion in immunology* 24(1):21-31.
32. Ponpuak M. et al. (2010) Delivery of cytosolic components by autophagic adaptor protein p62 endows autophagosomes with unique antimicrobial properties. *Immunity* 32(3):329-341.
33. Vergne I, Chua J, Singh S B, & Deretic V (2004) Cell biology of *Mycobacterium tuberculosis* phagosome. *Annu Rev Cell Dev Biol* 20:367-394.
34. Zhao Z, et al. (2008) Autophagosome-independent essential function for the autophagy protein Atg5 in cellular immunity to intracellular pathogens. *Cell Host Microbe* 4(5):458-469.
35. Flynn J L & Chan J (2001) Immunology of tuberculosis. *Annu Rev Immunol* 19:93-129.
36. Korn T, Bettelli E, Oukka M, & Kuchroo V K (2009) IL-17 and Th17 Cells. *Annual review of immunology* 27:485-517.
37. Chung Y, et al. (2009) Critical regulation of early Th17 cell differentiation by interleukin-1 signaling. *Immunity* 30(4):576-587.
38. Yang H, et al. (2011) Three protein cocktails mediate delayed-type hypersensitivity responses indistinguishable from that elicited by purified protein derivative in the guinea pig model of *Mycobacterium tuberculosis* infection. *Infect Immun* 79(2):716-723.
39. Mayer-Barber K D, et al. (2011) Innate and Adaptive Interferons Suppress IL-1alpha and IL-1beta Production by Distinct Pulmonary Myeloid Subsets during *Mycobacterium tuberculosis* Infection. *Immunity* 35(6):1023-1034.
40. Jain A, et al. (2010) p62/SQSTM1 is a target gene for transcription factor NRF2 and creates a positive feedback loop by inducing antioxidant response element-driven gene transcription. *J Biol Chem* 285(29):22576-22591.
41. Moscat J & Diaz-Meco M T (2009) p62 at the crossroads of autophagy, apoptosis, and cancer. *Cell* 137(6):1001-1004.
42. Mathew R, et al. (2009) Autophagy suppresses tumorigenesis through elimination of p62. *Cell* 137(6):1062-1075.
43. Xia Y, et al. (1999) RelB modulation of IkappaBalpha stability as a mechanism of transcription suppression of interleukin-1alpha (IL-1alpha), IL-1beta, and tumor necrosis factor alpha in fibroblasts. Molecular and cellular biology 19(11):7688-7696.
44. Fettelschoss A, et al. (2011) Inflammasome activation and IL-1beta target IL-1alpha for secretion as opposed to surface expression. *Proceedings of the National Academy of Sciences of the United States of America* 108(44): 18055-18060.
45. Keller M, Ruegg A, Werner S, & Beer H D (2008) Active caspase-1 is a regulator of unconventional protein secretion. *Cell* 132(5):818-831.
46. Gross O, et al. (2012) Inflammasome activators induce interleukin-1alpha secretion via distinct pathways with differential requirement for the protease function of caspase-1. *Immunity* 36(3):388-400.
47. Li Y, Arnold J M, Pampillo M, Babwah A V, & Peng T (2009) Taurine prevents cardiomyocyte death by inhibiting NADPH oxidase-mediated calpain activation. *Free radical biology & medicine* 46(1):51-61.
48. Sharma A K & Rohrer B (2007) Sustained elevation of intracellular cGMP causes oxidative stress triggering calpain-mediated apoptosis in photoreceptor degeneration. *Current eye research* 32(3):259-269.
49. Sorimachi H, Hata S, & Ono Y (2011) Impact of genetic insights into calpain biology. *J Biochem* 150(1):23-37.
50. Kim B H, et al. (2011) A family of IFN-gamma-inducible 65-kD GTPases protects against bacterial infection. *Science* 332(6030):717-721.
51. Hartman M L & Kornfeld H (2011) Interactions between Naive and Infected Macrophages Reduce *Mycobacterium tuberculosis* Viability. *PLoS One* 6(11):e27972.
52. Thurston T L, Ryzhakov G, Bloor S, von Muhlinen N, & Randow F (2009) The TBK1 adaptor and autophagy receptor NDP52 restricts the proliferation of ubiquitin-coated bacteria. *Nat Immunol* 10(11):1215-1221.
53. Dupont N, et al. (2009) Shigella phagocytic vacuolar membrane remnants participate in the cellular response to pathogen invasion and are regulated by autophagy. *Cell Host Microbe* 6(2):137-149.
54. Yoshikawa Y, et al. (2009) *Listeria monocytogenes* ActA-mediated escape from autophagic recognition. *Nat Cell Biol* 11(10):1233-1240.
55. Wild P, et al. (2011) Phosphorylation of the autophagy receptor optineurin restricts *Salmonella* growth. *Science* 333(6039):228-233.
56. Orvedahl A, et al. (2010) Autophagy Protects against Sindbis Virus Infection of the Central Nervous System. *Cell Host Microbe* 7(2):115-127.
57. Cadwell K, et al. (2010) Virus-plus-susceptibility gene interaction determines Crohn's disease gene Atg16L1 phenotypes in intestine. *Cell* 141(7):1135-1145.
58. Saitoh T, et al. (2008) Loss of the autophagy protein Atg16L1 enhances endotoxin-induced IL-beta production. *Nature* 456(7219):264-268.
59. Torrado E & Cooper A M (2010) IL-17 and Th17 cells in tuberculosis. *Cytokine Growth Factor Rev* 21(6):455-462.

60. Pedrosa J, et al. (2000) Neutrophils play a protective nonphagocytic role in systemic *Mycobacterium tuberculosis* infection of mice. *Infect Immun* 68(2):577-583.
61. Seiler P, et al. (2003) Early granuloma formation after aerosol *Mycobacterium tuberculosis* infection is regulated by neutrophils via CXCR3-signaling chemokines. *Eur J Immunol* 33(10):2676-2686.
62. Khader S A, et al. (2007) IL-23 and IL-17 in the establishment of protective pulmonary CD4+ T cell responses after vaccination and during *Mycobacterium tuberculosis* challenge. *Nat Immunol* 8(4):369-377.
63. Desvignes L & Ernst J D (2009) Interferon-gamma-responsive nonhematopoietic cells regulate the immune response to *Mycobacterium tuberculosis*. *Immunity* 31(6):974-985.
64. Nandi B & Behar S M (2011) Regulation of neutrophils by interferon-gamma limits lung inflammation during tuberculosis infection. *The Journal of experimental medicine* 208(11):2251-2262.
65. Cruz A, et al. (2010) Pathological role of interleukin 17 in mice subjected to repeated BCG vaccination after infection with *Mycobacterium tuberculosis*. *The Journal of experimental medicine* 207(8):1609-1616.
66. Berry M P, et al. (2010) An interferon-inducible neutrophil-driven blood transcriptional signature in human tuberculosis. *Nature* 466(7309):973-977.
67. Desvignes L, Wolf A J, & Ernst J D (2012) Dynamic roles of type I and type II IFNs in early infection with *Mycobacterium tuberculosis*. *J Immunol* 188(12):6205-6215.
68. Harris J, et al. (2011) Autophagy controls IL-1 {beta} secretion by targeting pro-IL-1 {beta} for degradation. *J Biol Chem*.
69. Cadwell K, et al. (2008) A key role for autophagy and the autophagy gene Atg16l1 in mouse and human intestinal Paneth cells. *Nature* 456(7219):259-263.
70. Nunn P, et al. (2005) Tuberculosis control in the era of HIV. *Nat Rev Immunol* 5(10):819-826.
71. Mizushima N, Yamamoto A, Matsui M, Yoshimori T, & Ohsumi Y (2004) In vivo analysis of autophagy in response to nutrient starvation using transgenic mice expressing a fluorescent autophagosome marker. *Mol Biol Cell* 15(3):1101-1111.
72. Komatsu M, et al. (2007) Homeostatic levels of p62 control cytoplasmic inclusion body formation in autophagy-deficient mice. *Cell* 131(6):1149-1163.
73. Flynn J, Tsenova L, Izzo A, & Kaplan G (2008) Experimental animal models of tuberculosis. *Handbook of tuberculosis: immunology and cell biology*, eds Kaufmann S & Britton W (Wiley-VCH, Weinheim), pp 389-4226.
74. Talaat A M, Lyons R, Howard S T, & Johnston S A (2004) The temporal expression profile of *Mycobacterium tuberculosis* infection in mice. *Proceedings of the National Academy of Sciences of the United States of America* 101(13):4602-4607.
75. Zahrt T C & Deretic V (2001) *Mycobacterium tuberculosis* signal transduction system required for persistent infections. *Proc Natl Acad Sci USA* 98(22):12706-12711.

Example 2

Figure 9:
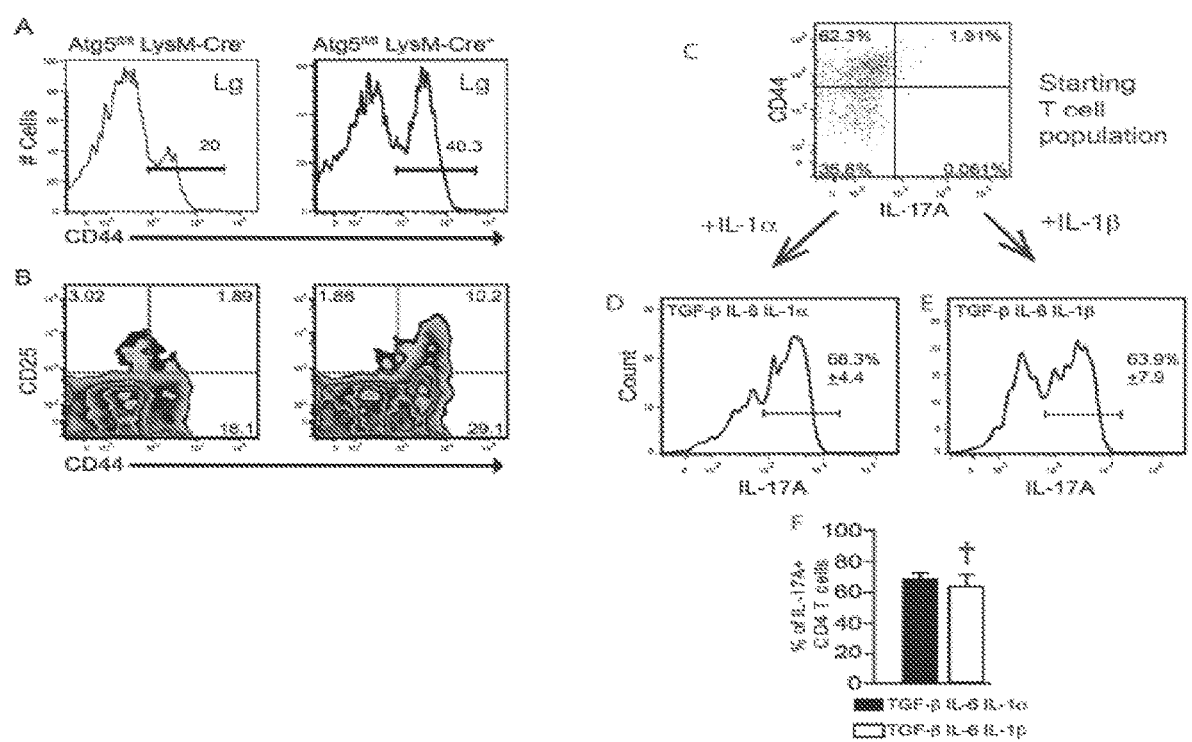
FIG. 9. T cell activation state and IL-1α role in T cell IL-17 polarization. (A,B) CD44 and CD25 expression on CD4 T cells from lungs of uninfected Atg5fl/fl LysM-Cre and Cre+mice. (C-F) Intracellular IL-17A production (day 4; release blocked with monensin) by naïve CD4 T cells polarized in the presence of cytokine cocktails: 5 ng/ml TGF-β and 20 ng/ml IL-6, plus 20 ng/ml IL-1α or 20 ng/ml IL-1β. Dot plot (panel C), levels of IL-17A in unstimulated cells (starting material). Histograms (D,E), IL-17A in naïve CD4 T cells polarized in the presence of TGF-β, IL-6 and IL-1α (panel D) or TGF-β, IL-6 and IL-1β (panel E). (F) Percent of IL-17A+CD4 T cells under respective polarizing conditions. Data: mean±SE; † p>0.05 (t test; n≥3).

GRASPs and Secretory Autophagy
In the model shown in FIG. 8A, the secretory and degradative autophagosome precursor domains on the ER are interrelated. They originate from the secretory aspect of ER oriented towards the Golgi known as the ER-Golgi-intermediate compartment, vesicular-tubular clusters, transitional ER (tER), or ER exit sites (79A,80A). Our preliminary data indicate that GRASP55 relocalizes to sites on the ER marked by WIPI2 (one of the four mammalian Atg18 paralogs) (FIG. 9A).

We hypothesize that mammalian GRASPs play a role in organizing/tethering these precursors at or in the vicinity of the tER sites into larger structures (omegasomes), which in turn lead (69A) to the formation of autophagic membranes for secretion and degradation end-purposes. This idea is based on: (i) the known translocation of GRASP from the Golgi during induction of autophagy observed in our published work (27A); (ii) the known mechanisms of how GRASP tethers membrane domains into larger structures through intermolecular homotypic oligomerization of GRASP 81,82; and (iii) the control of GRASP oligomerization by protein kinases (e.g. during mitosis) (81A,82A).

It is determined whether autophagy regulators such as Ulk1 and Ulk2 control redistribution of GRASP to the vicinity of tER sites. Furthermore, GRASP interacting partners may change, and this may permit coalescence of precursors into omegasomes. Whether the resulting omegasomes specialize in degradative or secretory autophagy may depend on the subsets of (at present seemingly redundant) early autophagic factors, e.g. Ulk1 vs Ulk2 and four different variants of mammalian Atg18s represented by WIPI-1, -2, -3 and -4. Our preliminary data with GRASP55 relocalizition to sites on the ER marked by WIPI2 (FIG. 9A) indicate that this happens both during starvation-induced autophagy and starvation-induced secretory autophagy (for the latter, the cells are also treated with nigericin to activate inflammasome and trigger extracellular release of IL-1 (27A)).

There are two types of factors that we expect to control GRASP55 localization during degradative and secretory autophagy: (i) kinase(s) that may affect GRASP55 homo-oligomerization state and thus tethering of adjacent membranes (as in the Golgi ribbon); and (ii) compartment-specific interacting partners binding to GRASPs' PDZ domains thus tethering them to the appropriate membranes that eventually coalesce. GRASPs have the ability to link membranes through their homotypic interactions between PDZ domains and internal PDZ-binding motifs ("internal ligand") (see FIG. 8A, top). This is morphologically best recognized in the formation, maintenance and disruption of Golgi ribbons, where GRASPs already play a role in linking of Golgi cistrenae (81A,82A) (FIG. 8A). The ability of GRASPs to undergo homo-oligomerization depends on the phosphorylation state of their Ser-Pro-rich C-terminal domains and can be disrupted e.g. during mitosis (causing Golgi dispersal) following complex phosphorylation patterns by several kinases including ERK, CDK1 and PLK1 (81A,82A). In our model, Ulk1 or Ulk2 are the main kinase candidates for modulating GRASP55 translocation following induction of degradative or secretory autophagy in our system.

Example 3

Common Versus Specialized Precursors for Secretory and Degradative Autophagy
Experiments and Interpretations.
Ulk1 and Ulk2 as well as WIPI1, 2, 3 and 4 are knocked down and outputs of degradative and secretory autophagy are measured. The physiological outputs of secretory autophagy measured are IL-1β and HMGB1 in culture supernatants (27A). For degradative autophagy, proteolysis of stable proteins is measured as we have previously described (83A), mitochondrial cellular content and quality by MitoTracker Green and Red, microbial killing using our published procedures (84A), and p62 degradation by immunoblotting and high content microscopy quantification (85A). Differences in effects in the two categories are normalized to each other, anticipating reciprocal relationships. Our cells of choice are the primary murine bone marrow-derived macrophages (BMM), since we know fully the parameters of both processes from our published studies on secretory autophagy (27A) and degradative functions of autophagy (83A,85A,86A). Ulk1 and Ulk2 are targeted (seemingly redundant Atg1 orthologs in mammals) and WIPI1,2,3 and 4 (four Atg18 paralogs in mammals) with the idea that perhaps they may specialize. Two mammalian GRASPs, GRASP55 and GRASP65 are compared (FIG. 7A) for potentially differential roles in degradative and secretory autophagy.

Alternatives.
Conceptual.

Differential effects on degradative vs secretory autophagy upon knockdown of a given factor will be taken as specialization. Of course, absence of differential effects will not rule out specialization or divergence at a downstream point or points, which will be addressed at different steps below.

Technical.

We could not efficiently knock out GRASP65 in macrophages, and have observed only a minor synergistic effect with GRASP55 (but not GRASP65 alone) on IL-1β secretion (27A). An attempt to overcome this problem is made by using shRNA approaches. As an alternative to siRNA and shRNA knockdowns, TALEN (Transcription Activator-Like Effector Nucleases) knockout cell lines are generated (87).

Example 4

GRASP Translocation: Interacting Partners and Kinases.
Experiments and Interpretations.

myc-Ulk1 and myc-Ulk2 wild type are employed, along with their equivalents to substrate trapping KR mutants 88. These constructs are used to test whether GRASP55 associates with Ulk1 or Ulk2. Duolink or PLA assay are used (proximity ligation I in situ assay) to establish any transient interactions between suspect kinases (e.g. Ulk1) and GRASP. The Duolink (PLA) method (see FIG. 10A) has been invented specifically for capture and detection of such transient protein-protein interactions in whole cells (89A). As already preliminarily stated above, an example of Duolink/PLA from our recently published paper (85A) on Rab8b-TBK-1 interactions is given in FIG. 10A. In the Duolink/PLA approach, stable and transient protein-protein interactions are detected as fluorescent dots 89A. A PLA fluorescent dot is a binary visual output (signifying positive interaction) of a spatially-restricted rolling circle DNA amplification event, which can occur only in locations where successful circularization or ligation took place between the connector oligonucleotides and primers covalently linked to antibodies. The signal is generated only when the secondary antibodies recognize in-coincidence binding of primary antibodies to two proteins interacting within a cell at a range approximating fluorescence resonance energy transfer distances (89A). For experiments reported here, fixed BMM were incubated with primary antibodies followed by Duolink/PLA probes. After ligation, rolling circle amplification, and hybridization with fluorescent nucleotides and counterstaining of nuclei with DAPI, red fluorescent dots are imaged and quantified.

The Ulk-dependent phosphorylation of GRASP is tested using protein chemistry methods as described in detail in our recent publication (85A) of TBK-1-dependent p62 phosphorylation. We postulate that Ulk1 or Ulk2 phosphorylate GRASP55 following induction of degradative or secretory autophagy to allow its translocation to the Sec23+ structures that are conventionally considered to be ER exit sites but in the case of degradative or secretory autophagy are specialized sites in the ER leading to the formation of omegasome/CUPS (FIG. 8A). This is paralleled by functional assays measuring IL-1β and HMGB1 secretion from cells knocked down for Ulks. Complementary to these experiments, we have generated mutants of GRASP55, fashioned after GRASP55 S441A mutant (human S441 and mouse S443). These presumptive phosphorylation sites (in our model for Ulk1/2) are key for activation of GRASP in stimulating unconventional membrane protein trafficking (CFTR) (28A). 293T cells are transfected with GRASP55 wild type and S443A mutant and assayed to determine the effect on HMGB1 secretion as per our published methods (27A).

In a search for interacting partners that guide GRASP55 translocation to WIPI2-positive structures (autophagosomal precursors; see FIG. 8), co-IPs with GRASP55 are conducted following induction of degradative or secretory autophagy, probing for autophagy initiation complex members in immunoprecipitates. Among our candidate interacting partners are: Sec23 (based on Ohsumi and colleagues, this part of COPII but not Sec13/31 plays a key role in autophagy 90A); Atg9 (the only autophagy specific integral membrane protein that is early on recruited to the autophagosomal initiation sites in mammalian cells 2); FIP200 and VMP1 (believed to be among the first proteins at the sites where Ulk1 and the rest of the autophagic machinery coalesces 2). WIPIs 91 and DFCP-1 69 are included. Positive co-IPs are confirmed using an independent method (Duolink/PLA) designed to detect endogenous protein-protein interactions in whole cells (89A).

Alternatives:

Alternatively to Ulk1 and 2, JNKs and PKR are tested. (i) JNKs, specifically JNK-1 (92A), is already known to result in disinhibition of Beclin-1 activation of autophagy (92A). Of interest for our model is that JNKs are know to act downstream of IRE1 following ER stress and unfolded protein response (UPR) (93A). UPR has been already linked to induction of autophagy 77. The role of JNKs is tested using JNK1 and 2 knockout MEFs, IRE1 and JNK expression constructs, and JNK inhibitor SP600125 with the idea that the IRE1-JNK axis leads to phosphorylation and changes in GRASP55 localization/activities and to IL-1β or HMGB1 secretion following ER stress (e.g. with thapsigargin, tunicamycin, DTIT, 2-deoxyglucose). (ii) PKR has recently been linked (94A) to extracellular release of HMGB1, one of the autophagy-dependent unconventionally secreted cargos (27A). The PKR substrates identified thus far are components of inflammasome (e.g. NLRP3) (94A). HMGB1 release has been linked to inflammasome activation upstream of unconventional secretion (27A). This is fully compatible with our findings that inflammasome and autophagy-dependent unconventional secretion cooperate in mammalian cells, as an evolutionary adaptation in higher organisms (17A,27A). Consequently, PKR phosphorylates and changes GRASP localization are tested and is determined whether these effects may be responsible for the previously reported links between PKR and autophagy (95A).

Example 5

Omegasome/CUPS Formation.
Experiments and Interpretations.

Morphometrically (imaging) and biochemically (subcellular fractionation) quantify GRASP55 translocation to the WIPI-positive profiles (for initiation of degradative or secretory autophagy) in kinase knockdown or inhibition assays. Several methods are used to monitor GRASP55-dependent coalescence, including measuring the area of WIPI (FIG. 9A) and DFCP-1 profiles (DFCP1 is the distinguishing marker for omegasome (69A)) using Cellomics HSC algorithms that can quantify in a fully automated and unbiased mode (from acquisition to processing) large number of profiles, routinely set as in flow cytometry to gather data until a threshold (e.g. 5,000 analyzable events) per sample has been reached (85A). GRASP effect upon phosphorylation (e.g. by Ulk1) is tested; instead of normally tethering Golgi cisternae, now tethers multiple ER exit sites coalescing them into omegasomes, the large precursors to degradative and secretory autophagosomes (FIG. 8A).

Alternatives:
Conceptual. (i) Indirect GRASP-Induced Effects Model.

As an alternative to the model in which GRASP55 translocates and plays an active role in tethering and coalescing ER exit site-associated omegasome/CUPS precursors (FIG. 7A), a passive/indirect role for GRASP55 is considered: GRASP phosphorylation may disrupt Golgi structures to the extent that it indirectly causes backing up of membrane flow at ER exit sites thus increasing their chance to coalesce. The distinguishing feature between the passive and active models is where GRASP55 localizes at the time of induction of degradative or secretory autophagy: if GRASP55 remains associated with the dispersed Golgi or its ministacks following starvation or ER stress, then the passive model is more likely. If it is translocated in the vicinity of well-defined ER exit sites or ER-associated omegasomes/CUPS, then the active model is likely. Biochemically, we should also be able to detect a switch to new binding partners if the active GRASP-relocalization model is correct, and retention of binding partners and loss of homotypic interactions if the passive model is correct. (ii) Role for Atg9 and Atg9 isoforms (Atg9L1 and Atg9L2)? Atg9 is the only integral membrane autophagy protein 2. Atg9 has been shown to affect unconventional secretion of Acb1 in yeast (24A). Yeast GRASP (Grh1) and Atg9 overlap upon induction of autophagy that leads to Acb1 unconventional secretion (25A). According to Y. Ohsumi's latest work (75A), autophagosomal structures are formed or expanded in yeast by fusion of small Atg9 vesicles derived from the Golgi. This can be linked back to the observations by S. Tooze and colleagues in mammalian cells whereby Atg9 was found to redistribute from TGN to nascent autophagosomes upon induction of autophagy (73A). It is determined whether knockdown of mammalian Atg9L1 affects secretory autophagy of IL-1β. (iii) Roles for COG and TRAPP A potentially related question is how do other protein complexes in the secretory pathway (between the ER and the Golgi and within the Golgi) including factors affecting tethering and vectorial transport such as TRAPP 97,98 and the COG complexes (74A) fit into the above model. Both TRAPP and COG (97A,98A) affect canonical autophagy (74A). It is determined whether TRAPP and COG complexes affect secretory autophagy. It is determined whether TRAPP or COG components interact with GRASP as it moves to form autophagosomal precursors.

Technical.

Additional morphological (EM), fluorescence (e.g. FRET, fluorescence intensity), and biochemical/subcellular fractionation of membranous organelles based assays will be employed as needed.

Example 6

Specialization and Selectivity Factors for Secretory Autophagy
Rationale.

The determinants of selectivity for secretory and degradative autophagy are defined. There are multiple mammalian Atg8 paralogs and multiple autophagic adaptors. Both of these groups represent candidates for selectivity and specialization. There are six mammalian Atg8s (LC3A, B and C, and GABARAP, GABARAPL1 and L2) whose potential functional differences are not well-understood (47A,99A) and may reflect selectivity and specialization for secretory versus degradative autophagy. It is determined whether adaptors that capture autophagic cargo destined for secretion differ from the adaptors that capture cargo earmarked for autophagic degradation. There is now considerable information available regarding the adaptors for degradative autophagy. For example, p62, NDP52, and optienurin, have been shown to find ubiquitinated cargo tagged for elimination, be it a whole pathogen 13,100,101, a protein aggregate, mitochondrion, and another cytoplasmic target (86A,102A,103A). NBR1 102 has yet to be assigned a clearly identified function. Another source of selectivity can be post-translational modifications of adaptors, which are known to modify interactions either between the adaptors and the cargo (85A,104A) or between the adaptors and Atg8/LC3 factors (100A).

Figure 10:
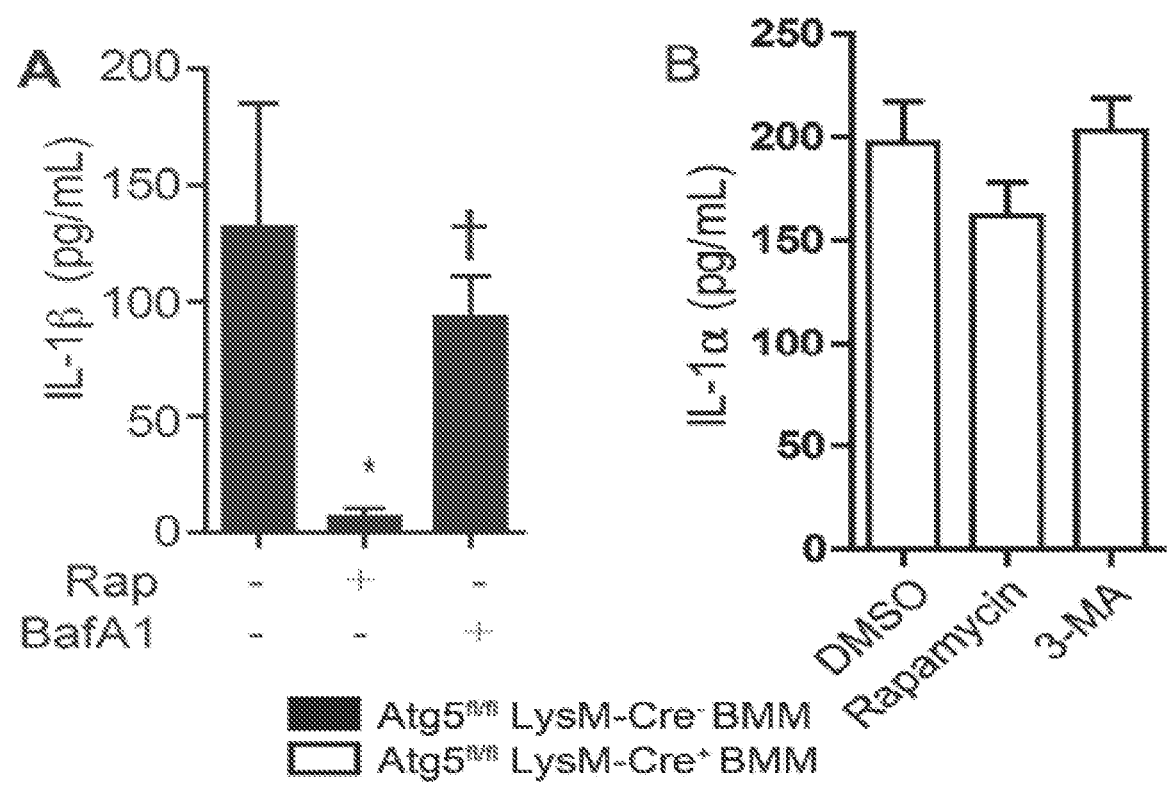
FIG. 10. Controls for pharmacological induction of IL-1α hypersecretion phenotype in autophagy-competent macrophages. These experiments were carried out as a controls for effects of pharmacological induction of autophagy on IL-1α secretion shown in FIG. 5F. IL-1β secretion was examined in autophagy-competent Atg5fl/fl LysM-CreBMM and IL-1α secretion was measured in autophagy-deficient Atg5fl/fl LysM-Cre+ BMM. (A) IL-1β (ELISA) released from Atg5fl/fl LysM-CreBMM (identical activation as in FIG. 5F) treated with (A) 50 mg/ml rapamycin (Rap) and 100 nM Bafilomycin A1 (Baf A1) after 12 h of stimulation. (B) IL-1α (ELISA) released from Atg5fl/fl LysM-Cre+ BMM (identical activation as in FIG. 5F) in the presence of (A) 50 mg/ml rapamycin (Rap) and 10 mM 3-MA after 12 h of stimulation. Data: mean±SE; *, p<0.05; † (or no symbol) p>0.05 (t test; n≥3).

The potential existence of new, previously uncharacterized adaptors specializing in secretory autophagy is considered. Finally, a potential for specialization is determined for exocyst components and Rab8 isoforms (Rab8a vs Rab8b). Based on our published data with two Rab8 isoforms, Rab8a 27 vs. Rab8b 85, and based on work by others (59A) and reported observations by us (27A) regarding exocyst components, it appears that these systems participate in one but not the other type of autophagy, with an appreciable degree of selectivity for the degradative or secretory form. The small Rab GTPases act as pivotal regulators of membrane trafficking (105A). We have found in a series of studies that Rab8 isoforms (there are two: Rab8a and Rab8b) affect both secretory 27 and degradative autophagy (85A). The published data suggest specialization, with Rab8b being more important for degradative autophagy 85 whereas Rab8a affects secretory autophagy (27A). Rab8b binds to TBK-1 directly as shown by Duolink (FIG. 10A). Optineurin binds to both Rab8a and Rab8b 106 as well as to TBK-1 107 but apparently is not needed for Rab8b-TBK-1 association (85A). These relationships are examined as potential sources of specialization and selectivity for secretory vs. degradative autophagy.

Example 7

Role and Specialization of LC3/GABARAP Paralogs.
Experiments and Interpretations.

Figure 11:
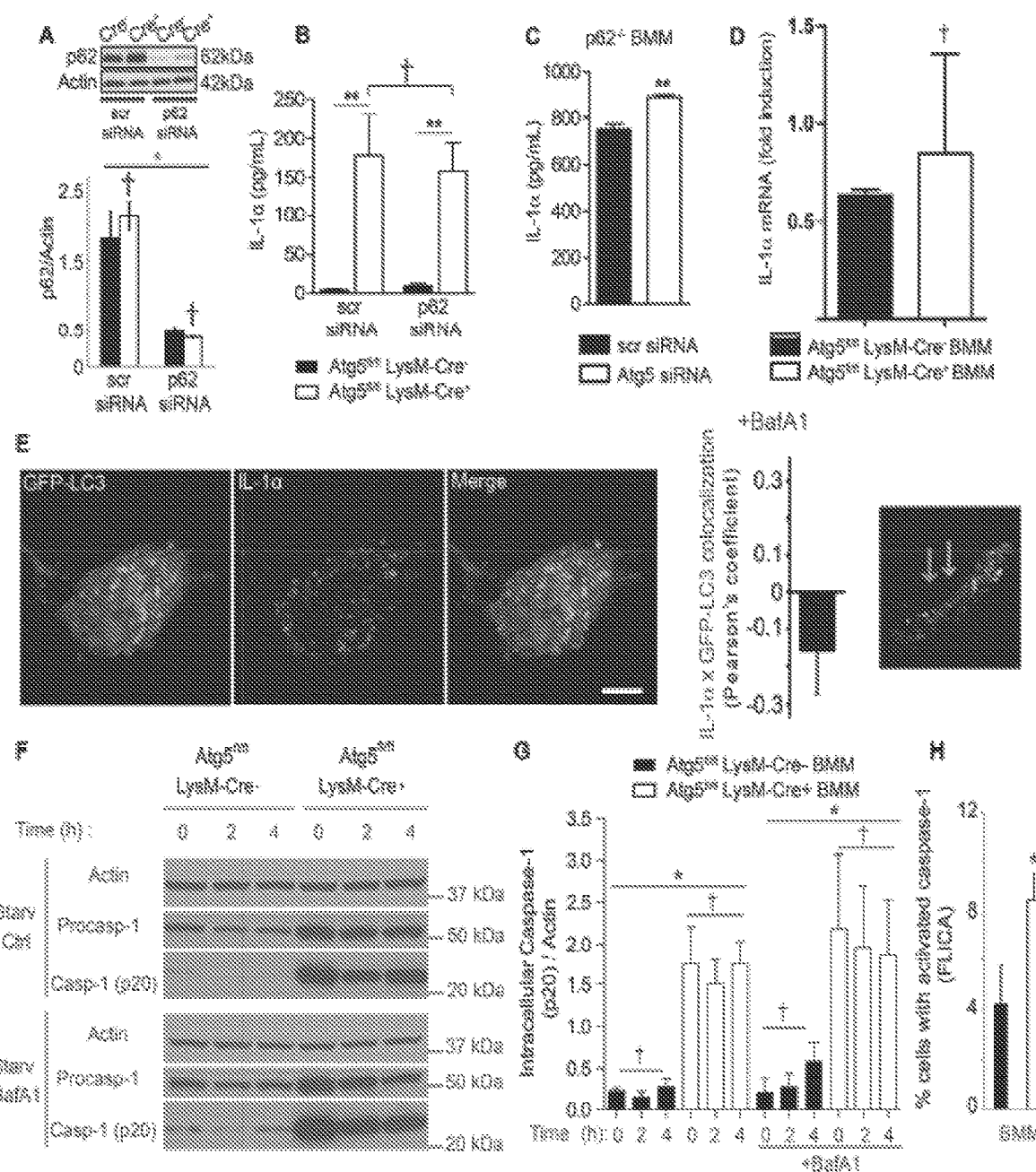
FIG. 11. Analysis of p62, autophagosomes, and caspase 1 as potentially contributing factors to the IL-1 hypersecretion phenotype in Atg5fl/fl LysM-Cre+ macrophages. (A) Immunoblot assessment of p62/sequestosome 1 knockdown in BMM. (B) IL-1α release from Atg5fl/fl LysM-Cre+ BMM (stimulated with LPS and IFN-γ) subjected to p62/sequestosome 1 knockdown (p62 siRNA) relative to siRNA control (scr, scramble). (C) IL-1α released from LPS and IFN-γ stimulated BMM from p62−/− knockout mice treated with Scr (scrambled control) or Atg5 siRNA. (D) Transcriptional analysis (QTRT PCR) of IL-1α gene expression. Total RNA was isolated from Atg5fl/fl LysM-Cre and Cre+ BMM using RNeasy kit (Qiagen) and cDNA was generated using QuantiTect Reverse Transcription kit (Qiagen). (E) Confocal microcopy analysis of IL-1α colocalization relative to LC3 in GFP-LC3 expressing BMM induced for autophagy by starvation (EBSS) in the presence of bafilomycin A1 for 90 minutes. Scale bar, 5 μM; Pearson's colocalization coefficient for IL-1α vs. LC3. (F) Caspase 1 activation in the absence of autophagy. Atg5fl/fl LysM-Cre− or Cre+ BMM cells were starved (EBSS) with or without bafilomycin (BafA1) for 2 or 4 h and subjected to immunoblot analysis; Procasp-1, procaspase 1; Casp-1 p20, processed (activated) caspase 1. (G) Quantification of p20 bands from blots as in A, relative to actin. (H) Atg5fl/fl LysM-Cre− or Cre+ BMM were stimulated with LPS overnight and caspase-1 activity was assessed by flow cytometry using the FLICA caspase-1 reagent. Data, mean±SE; *p<0.05, **p<0.01 and † p>0.05 (t test; n≥3).

It is determined whether there is a specific LC3 and a specific GABARAP specializing in secretory autophagy. Our preliminary data support this notion, based on differential effects of mammalian Atg8 knockdowns on IL-1β secretion (FIG. 11A). Biochemical (protein-protein interactions) and subcellular fractionation analyses is conducted to confirm the theory. It is also determined whether secretory autophagy-specific mammalian Atg8 (e.g. LC3A) interacts with secretory autophagy-specific adaptors or post-translationally modified adaptors (as depicted in FIG. 8A). Furthermore, LC3B may differentially co-fractionate with membranes containing cargo destined for degradation (e.g. ubiquitinated proteins, mitochondria, bacteria, polyQ-huntingtin, p62) vs LC3A's cofractionation with cargo destined for unconventional secretion. We often think of mammalian Atg8s as a uniform group of nearly identical factors that are commonly referred to as simply "LC3". The human and mouse genomes encode three LC3 variants (LC3A, LC3B—the most popular variant, and LC3C) and three GABARAP variants (GABARAP, GABARAPL1 and GABARAPL2). In fact, different members of the mammalian Atg8 family are more divergent from each other (LC3s differ by close to 50% and GABARAPs are below 40% identical) than ubiquitin and NEDD, and yet nobody equates NEDD with ubiquitin. Thus, different LC3s and GABARAPs are not a uniform group of redundant proteins and they are unlikely to have identical function. The divergence in functions among different LC3s and GABARAPs have been studied (47A, 99A).

Alternatives:

Recent work by Z. Elazar and colleagues (47A, 99A) has indicated that LC3 as a group specialize in elongation of autophagosomes whereas GABARAPs may be more important for autophagosome closure. It is determined whether a combination of an LC3 and a GABARAP (based on our preliminary results in FIG. 11A, possibly LC3A and GABARAP) exists to form a secretory autophagic organelle.

Example 8

Specialization of Cargo Adaptors.
Experiments and Interpretations.

Figure 12:
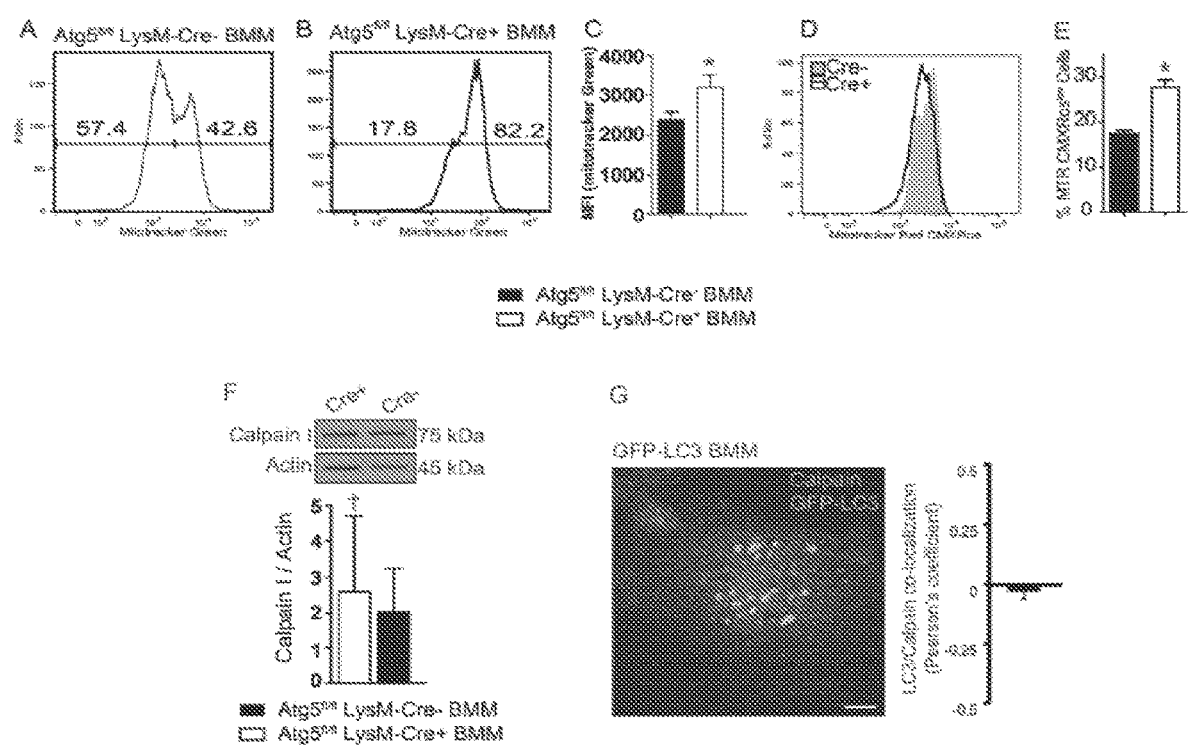
FIG. 12. Analysis of mitochondrial content, mitochondrial polarization state, calpain levels, and calpain localization relative to autophagic organelles in Atg5fl/fl LysM-Cre+ macrophages. (A-C) Flow cytometry analysis of cellular mitochondrial content in Atg5fl/fl LysM-Cre− and Cre+ BMM stained with MitoTracker Green. A and B, histograms; C average mean fluorescence intensity (MFI) of MitoTracker Green per cell. (D,E) Polarization state of mitochondria in Atg5fl/fl LysM-Cre− and Cre+ BMM. (D), Overlay histogram, MitoTracker Red CMXRos in Atg5fl/fl LysM-Cre− and Cre+ BMM. (E), Data and statistical analysis of cumulative results represented in D. (F) Immunoblot analysis of calpain I in unstimulated Atg5fl/fl LysM-Cre− or Cre+ BMM and quantification of calpain relative to actin. (G) Calpain does not colocalize with the autophagosomal marker LC3. Confocal microscopy image of endogenous calpain I (Capn1) and immunofluorescently (anti-GFP) labeled GFP-LC3 in BMM from GFP-LC3 knock-in mice. Scale bar, 10 μm. Graph, Pearson's colocalization coefficient (n=3) between calpain I and LC3 (note the negative value). Data, mean±SE, *p<0.05, † p>0.05 (t test; n>3).
Figure 13:
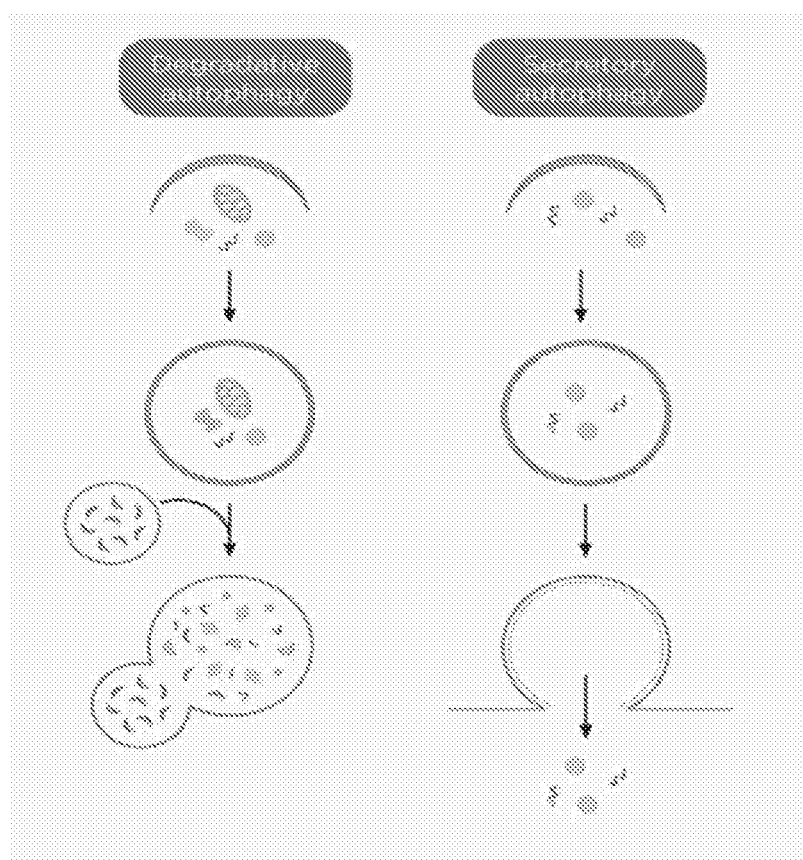
FIG. 13. Degradative (canonical) vs. secretory autophagy. Left: Canonical autophagy digests cytoplasmic proteins following fusion with lysosomes. Right: Secretory autophagy is a form of unconventional protein secretion.
Figure 14:
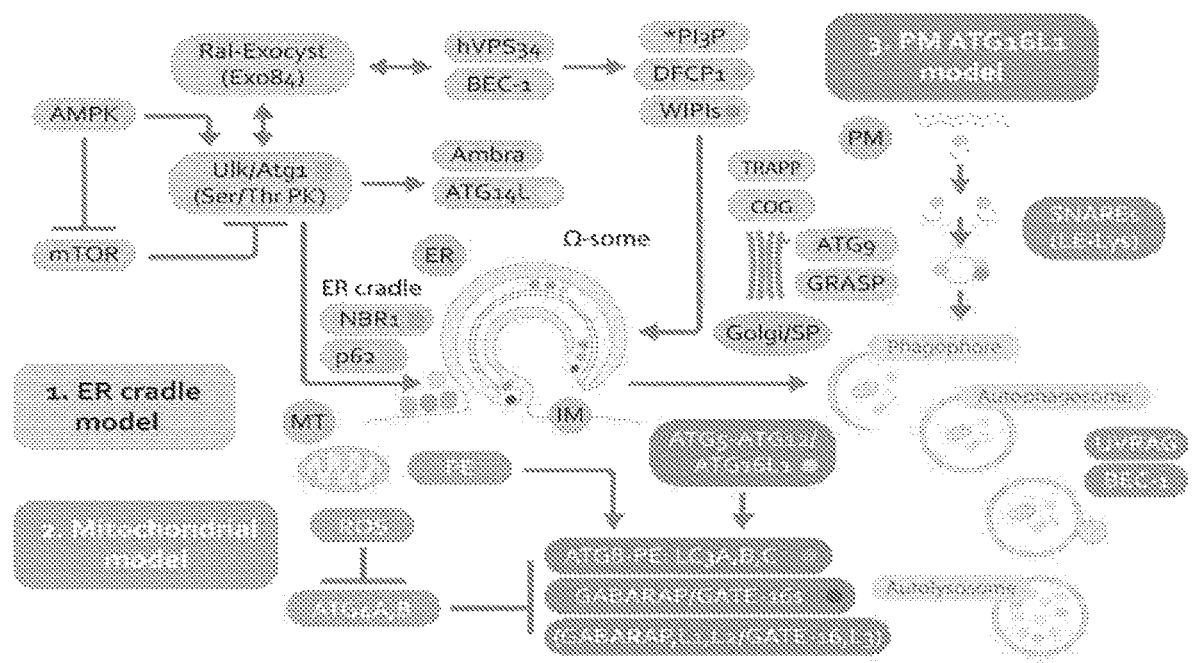
FIG. 14. Three models of the autophagy pathway, as explained further hereinafter.
Figure 15:
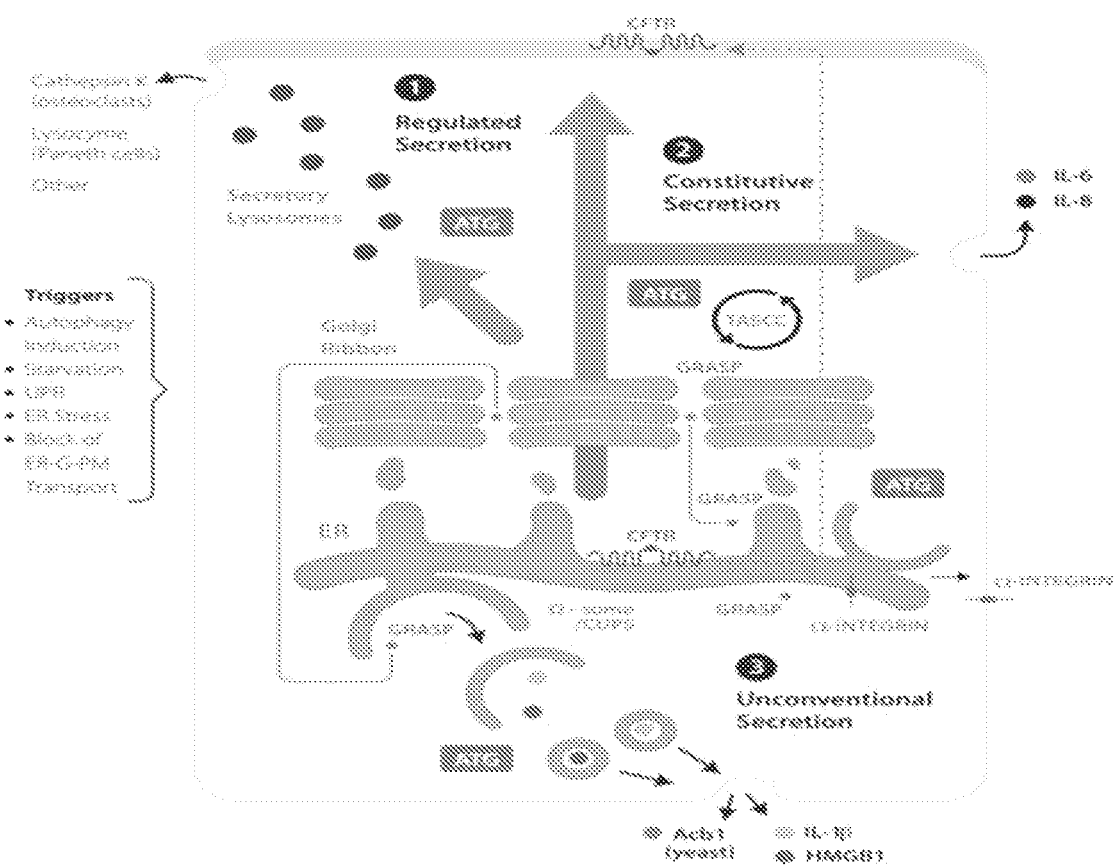
FIG. 15. Role of autophagy in conventional and unconventional secretion, as explained further hereinafter (from *Trends in Cell Biology*[1]).
Figure 16:
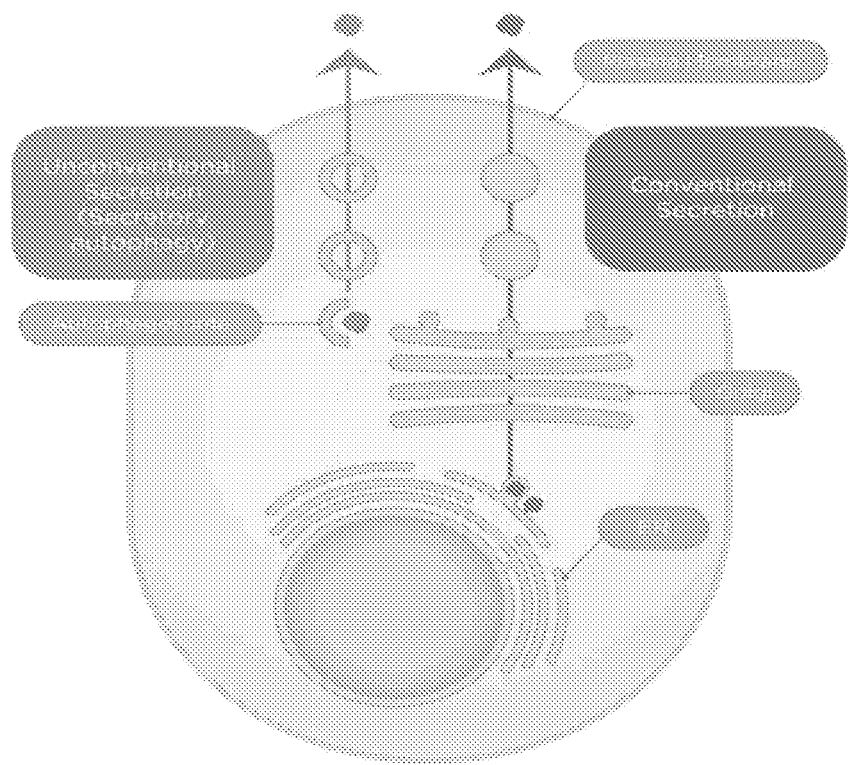
FIG. 16. The well-developed paradigm of conventional protein secretion through endoplasmic reticulum (ER), Golgi and post-Golgi trafficking (right arrow) versus autophagy-dependent unconventional secretion of cytosolic proteins (secretory autophagy) (left arrow), as explained further hereinafter.
Figure 17:
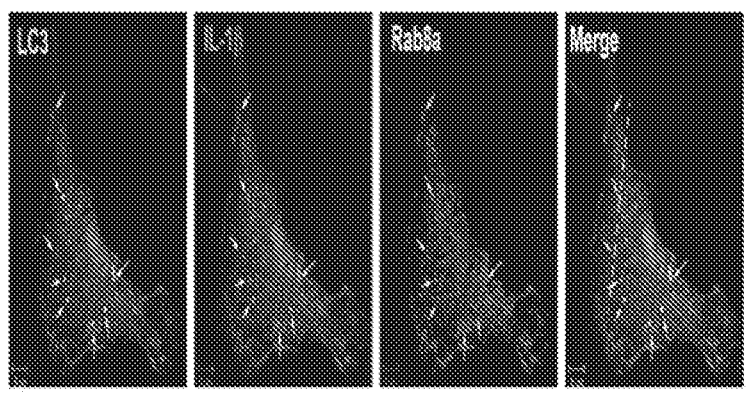
FIG. 17. IL-1β and LC3 colocalize in macrophages.
Figure 18:
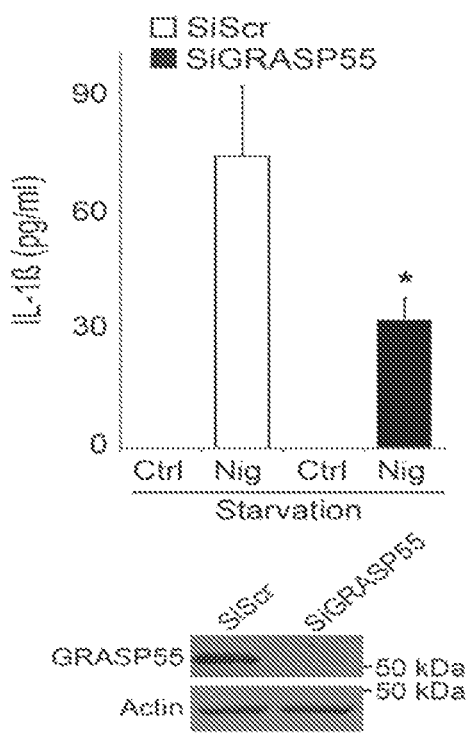
FIG. 18. GRASP55 affects IL-1β secretion under autophagy inducing conditions (starvation). Nig, nigericin (inflam-masome agonist).
Figure 19:
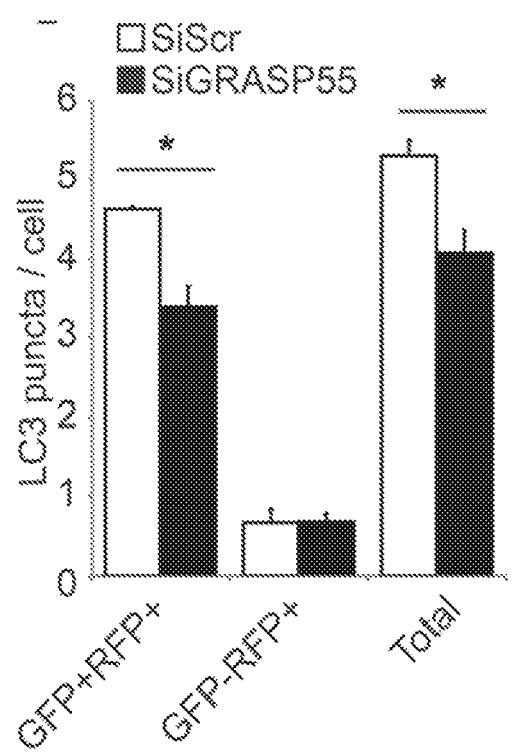
FIG. 19. GRASP affects canonical autophagy.
Figure 20:
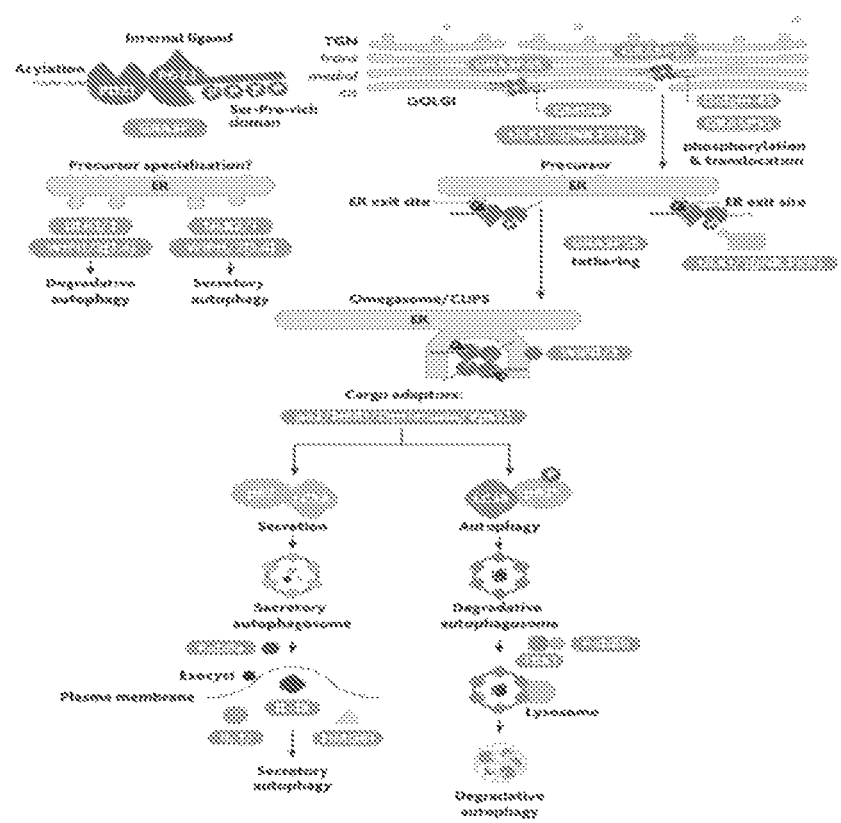
FIG. 20. The model and proposed points of divergence between degradative and secretory autophagy.
Figure 21:
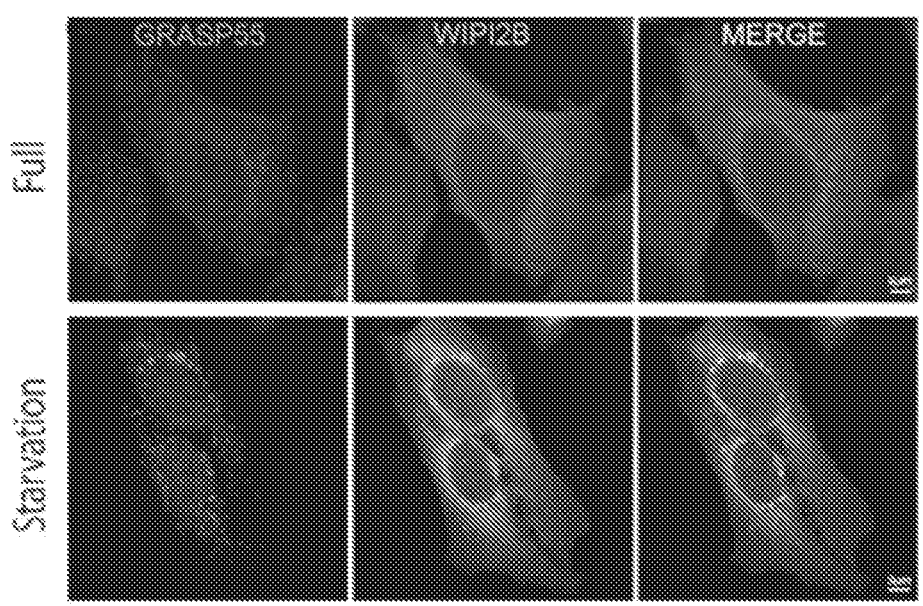
FIG. 21. Relocalization of GRASP55 to WIPI2 (mAtg18) profiles upon induction of autophagy or autosecretion.
Figure 22:
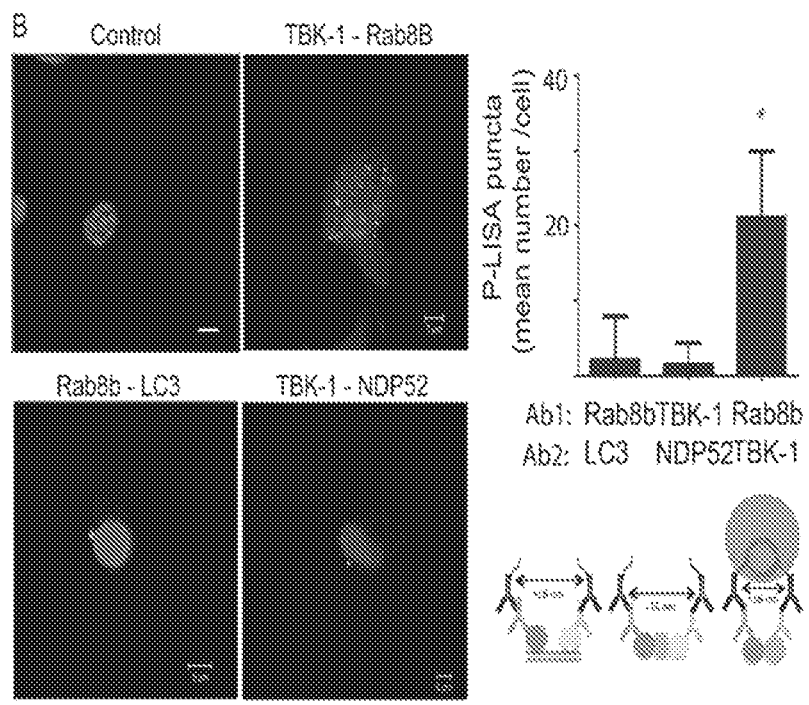
Figure 23:
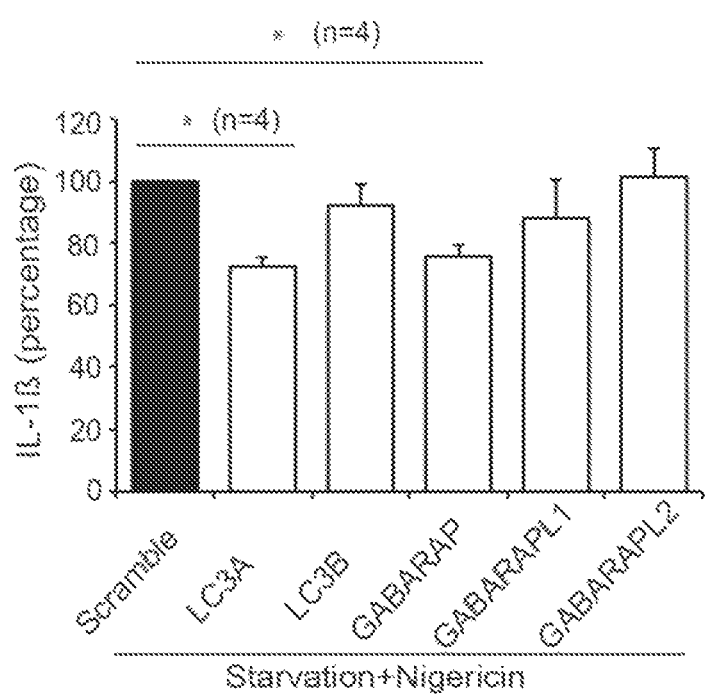
FIG. 23. Role of mammalian Atg8 (LC3s and GABA-RAPs) in autosecretion.
Figure 24:
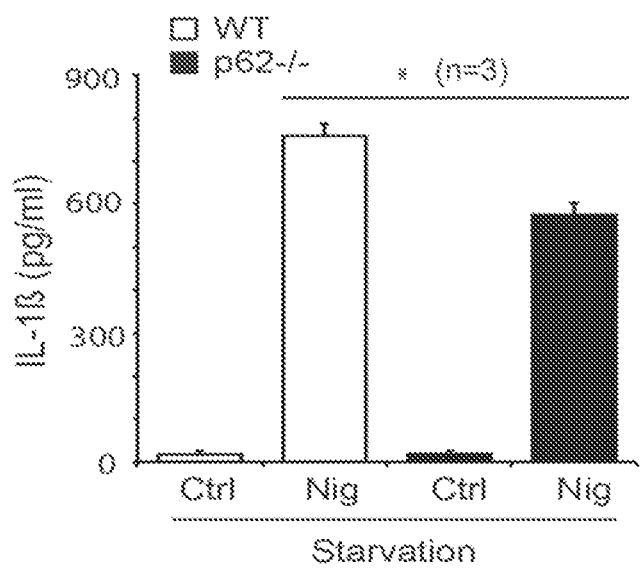
FIG. 24. Loss of autophagic adaptor p62 reduces IL-1β autosecretion.
Figure 26A:
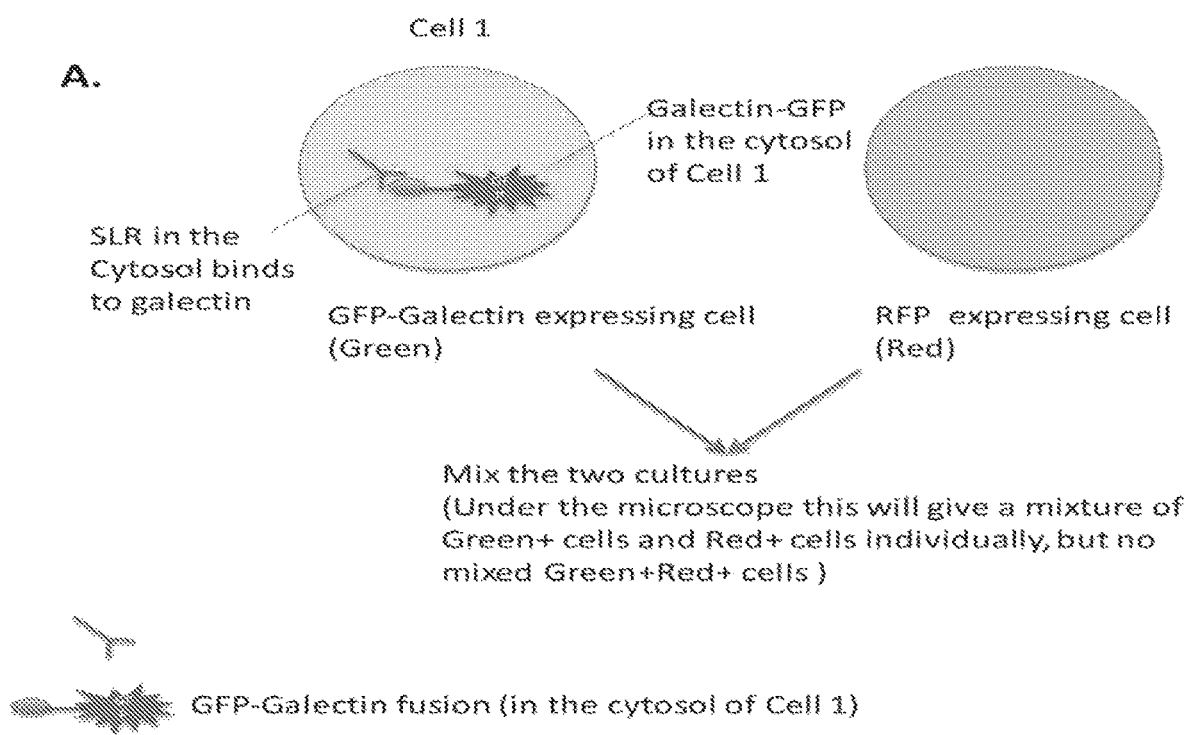
FIG. 26A shows the two populations of cells, the first of which expresses sequestome-like receptor in the cystosol which binds to galectin and a galectin-GFP fusion protein and secretes the galectin when the cell is exposed to an inducer of autophagy secretion.
Figure 26B:
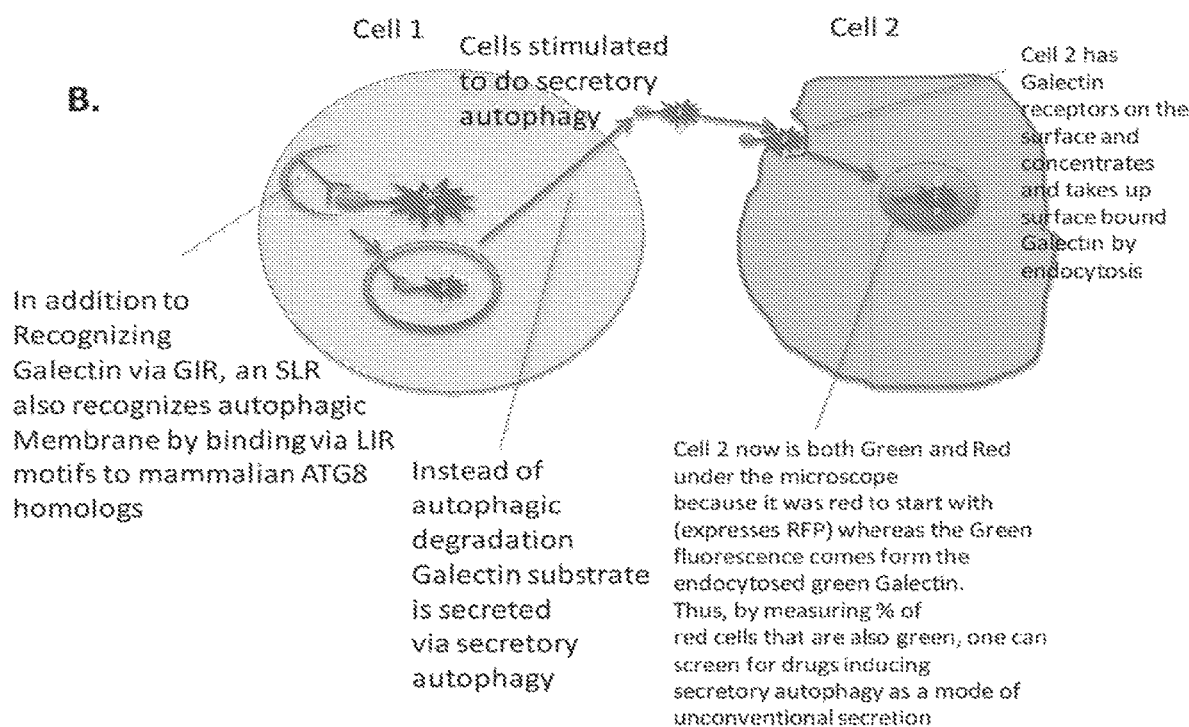
As shown in FIG. 26B, the second population of cells, which expresses red fluorescent protein, has surface galectin receptors which bind the galectin-GFP secreted from the first population of cells and concentrate and take up the galectin-GFP into the cell. In the presence of an autophagy inducer, the red fluorescent cells also emit green fluorescence which can be identified and quantitated. In addition, in the presence of an inducer, the green fluorescence in the first population of cells will often be reduced. In the presence of an autophagy inhibitor, the red fluorescent cells remain unaffected or increase (depending on the autophagy secretion which occurs for the control) and the fluorescence in the first population of green fluorescent cells will remain unaffected or increase (also depending on the autophagy secretion which occurs for the control. By comparing the fluorescence emitted by the cells compared to the control, a determination can be made as to the activity of a compound with unknown activity as an inducer or inhibitor of autophagy secretion or a compound with no activity.

Specific autophagic adaptors are examined to determine whether the cargo (and autophagic organelle) is destined for secretory or degradative functions. NBR1, p62, NDP52, and optineurin are knocked-down, or knockout cells are used (e.g. BMMs from the p62$^{-/-}$ mice received from M. Komatsu). IL-1β secretion is measured. Of note, NBR1 (102A), despite being the closest homolog of p62 has yet to be assigned a clearly defined function. Thus, it is knocked down and tested to determine whether it may specialize in autosecretion (measuring IL-1β and HMGB1). Although p62/sequestosome 1 would seem as the least likely candidate (since all the reports to date have been focused on p62 in autophagic degradation), our preliminary data using macrophages from p62−/− knockout mice suggest that it may be engaged in secretion of IL-1β (FIG. 12A). It is determined whether this effect is due to p62 alone or p62 interactions with NBR1, by overexpressing mutant form of p62 (PB1 domain dual point mutation K7A,D69A precludes oligomerization with NBR1).

Whether post-translational modifications of autophagic adaptors determine or modulate destination of their cargo for degradative or secretory autophagy is also determined. We have reported the presence of multiple phospho-peptides in p62 85. A determination of whether these patterns change during secretory autophagy versus degradative autophagy is made by comparing p62 phospho-petidome in immunoprecipitates form starvation alone versus starvation+nigericin treated cells. As shown by us and others (85A,104A), phosphorylation of at least one of the Ser residues (pSer-403) modulate p62's ability to bind to ubiquitinated substrates. Our data show that TBK-1 (85A) can phosphorylate Ser-403 in p62, whereas the Nukina laboratory reported that this site in the p62 UBA domain is phosphorylated by CK2 (104A). Both studies show that this is a requirement for ubiquitinated cargo-recognition and clearance. Whether some of that clearance is not only by degradation but may involve secretion (as we and others have detected p62 in cell culture supernatants) is determined. Furthermore, our published data (85A) indicate that, in cells lacking TBK-1, p62 undergoes additional large post-translational modifications and does not enter into degradative pathways (85A). the nature (by mass spectrometry) of these post-translational modifications (detectable only in TBK-1-negative cells) is determined using the methods and materials collected for our just published work 85. We will also knockdown and pharmacologically inhibit TBK-1. Our preliminary studies with TBK-1 inhibitor BX795 show that IL-1β secretion is reduced. It is determined whether TBK-1 knockout MEFs 85 secrete less HMGB1 (MEFs are not suitable for IL-1β secretion studies, so extracellular HMGB1 will be measured instead).

Alternatives:

(i) Optineurin is also an autophagic adaptor 100, and since it binds to TBK-1 it is of interest. TBK-1 phosphorylates optineurin and increases its affinity for LC3B and enhances its capacity for cargo delivery to autolysosomes (100A). It is determined whether optineruin directs its cargo to secretion in TBK-1 null (or inhibited) cells. (iii) Previously uncharacterized secretory autophagy adaptors may exist. Vps23/TSG101 is examined. CUPS structures in yeast have been shown to contain Vps23 25, the equivalent of mammalian TSG101. The significance of Vps23's presence in CUPS is not known and it is curious that other ESCRT proteins are not found in CUPS 25. Vps23, as a part of the ESCRT-I complex, is involved in multivesicular endosomal sorting but also plays other cellular roles 108. Although Vps23 is required for Acb1 unconventional secretion in yeast 26, deletion of Vps23 did not affect Grh1+ CUPS formation, suggesting that Vps23 may be a part of the downstream sorting effector functions of CUPS. A possible adaptor role for Vps23PTSG 101 in secretory autophagy is that VPS23/TSG101 in its sorting function binds to ubiquitinated cargo or short peptide motifs. Thus, we may include TSG101 on our list of potential adaptor candidates for secretory autophagy.

Example 9

Roles and Specialization of Rab8a Vs. Rab8b and TBK-1 in Secretory Versus Degradative Autophagy.
Experiments and Interpretations.

A model in which Rab8a does not bind directly to TBK-1 is tested, as opposed to direct Rab8b-TBK-1 interaction (85A). Using co-immunoprecipitations and Duolink assays, it is determined whether or not Rab8a associate with TBK-1, and whether this association is direct (Duolink will provide the resolution sufficient enough to rule out an intermediate adaptor). This will be combined with optineurin knockdowns. Optineurin, being a possible adaptor, might allow Rab8a and TBK-1 to be present in a protein complex but not directly interact, thus showing association by imunoprecipitation but its absence by Duolink. Since interaction with TBK-1 is key for entering the degradative autophagy pathway (85A), an absence of Rab8a interaction with TBK-1 or a different type of association between the two may explain how Rab8a directs autophagic organelles for secretion instead of for degradation in autolysosomes.

Alternatives:

Conceptual.

The exocyst complex (consisting of eight subunits including Sec5, Sec6, and Exo84) has been recently implicated in autophagy (59A). The exocyst is however best known for its function in trafficking of post-Golgi carriers and their tethering to the plasma membrane in preparation for exocytosis 109. Exocyst is also known to cooperate with Rab8 109. Of further interest is that the exocyst platform plays a role in TBK-1 activation, first observed in the context of innate type I interferon response to pathogen products, with the Sec5 component being in the complex 110. The exocyst has not yet been linked with autophagy-dependent unconventional secretion, albeit this would make sense given the known functions of the exocyst in secretion. Nevertheless, according to a report by M. White's group, different exocyst components can either promote (Exo84) or stall (Sec5) autophagy (59A). Our published data indicate that IL-1β in LC3+ profiles en route for unconventional secretion colocalize with Sec6, one of the exocyst components (27A). However, we could not efficiently knock down any of the exocyst parts in primary murine macrophages, the cell type where our entire study (27A) was executed, and thus could not establish a functional role in secretory autophagy. Human THP-1 cells, where knockdowns of exocyst components are routinely achieved, are examined (M. White, personal communication). It is determined whether Rab8, exocyst, and TBK-1 differentially regulate degradative autophagy versus secretory autophagy.

Technical.

Rab8a and Rab8b constitutively active and dominant negative mutants in our collection and will be used to probe the proposed effects on degradative versus secretory autophagy.

Example 10

Defining the Autophagic Secretome of a Mammalian Cell

Rationale.

Autophagy has a highly relevant ability to act as a topological inverter—taking a substrate that is in the cytoplasm and placing it into the lumen of the autophagosome, from where it can be either degraded upon fusion with lysosomes or secreted following fusion with the plasma membrane. The second possibility is examined and physical methods (mass spectrometry) are used to identify the protein entities that are substrates for secretory autophagy (autophagic secretome).

Identifying Autophagy-Dependent Unconventional Secretion Proteome (Autophagic Secretome).

Experiments and Interpretations.

Mass spectrometry is used to physically identify secretory cargo released from cells upon stimulation of autophagy. A similar approach has been applied for inflammasome-dependent release of proteins (65A). The difference vis-à-vis the previously published inflammasome study (65A) will be that we will use induction of autophagy and identify protein entities released into supernatants from Atg5-proficient cells but not from isogenic Atg5-deficient cells (subtractive analysis). Primary macrophages (BMMs) will be induced for autophagy for the period of time we have optimized to avoid nonspecific leakage of cytosolic proteins from cells (27A). The concentrated supernatants from Atg5fl/fl LysM-Cre+vs Cre– BMMs will be digested with trypsin. This is followed by labeling with isobaric chemical tags using Tandem Mass Tag reagent (Thermo Scientific) specific for the free N-ter Lys residues: TMT2-126 for Cre+ and TMT2-172 for Cre–. Peptides are identified and quantified by tandem mass spectrometry (MS/MS). In the first MS, the equivalent peptides are indistinguishable from each other, in the tandem MS mode, each tag generates a unique reporter ion. We have already carried out preliminary studies and show in Table 1 (FIG. 12B) a number of Atg5-dependent substrates released by secretory autophagy from bone marrow-derived macrophages. A total of 153 proteins were found as secreted in an Atg5-dependent manner as their presence was decreased in the supernatants from Atg5 knock-out BMMs (negative score in Table 1). Among species identified, in addition to new candidates there are known unconventionally secreted proteins—vimentin, galectin-1, galectin-3, ASC (an inflammasome component), ferritin and thioredoxin. These experiments are repeated with BMMs from Atg7fl/fl LysM-Cre+ mice to define the autophagic secretome.

Additional analyses are carried out with other cell types from mice with different Cre drivers (myeloid, lymphoid, epithelial, fibroblast, neural, general/tamoxifen) crossed with Atg5fl/fl and Atg7fl/fl mouse strains. Starvation and one cell type physiologically relevant stimulus for induction of autophagy is used, e.g.: ER stress, IFN-γ, microbial products, and endogenous damage-associated molecular patterns (alarmins). This permits testing of whether different cell types have different autophagic secretomes and agonist-dependent composition response patterns.

Changes in the secretory autophagy outputs should be observed, depending on different cell types and autophagy agonists used. In all experiments, release of cytosolic proteins independently of secretory autophagy is recorded by monitoring lactate dehydrogenase release and cell death, as in our published work (27A).

Alternatives:

(i) The murine proteins identified as substrates for autophagic secretion using BMMs and for which there are available antibodies are confirmed by immunoblots in autophagic secretions from BMMs. (ii) Secretion of confirmed proteins is tested with human primary peripheral blood monocyte-derived macrophages. (ii) Given that the mass spectroscopy approach has disadvantages due to the potential to miss a minor species of potentially high biological significance, a complementary biological activity-based tracking and purification approach to complement the physical identification approach may be considered. Addition of supernatants from autophagy-induced cells to the reporter cells is used. Some of the biological activities considered are: a) Programmed cell death (different types of cell death such as apoptosis, necrosis, necroptosis, pyroptosis). Of relevance here is that autophagy still has an incompletely defined tumor suppressor role, whereas IL-1β release is associated with pyroptotic cell death and thus other secretary autophagy substrates may have additional cell death modulating activities. b) Immunological functions (e.g. Th1 and Th17 polarization signals; or inflammasome agonists and neurodegenerative plaque generators such as Aβ42 of significance for Alzheimer's disease). c) Microbiological outputs such as direct killing of extracellular bacteria; we have previously shown that autophagy can generate intracellular neo-antimicrobial peptides from innocuous cytosolic components such as ribosomal proteins (86A).

References for Background of the Invention and Examples 2-10

1A Mizushima, N., Levine, B., Cuervo, A. M. & Klionsky, D. J. Autophagy fights disease through cellular self-digestion. *Nature* 451, 1069-1075 (2008).

2A Mizushima, N., Yoshimori, T. & Ohsumi, Y. The role of atg proteins in autophagosome formation. *Annual review of cell and developmental biology* 27, 107-132, doi: 10.1146/annurev-cellbio-092910-154005 (2011).

3A Sarbassov, D. D., Ali, S. M. & Sabatini, D. M. Growing roles for the mTOR pathway. *Curr Opin Cell Biol* 17, 596-603, doi:S0955-0674(05)00148-1 [pii]10.1016/j.ceb.2005.09.009 (2005).

4A Laplante, M. & Sabatini, D. M. mTOR signaling in growth control and disease. *Cell* 149, 274-293,doi: 10.1016/j.cell.2012.03.017 (2012).

5A Bar-Peled, L., Schweitzer, L. D., Zoncu, R. & Sabatini, D. M. Ragulator Is a GEF for the Rag GTPases that Signal Amino Acid Levels to mTORC1. *Cell* 150, 1196-1208, doi:10.1016/j.cell.2012.07.032 (2012).

6A Neufeld, T. P. TOR-dependent control of autophagy: biting the hand that feeds. *Curr Opin Cell Biol* 22, 157-168, doi:10.1016/j.ceb.2009.11.005 (2010).

7A Scott, R. C., Schuldiner, O. & Neufeld, T. P. Role and regulation of starvation-induced autophagy in the *Drosophila* fat body. *Dev Cell* 7, 167-178, doi:10.1016/j.devce1.2004.07.009 (2004).

8A Rabinowitz, J. D. & White, E. Autophagy and metabolism. *Science* 330, 1344-1348, doi:10.1126/science.1193497 (2010).

9A Green, D. R., Galluzzi, L. & Kroemer, G. Mitochondria and the autophagy-inflammation-cell death axis in organismal aging. *Science* 333, 1109-1112, doi:10.1126/science.1201940 (2011).

10A Rubinsztein, D. C., Marino, G. & Kroemer, G. Autophagy and aging. *Cell* 146, 682-695, doi:10.1016/j.cell.2011.07.030 (2011).

11A Rubinsztein, D. C., Codogno, P. & Levine, B. Autophagy modulation as a potential therapeutic target for diverse diseases. *Nature reviews. Drug discovery* 11, 709-730, doi:10.1038/nrd3802 (2012).

12A Deretic, V. Autophagy in innate and adaptive immunity. *Trends Immunol* 26, 523-528, doi:S1471-4906(05)00206-1 [pii] 10.1016/j.it.2005.08.003 (2005).

13A Deretic, V. Autophagy as an innate immunity paradigm: expanding the scope and repertoire of pattern recognition receptors. *Current opinion in immunology* 24, 21-31, doi:10.1016/j.coi.2011.10.006 (2012).

14A Deretic, V. & Levine, B. Autophagy, immunity, and microbial adaptations. *Cell Host Microbe* 5, 527-549, doi:S1931-3128(09)00183-8 [pii] 10.1016/j.chom.2009.05.016 (2009).

15A Levine, B. & Deretic, V. Unveiling the roles of autophagy in innate and adaptive immunity. *Nat Rev Immunol* 7, 767-777 (2007).

16A Levine, B., Mizushima, N. & Virgin, H. W. Autophagy in immunity and inflammation. *Nature* 469, 323-17A Deretic, V., Jiang, S. & Dupont, N. Autophagy intersections with conventional and unconventional secretion in tissue development, remodeling and inflammation. *Trends in cell biology* 22, 397-406,doi:10.1016/j.tcb.2012.04.008 (2012).

18A Cadwell, K. et al. A key role for autophagy and the autophagy gene Atg16l1 in mouse and human intestinal Paneth cells. *Nature* 456, 259-263 (2008).

19A DeSelm, C. J. et al. Autophagy proteins regulate the secretory component of osteoclastic bone resorption. *Dev Cell* 21, 966-974, doi:10.1016/j.devcel.2011.08.016 (2011).

20A Ushio, H. et al. Crucial role for autophagy in degranulation of mast cells. *The Journal of allergy and clinical immunology* 127, 1267-1276 e1266, doi:10.1016/j.jaci.2010.12.1078 (2011).

21A Marino, G. et al. Autophagy is essential for mouse sense of balance. *The Journal of clinical investigation* 120, 2331-2344, doi: 10.1172/JCI42601 (2010).

22A Ganesan, A. K. et al. Genome-wide siRNA-based functional genomics of pigmentation identifies novel genes and pathways that impact melanogenesis in human cells. *PLoS genetics* 4, e1000298,doi: 10.1371/journal.pgen.1000298 (2008).

23A Narita, M. et al. Spatial coupling of mTOR and autophagy augments secretory phenotypes. *Science* 332, 966-970, doi:10.1126/science.1205407 (2011).

24A Manjithaya, R., Anjard, C., Loomis, W. F. & Subramani, S. Unconventional secretion of *Pichia pastoris* Acb1 is dependent on GRASP protein, peroxisomal functions, and autophagosome formation. *J Cell Biol* 188, 537-546 (2010).

25A Bruns, C., McCaffery, J. M., Curwin, A. J., Duran, J. M. & Malhotra, V. Biogenesis of a novelcompartment for autophagosome-mediated unconventional protein secretion. *J Cell Biol* 195, 979-992,doi:10.1083/jcb.201106098 (2011).

26A Duran, J. M., Anjard, C., Stefan, C., Loomis, W. F. & Malhotra, V. Unconventional secretion of Acb1 is mediated by autophagosomes. *J Cell Biol* 188, 527-536 (2010).

27A Dupont, N. et al. Autophagy-based unconventional secretory pathway for extracellular delivery of IL-1beta. *The EMBO journal* 30, 4701-4711, doi:10.1038/emboj.2011.398 (2011).

28A Gee, H. Y., Noh, S. H., Tang, B. L., Kim, K. H. & Lee, M. G. Rescue of DeltaF508-CFTR Trafficking viaa GRASP-Dependent Unconventional Secretion Pathway. *Cell* 146, 746-760, doi:10.1016/j.cell.2011.07.021 (2011).

29A Giuliani, F., Grieve, A. & Rabouille, C. Unconventional secretion: a stress on GRASP. *Curr Opin Cell Biol* 23, 498-504, doi:10.1016/j.ceb.2011.04.005 (2011).

30A Nickel, W. & Rabouille, C. Mechanisms of regulated unconventional protein secretion. *Nat Rev Mol Cell Biol* 10, 148-155, doi:nrm2617 [pii] 10.1038/nrm2617 (2009).

31A Rabouille, C., Malhotra, V. & Nickel, W. Diversity of unconventional protein secretion. *Journal of Cell Science In press* (2012).

32A Cabral, M., Anjard, C., Malhotra, V., Loomis, W. F. & Kuspa, A. Unconventional secretion of AcbA in Dictyostelium discoideum through a vesicular intermediate. *Eukaryot Cell* 9, 1009-1017, doi:EC.00337-09 [pii] 10.1128/EC.00337-09 (2010).

33A Dinarello, C. A. Immunological and inflammatory functions of the interleukin-1 family. *Annual review of immunology* 27, 519-550, doi:10.1 146/annurev.immunol.021908.132612 (2009).

34A Andersson, U. & Tracey, K. J. HMGB1 Is a Therapeutic Target for Sterile Inflammation and Infection. *Annual review of immunology* 29, 139-162, doi:10.1146/annurev-immunol-030409-101323 (2011).

35A Taguchi, A. et al. Blockade of RAGE-amphoterin signalling suppresses tumour growth and metastases. *Nature* 405, 354-360, doi:10.1038/35012626 (2000).

36A Tang, D. et al. HMGB1 release and redox regulates autophagy and apoptosis in cancer cells. *Oncogene* 29, 5299-5310, doi:onc2010261 [pii] 10.1038/onc.2010.261 (2010).

37A Rabinovich, G. A. & Croci, D. O. Regulatory circuits mediated by lectin-glycan interactions in autoimmunity and cancer. *Immunity* 36, 322-335, doi:10.1016/j.immuni.2012.03.004 (2012).

38A Vasta, G. R. et al. Galectins as self/non-self recognition receptors in innate and adaptive immunity: an unresolved paradox. *Frontiers in immunology* 3, 199, doi: 10.3389/fimmu.2012.00199 (2012).

39A Vasta, G. R. Galectins as pattern recognition receptors: structure, function, and evolution. *Advances in experimental medicine and biology* 946, 21-36, doi:10.1007/978-1-4614-0106-32 (2012).

40A Starossom, S. C. et al. Galectin-1 deactivates classically activated microglia and protects from inflammation-induced neurodegeneration. *Immunity* 37, 249-263, doi: 10.1016/j.immuni.2012.05.023 (2012).

41A Liu, F. T. & Rabinovich, G. A. Galectins as modulators of tumour progression. *Nature reviews. Cancer* 5, 29-41, doi:10.1038/nrc1527 (2005).

42A Thijssen, V. L. et al. Galectin-1 is essential in tumor angiogenesis and is a target for antiangiogenesis therapy. *Proceedings of the National Academy of Sciences of the United States of America* 103, 15975-15980, doi:10.1073/pnas.0603883103 (2006).

43A Michaud, M. et al. Autophagy-dependent anticancer immune responses induced by chemotherapeutic agents in mice. *Science* 334, 1573-1577, doi:10.1126/science.1208347 (2011).

44A Egan, D. F. et al. Phosphorylation of ULK1 (hATG1) by AMP-activated protein kinase connects energy sensing to mitophagy. *Science* 331, 456-461, doi:10.1126/science.1196371 (2011).

45A Criollo, A. et al. Inhibition of autophagy by TAB2 and TAB3. *The EMBO journal* 30, 4908-4920,doi:10.1038/emboj.2011.413 (2011).

46A Nakatogawa, H., Ichimura, Y. & Ohsumi, Y. Atg8, a ubiquitin-like protein required for autophagosome formation, mediates membrane tethering and hemifusion. *Cell* 130, 165-178, doi:10.1016/j.cell.2007.05.021 (2007).

47A Weidberg, H. et al. LC3 and GATE-16 N termini mediate membrane fusion processes required for autophagosome biogenesis. *Dev Cell* 20, 444-454, doi: 10.1016/j.devcel.2011.02.006 (2011).

48A Nair, U. et al. SNARE proteins are required for macroautophagy. *Cell* 146, 290-302, doi:10.1016/j.cell.2011.06.022 (2011).

49A Deretic, V. Autophagy: an emerging immunological paradigm. *Journal of immunology* 189, 15-20, doi: 10.4049/jimmunol.1102108 (2012).

50A Zhou, R., Yazdi, A. S., Menu, P. & Tschopp, J. A role for mitochondria in NLRP3 inflammasome activation. *Nature* 469, 221-225, doi:10.1038/nature09663 (2011).

51A Nakahira, K. et al. Autophagy proteins regulate innate immune responses by inhibiting the release of mitochondrial DNA mediated by the NALP3 inflammasome. *Nature immunology* 12, 222-230, doi:10.1038/ni.1980 (2011).

52A Martinon, F., Petrilli, V., Mayor, A., Tardivel, A. & Tschopp, J. Gout-associated uric acid crystals activate the NALP3 inflammasome. *Nature* 440, 237-241 (2006).

53A Sun, Y., Bilan, P. J., Liu, Z. & Klip, A. Rab8A and Rab13 are activated by insulin and regulate GLUT4 translocation in muscle cells. *Proceedings of the National Academy of Sciences of the United States of America* 107, 19909-19914, doi:10.1073/pnas.1009523107 (2010).

54A Moritz, O. L. et al. Mutant rab8 Impairs docking and fusion of rhodopsin-bearing post-Golgi membranes and causes cell death of transgenic *Xenopus* rods. *Mol Biol Cell* 12, 2341-2351. (2001).

55A Bravo-Cordero, J. J. et al. MTI-MMP proinvasive activity is regulated by a novel Rab8-dependent exocytic pathway. *The EMBO journal* 26, 1499-1510, doi:10.1038/sj.emboj.7601606 (2007).

56A Nachury, M. V. et al. A core complex of BBS proteins cooperates with the GTPase Rab8 to promote ciliary membrane biogenesis. *Cell* 129, 1201-1213, doi: 10.1016/j.cell.2007.03.053 (2007).

57A Bryant, D. M. et al. A molecular network for de novo generation of the apical surface and lumen. *Nature cell biology* 12, 1035-1045, doi:10.1038/ncb2106 (2010).

58A Mazelova, J., Ransom, N., Astuto-Gribble, L., Wilson, M. C. & Deretic, D. Syntaxin 3 and SNAP-25 pairing, regulated by omega-3 docosahexaenoic acid, controls the delivery of rhodopsin for the biogenesis of cilia-derived sensory organelles, the rod outer segments. *J Cell Sci* 122, 2003-2013, doi:jcs.039982 [pii] 10.1242/jcs.039982 (2009).

59A Bodemann, B. O. et al. RalB and the Exocyst Mediate the Cellular Starvation Response by Direct Activation of Autophagosome Assembly. *Cell* 144, 253-267, doi: S0092-8674(10)01436-4 [pii]10.1016/j.cell.2010.12.018 (2011).

60A Kinseth, M. A. et al. The Golgi-associated protein GRASP is required for unconventional protein secretion during development. *Cell* 130, 524-534, doi:S0092-8674 (07)00826-4 [pii] 10.1016/j.cell.2007.06.029 (2007).

61A Mizushima, N., Yoshimori, T. & Levine, B. Methods in mammalian autophagy research. *Cell* 140, 313-326 (2010).

62A Kimura, S., Noda, T. & Yoshimori, T. Dissection of the autophagosome maturation process by a novel reporter protein, tandem fluorescent-tagged LC3. *Autophagy* 3, 452-460 (2007).

63A Tang, D. et al. Endogenous HMGB1 regulates autophagy. *J Cell Biol* 190, 881-892, doi:jcb.200911078 [pii] 10.1083/jcb.200911078 (2010).

64A Singh, S. B. et al. Human IRGM regulates autophagy and cell-autonomous immunity functions through mitochondria. *Nat Cell Biol* 12, 1154-1165, doi:ncb2119 [pii] 10.1038/ncb2119 (2010).

65A Keller, M., Ruegg, A., Werner, S. & Beer, H. D. Active caspase-1 is a regulator of unconventional protein secretion. *Cell* 132, 818-831, doi:10.1016/j.cell.2007.12.040 (2008).

66A Lamkanfi, M. Emerging inflammasome effector mechanisms. *Nature reviews. Immunology* 11, 213-220, doi: 10.1038/nri2936 (2011).

67A Lamkanfi, M. et al. Inflammasome-dependent release of the alarmin HMGB1 in endotoxemia. *Journal of immunology* 185, 4385-4392, doi:10.4049/jimmunol.1000803 (2010).

68A Willingham, S. B. et al. NLRP3 (NALP3, Cryopyrin) facilitates in vivo caspase-1 activation, necrosis, and HMGB1 release via inflammasome-dependent and -independent pathways. *Journal of immunology* 183, 2008-2015, doi:10.4049/jimmunol.0900138 (2009).

69A Axe, E. L. et al. Autophagosome formation from membrane compartments enriched in phosphatidylinositol 3-phosphate and dynamically connected to the endoplasmic reticulum. *J Cell Biol* 182, 685-701 (2008).

70A Hayashi-Nishino, M. et al. A subdomain of the endoplasmic reticulum forms a cradle for autophagosome formation. *Nature cell biology* 11, 1433-1437, doi:10.1038/ncb1991 (2009).

71A Moreau, K., Ravikumar, B., Renna, M., Puri, C. & Rubinsztein, D. C. Autophagosome precursor maturation requires homotypic fusion. *Cell* 146, 303-317, doi:10.1016/j.cell.2011.06.023 (2011).

72A Hailey, D. W. & Lippincott-Schwartz, J. Using photoactivatable proteins to monitor autophagosome lifetime. *Methods Enzymol* 452, 25-45, doi:S0076-6879(08)03603-3 [pii]10.1016/50076-6879(08)03603-3 (2009).

73A Young, A. R. et al. Starvation and ULK1-dependent cycling of mammalian Atg9 between the TGN and endosomes. *J Cell Sci* 119, 3888-3900 (2006).

74A Yen, W. L. et al. The conserved oligomeric Golgi complex is involved in double-membrane vesicle formation during autophagy. *J Cell Biol* 188, 101-114, doi:jcb.200904075 [pii] 10.1083/jcb.200904075 (2010).

75A Yamamoto, H. et al. Atg9 vesicles are an important membrane source during early steps of autophagosome formation. *J Cell Biol* 198, 219-233, doi:10.1083/jcb.201202061 (2012).

76A Lum, J. J., DeBerardinis, R. J. & Thompson, C. B. Autophagy in metazoans: cell survival in the land of plenty. *Nat Rev Mol Cell Biol* 6, 439-448 (2005).

77A Bernales, S., McDonald, K. L. & Walter, P. Autophagy counterbalances endoplasmic reticulum expansion during the unfolded protein response. *PLoS Biol* 4, e423 (2006).

78A Schotman, H., Karhinen, L. & Rabouille, C. dGRASP-mediated noncanonical integrin secretion is required for *Drosophila* epithelial remodeling. *Dev Cell* 14, 171-182, doi:10.1016/j.devcel.2007.12.006 (2008).

79A Glick, B. S. & Nakano, A. Membrane traffic within the Golgi apparatus. *Annual review of cell and developmental biology* 25, 113-132, doi: 10.1146/annurev.cellbio.24.110707.175421 (2009).

80A Lorente-Rodriguez, A. & Barlowe, C. Entry and exit mechanisms at the cis-face of the Golgi complex. *Cold Spring Harbor perspectives in biology* 3, doi:10.1101/cshperspect.a005207 (2011).

81A Truschel, S. T., Zhang, M., Bachert, C., Macbeth, M. R. & Linstedt, A. D. Allosteric regulation of GRASP protein-dependent Golgi membrane tethering by mitotic phosphorylation. *The Journal of biological chemistry* 287, 19870-19875, doi:10.1074/jbc.M111.326256 (2012).

82A Jarvela, T. & Linstedt, A. Golgi GRASPs: moonlighting membrane tethers. *Cell Health and Cytoskeleton* 4, 37-47 (2012).

83A Roberts, E. A. & Deretic, V. Autophagic proteolysis of long-lived proteins in nonliver cells. *Methods Mol Biol* 445, 111-117 (2008).

84A Ponpuak, M., Delgado, M. A., Elmaoued, R. A. & Deretic, V. Monitoring autophagy during *Mycobacterium tuberculosis* infection. *Methods Enzymol* 452, 345-361, doi:S0076-6879(08)03621-5 [pii] 10.1016/S0076-6879(08)03621-5 (2009).

85A Pilli, M. et al. TBK-1 Promotes Autophagy-Mediated Antimicrobial Defense by Controlling Autophagosome Maturation. *Immunity* 37, 223-234, doi:10.1016/j.immuni.2012.04.015 (2012).

86A Ponpuak, M. et al. Delivery of cytosolic components by autophagic adaptor protein p62 endows autophagosomes with unique antimicrobial properties. *Immunity* 32, 329-341 (2010).

87A Miller, J. C. et al. A TALE nuclease architecture for efficient genome editing. *Nature biotechnology* 29, 143-148, doi:10.1038/nbt.1755 (2011).

88A Tang, H. W. et al. Atg1-mediated myosin II activation regulates autophagosome formation during starvation-induced autophagy. *The EMBO journal* 30, 636-651, doi:10.1038/emboj.2010.338 (2011).

89A Soderberg, O. et al. Direct observation of individual endogenous protein complexes in situ by proximity ligation. *Nature methods* 3, 995-1000, doi:10.1038/nmeth947 (2006).

90A Ishihara, N. et al. Autophagosome requires specific early Sec proteins for its formation and NSF/SNARE for vacuolar fusion. *Mol Biol Cell* 12, 3690-3702 (2001).

91A Proikas-Cezanne, T. et al. WIPI-1alpha (WIPI49), a member of the novel 7-bladed WIPI protein family, is aberrantly expressed in human cancer and is linked to starvation-induced autophagy. *Oncogene* 23, 9314-9325 (2004).

92A Wei, Y., Pattingre, S., Sinha, S., Bassik, M. & Levine, B. JNK1-mediated phosphorylation of Bcl-2 regulates starvation-induced autophagy. *Mol Cell* 30, 678-688 (2008).

93A Urano, F. et al. Coupling of stress in the ER to activation of JNK protein kinases by transmembrane protein kinase IRE1. *Science* 287, 664-666 (2000).

94A Lu, B. et al. Novel role of PKR in inflammasome activation and HMGB1 release. *Nature* 488, 670-674,doi:10.1038/nature11290 (2012).

95A Talloczy, Z. et al. Regulation of starvation- and virus-induced autophagy by the eIF2alpha kinase signaling pathway. *Proc Natl Acad Sci USA* 99, 190-195 (2002).

96A Tsukamoto, S. et al. Autophagy is essential for preimplantation development of mouse embryos. Science 321, 117-120 (2008).

97A Lynch-Day, M. A. et al. Trs85 directs a Ypt1 GEF, TRAPPIII, to the phagophore to promote autophagy. Proc Natl Acad Sci USA 107, 7811-7816, doi:1000063107 [pii]10.1073/pnas.1000063107 (2010).

98A Meiling-Wesse, K. et al. Trs85 (Gsg1), a component of the TRAPP complexes, is required for the organization of the preautophagosomal structure during selective autophagy via the Cvt pathway. *J Biol Chem* 280, 33669-33678 (2005).

99A Weidberg, H. et al. LC3 and GATE-16/GABARAP subfamilies are both essential yet act differently in autophagosome biogenesis. *The EMBO journal* 29, 1792-1802, doi:10.1038/emboj.2010.74 (2010).

100A Wild, P. et al. Phosphorylation of the autophagy receptor optineurin restricts *Salmonella* growth. *Science* 333, 228-233, doi:10.1126/science.1205405 (2011).

101A Thurston, T. L., Wandel, M. P., von Muhlinen, N., Foeglein, A. & Randow, F. Galectin 8 targets damaged vesicles for autophagy to defend cells against bacterial invasion. *Nature* 482, 414-418, doi:10.1038/nature10744 (2012).

102A Kirkin, V. et al. A role for NBR1 in autophagosomal degradation of ubiquitinated substrates. *Mol Cell* 33, 505-516 (2009).

103A Johansen, T. & Lamark, T. Selective autophagy mediated by autophagic adapter proteins. *Autophagy* 7, 279-296 (2011).

104A Matsumoto, G., Wada, K., Okuno, M., Kurosawa, M. & Nukina, N. Serine 403 Phosphorylation of p62/SQSTM1 Regulates Selective Autophagic Clearance of Ubiquitinated Proteins. *Molecular Cell* 44, 279-289 (2011).

105A Stenmark, H. Rab GTPases as coordinators of vesicle traffic. *Nat Rev Mol Cell Biol* 10, 513-525, doi:nrm2728 [pii] 10.1038/nrm2728 (2009).

106A Rezaie, T. et al. Adult-onset primary open-angle glaucoma caused by mutations in optineurin. *Science* 295, 1077-1079, doi:10.1126/science.1066901 (2002).

107A Morton, S., Hesson, L., Peggie, M. & Cohen, P. Enhanced binding of TBK1 by an optineurin mutant that causes a familial form of primary open angle glaucoma. *FEBS Lett* 582, 997-1002, doi:S0014-5793(08)00160-9 [pii] 10.1016/j.febslet.2008.02.047 (2008).

108A Rusten, T. E., Vaccari, T. & Stenmark, H. Shaping development with ESCRTs. *Nature cell biology* 14, 38-45, doi:10.1038/ncb2381 (2012).

109A Munson, M. & Novick, P. The exocyst defrocked, a framework of rods revealed. *Nature structural & molecular biology* 13, 577-581, doi:10.1038/nsmb1097 (2006).

110A Ishikawa, H., Ma, Z. & Barber, G. N. STING regulates intracellular DNA-mediated, type I interferondependent innate immunity. *Nature* 461, 788-792, doi:10.1038/nature08476 (2009).

What is claimed is:

1. A pharmaceutical composition in aerosol delivery form for delivery to a patient or subject in need of treatment for a tuberculosis infection comprising an effective amount of an autophagy modulator compound which is flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, benzethonium, niclosamide, monensin, bromperidol, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, methimazole, trimeprazine, ethoxyquin, clocortolone, doxycycline, pirlindole mesylate, doxazosin, deptropine, nocodazole, scopolamine, oxybenzone, halcinonide, oxybutynin, miconazole, clomipramine, cyproheptadine, doxepin, dyclonine, salbutamol, flavoxate, amoxapine, fenofibrate, pimethixene, a pharmaceutically acceptable salt thereof, or a mixture thereof, wherein said autophagy modulator compound is further formulated in combination with an additional anti-tuberculosis agent.

2. The pharmaceutical composition according to claim 1 wherein said additional anti-tuberculosis agent is aminosalicylic acid, isoniazid, ethionamide, myambutol, rifampin, rifabutin, rifapentine, carpeomycin, cycloserine, or a pharmaceutically acceptable salt or a mixture thereof.

3. The composition according to claim 2 wherein said autophagy modulator compound is bromhexine.

4. A method of inhibiting, reducing the likelihood or treating a tuberculosis infection in a patient or subject comprising administering to a patient in need an effective amount of an autophagy modulator compound, in combination with an anti-tuberculosis agent selected from the group consisting of aminosalicylic acid, isoniazid, ethionamide, myambutol, rifampin, rifabutin, rifapentine, carpeomycin, cycloserine, or a pharmaceutically acceptable salt or a mixture thereof.

5. The method according to claim 4 wherein said tuberculosis infection is drug resistant.

6. The method according to claim 5 wherein said tuberculosis infection is multiple drug resistant.

7. The method according to claim 4 wherein said autophagy modulator compound is an autophagy agonist.

8. The method according to claim 4 wherein said autophagy modulator compound is flubendazole, hexachlorophene, propidium iodide, bepridil, clomiphene citrate (Z,E), GBR 12909, propafenone, metixene, dipivefrin, fluvoxamine, dicyclomine, dimethisoquin, ticlopidine, memantine, bromhexine, norcyclobenzaprine, diperodon, nortriptyline, a mixture thereof or a pharmaceutically acceptable salt thereof.

9. The method according to claim 4 wherein said autophagy modulator compound is benzethonium, niclosamide, monensin, bromperidol, bromhexine, levobunolol, dehydroisoandosterone 3-acetate, sertraline, tamoxifen, reserpine, hexachlorophene, dipyridamole, harmaline, prazosin, lidoflazine, thiethylperazine, dextromethorphan, desipramine, mebendazole, canrenone, chlorprothixene, maprotiline, homochlorcyclizine, loperamide, nicardipine, dexfenfluramine, nilvadipine, dosulepin, biperiden, denatonium, etomidate, toremifene, tomoxetine, clorgyline, zotepine, beta-escin, tridihexethyl, ceftazidime, methoxy-6-harmalan, melengestrol, albendazole, rimantadine, chlorpromazine, pergolide, cloperastine, prednicarbate, haloperidol, clotrimazole, nitrofural, iopanoic acid, naftopidil, Methimazole, Trimeprazine, Ethoxyquin, Clocortolone, Doxycycline, Pirlindole mesylate, Doxazosin, Deptropine, Nocodazole, Scopolamine, Oxybenzone, Halcinonide, Oxybutynin, Miconazole, Clomipramine, Cyproheptadine, Doxepin, Dyclonine, Salbutamol, Flavoxate, Amoxapine, Fenofibrate, Pimethixene, or a pharmaceutically acceptable salt or mixture thereof.

10. The method according to claim 4 wherein said autophagy modulator compound is bromhexine and said anti-tuberculosis agent is rifampin.

* * * * *